(12) United States Patent
Uutela et al.

(10) Patent No.: US 7,105,481 B2
(45) Date of Patent: Sep. 12, 2006

(54) METHOD FOR STIMULATING CONNECTIVE TISSUE GROWTH OR WOUND HEALING

(75) Inventors: Marko Uutela, University of Helsinki (FI); Ulf Eriksson, Stockholm (SE); Kari Alitalo, University of Helsinki (FI)

(73) Assignees: Ludwig Institute for Cancer Research, New York, NY (US); Licentia Ltd., Helsinki (FI)

( * ) Notice: Subject to any disclaimer, the term of this patent is extended or adjusted under 35 U.S.C. 154(b) by 453 days.

(21) Appl. No.: 10/260,539

(22) Filed: Oct. 1, 2002

(65) Prior Publication Data

US 2003/0073637 A1 Apr. 17, 2003

Related U.S. Application Data

(63) Continuation-in-part of application No. 10/086,623, filed on Mar. 4, 2002, and a continuation-in-part of application No. 09/691,200, filed on Oct. 19, 2000, now abandoned, which is a continuation-in-part of application No. 09/438,046, filed on Nov. 10, 1999, now Pat. No. 6,706,687.

(60) Provisional application No. 60/107,852, filed on Nov. 10, 1998, provisional application No. 60/113,997, filed on Dec. 28, 1998, provisional application No. 60/150,604, filed on Aug. 26, 1999, provisional application No. 60/157,108, filed on Oct. 4, 1999, provisional application No. 60/157,756, filed on Oct. 5, 1999.

(51) Int. Cl.
*A61K 38/18* (2006.01)

(52) U.S. Cl. .................... 514/2; 514/8; 514/12
(58) Field of Classification Search .............. 514/2, 514/8, 12, 885
See application file for complete search history.

(56) References Cited

U.S. PATENT DOCUMENTS 5,607,918 A 3/1997 Eriksson et al. .............. 514/12

FOREIGN PATENT DOCUMENTS

| WO | WO 96/27007 | 9/1996 |
|----|-------------|--------|
| WO | WO 00/34474 | 6/2000 |
| WO | WO 00/66736 | 11/2000 |

OTHER PUBLICATIONS

Mikayama et al. Proc. Natl. Acad. Sci. USA vol. 90, pp. 10056-10060.*
Voet et al. Biochemistry John Wiley & Sons, Inc., pp. 126-128 and 228-234.*
Database GENCORE on EST, AN AA488780, NCI-CGAP, National Cancer Institute, Cancer Genome Anatomy Project (CGAP), Tumor Gene Index. Gene Sequence, Aug. 15, 1997.
Database GENCORE on EST, AN AA488996, NCI-CGAP, National Cancer Institute, Cancer Genome Anatomy Project (CGAP), tumor Gene Index, Gene Sequence, Aug. 15, 1997.
Database GENCORE on EST, AN AA 736766, NCI-CGAP, National Cancer Institute, Cancer Genome Anatomy Project (CGAP), Tumor Gene Index, Gene Sequence, Jan. 23, 1998.
Database GENCORE on EST, AN AQ041639, Adams et al. Use of a random BAC End Sequence Database for Sequence-Ready Map Building (1998), Gene Sequence, Jul. 14, 1998.
International Search Report, Apr. 25, 2000.
Miyama et al., Moleuclar Cloning and Functional Expression of a cDNA Encoding Glycosylation-Inhibiting Factor, 1993, Proc. Natl. Acad. Sci., pp. 10056-10060, vol. 90, USA.
Voet et al., "Biochemistry", pp. 126-128 and pp. 228-234, John Wiley & Sons, Inc.

* cited by examiner

*Primary Examiner*—Prema Mertz
(74) *Attorney, Agent, or Firm*—Crowell & Moring LLP

(57) ABSTRACT

PDGF-D, a new member of the PDGF/VEGF family of growth factors, as well as the nucleotide sequence encoding it, methods for producing it, antibodies and other antagonists to it, transfected and transformed host cells expressing it, pharmaceutical compositions containing it, and uses thereof in medical and diagnostic applications, including methods for stimulating growth of a connective tissue or healing a wound in a mammal, which methods comprise administering to the mammal an effective amount of PDGF-D polypeptides or polynucleotides encoding the PDGF-D polypeptides.

8 Claims, 24 Drawing Sheets

```
aattgtggct gtggaactgt caactggagg tcctgcacat gcaattcagg gaaaaccgtg  60
aaaaagtatc atgaggtatt acagtttgag cctggccaca tcaagaggag gggtagagct 120
aagaccatgg ctctagttga catccagttg gatcaccatg aacgatgtga ttgtatctgc 180
agctcaagac cacctcgata agagaatgtg cacatcctta cattaagcct gaaagaacca 240
ttagtttaag gagggtgaga taagagaccc ttttcctacc agcaaccaga cttactacta 300
gcctgcaatg caatgaacac aagtggttgc tgagtctcag ccttgctttg ttaatgccat 360
```

Fig. 1

Asn Cys Gly Cys Gly Thr Val Asn Trp Arg Ser Cys Thr Cys Asn Ser
 1           5                  10                  15
Gly Lys Thr Val Lys Lys Tyr His Glu Val Leu Gln Phe Glu Pro Gly
             20              25                  30
His Ile Lys Arg Arg Gly Arg Ala Lys Thr Met Ala Leu Val Asp Ile
         35              40                  45
Gln Leu Asp His His Glu Arg Cys Asp Cys Ile Cys Ser Ser Arg Pro
     50              55                  60
Pro Arg
65

Fig. 2

```
ggaagatttc caacccgcag cagcttcaga gaccaactgg aatctgtcac aagctctgtt  60
tcagggtatc cctataactc tccatcagta acggatccca ctctgattgc ggatgctctg 120
gacaaaaaaa ttgcagaatt tgatacagtg aagatctgc tcaagtactt caatccagag 180
tcatggcaag aagatcttga gaatatgtat ctggacaccc ctcggtatcg aggcaggtca 240
taccatgacc ggaagtcaaa agttgacctg gataggctca atgatgatgc caagcgttac 300
agttgcactc ccaggaatta ctcggtcaat ataagagaag agctgaagtt ggccaatgtg 360
gtcttctttc cacgttgcct cctcgtgcag cgctgtggag gaaattgtgg ctgtggaact 420
gtcaaactgg agtcctgcac atgcaattca gggaaaaccg tgaaaaagta tcatgaggta 480
ttacagtttg agcctggcca catcaagagg aggggtagag ctaagaccat ggctctagtt 540
gacatccagt tggatcacca tgaacgatgc gattgtatct gcagctcaag accacctcga 600
taagagaatg tgcacatcct tacattaagc ctgaaagaac ctttagttta aggagggtga 660
gataagagac ccttttccta ccagcaaccc                                   690
```

Fig. 3

Gly Arg Phe Pro Thr Arg Ser Ser Phe Arg Asp Gln Leu Glu Ser Val
1           5                   10                  15

Thr Ser Ser Val Ser Gly Tyr Pro Tyr Asn Ser Pro Ser Val Thr Asp
            20                  25                  30

Pro Thr Leu Ile Ala Asp Ala Leu Asp Lys Lys Ile Ala Glu Phe Asp
            35                  40                  45

Thr Val Glu Asp Leu Leu Lys Tyr Phe Asn Pro Glu Ser Trp Gln Glu
    50                  55                  60

Asp Leu Glu Asn Met Tyr Leu Asp Thr Pro Arg Tyr Arg Gly Arg Ser
65                  70                  75                  80

Tyr His Asp Arg Lys Ser Lys Val Asp Leu Asp Arg Leu Asn Asp Asp
                85                  90                  95

Ala Lys Arg Tyr Ser Cys Thr Pro Arg Asn Tyr Ser Val Asn Ile Arg
            100                 105                 110

Glu Glu Leu Lys Leu Ala Asn Val Val Phe Phe Pro Arg Cys Leu Leu
        115                 120                 125

Val Gln Arg Cys Gly Gly Asn Cys Gly Cys Gly Thr Val Lys Leu Glu
    130                 135                 140

Ser Cys Thr Cys Asn Ser Gly Lys Thr Val Lys Lys Tyr His Glu Val
145                 150                 155                 160

Leu Gln Phe Glu Pro Gly His Ile Lys Arg Arg Gly Arg Ala Lys Thr
            165                 170                 175

Met Ala Leu Val Asp Ile Gln Leu Asp His His Glu Arg Cys Asp Cys
            180                 185                 190

Ile Cys Ser Ser Arg Pro Pro Arg
        195                 200

Fig. 4

```
ttgtaccgaa gagatgagac catccaggtg aaaggaaacg gctacgtgca gagtcctaga  60
ttcccgaaca gctaccccag gaacctgctc ctgacatggc ggcttcactc tcaggagaat 120
acacggatac agctagtgtt tgacaatcag tttggattag aggaagcaga aaatgatatc 180
tgtaggtatg attttgtgga agttgaagat atatccgaaa ccagtaccat tattagagga 240
cgatggtgtg gacacaagga agttcctcca aggataaaat caagaacgaa ccaaattaaa 300
atcacattca agtccgatga ctactttgtg gctaaacctg gattcaagat ttattattct 360
ttgctggaag atttccaacc cgcagcagct tcagagacca actgggaatc tgtcacaagc 420
tctatttcag gggtatccta taactctcca tcagtaacgg atcccactct gattgcggat 480
gctctggaca aaaaaattgc agaatttgat acagtggaag atctgctcaa gtacttcaat 540
ccagagtcat ggcaagaaga tcttgagaat atgtatctgg acacccctcg gtatcgaggc 600
aggtcatacc atgaccggaa gtcaaaagtt gacctggata ggctcaatga tgatgccaag 660
cgttacagtt gcactcccag gaattactcg gtcaatataa gagaagagct gaagttggcc 720
aatgtggtct tctttccacg ttgcctcctc gtgcagcgct gtggaggaaa ttgtggctgt 780
ggaactgtca actggaggtc ctgcacatgc aattcaggga aaaccgtgaa aaagtatcat 840
gaggtattac agtttgagcc tggccacatc aagaggaggg gtagagctaa gaccatggct 900
ctagttgaca tccagttgga tcaccatgaa cgatgcgatt gtatctgcag ctcaagacca 960
cctcgataag agaatgtgca catccttaca ttaagcctga agaacctttt agtttaagga 1020
gggtgagata agagacccctt ttcctaccag caaccaaact tactactagc ctgcaatgca 1080
atgaacacaa gtggttgctg agtctcagcc ttgctttgtt aatgccatgg caagtagaaa 1140
ggtatatcat caacttctat acctaagaat ataggattgc atttaataat agtgtttgag 1200
gttatatatg cacaaacaca cacagaaata tattcatgtc tatgtgtata tagatcaaat 1260
gtttttttg gtatatataa ccaggtacac cagagcttac atatgtttga gttagactct 1320
taaaatcctt tgccaaaata agggatggtc aaatatatga aacatgtctt tagaaaattt 1380
aggagataaa tttatttta aattttgaaa cacaaaacaa ttttgaatct tgctctctta 1440
aagaaagcat cttgtatatt aaaaatcaaa agatgaggct ttcttacata tacatcttag 1500
ttgattatta aaaaggaaa aaggtttcca gagaaaaggc caatacctaa gcattttttc 1560
catgagaagc actgcatact tacctatgtg gactgtaata acctgtctcc aaaaccatgc 1620
cataataata taagtgcttt agaaattaaa tcattgtgtt ttttatgcat tttgctgagg 1680
catccttatt catttaacac ctatctcaaa aacttactta gaaggttttt tattatagtc 1740
ctacaaaaga caatgtataa gctgtaacag aattttgaat tgttttctt tgcaaaaccc 1800
ctccacaaaa gcaaatcctt tcaagaatgg catgggcatt ctgtatgaac ctttccagat 1860
ggtgttcagt gaaagatgtg ggtagttgag aacttaaaaa gtgaacattg aaacatcgac 1920
gtaactggaa accg                                                  1934
```

Fig. 5

Leu Tyr Arg Arg Asp Glu Thr Ile Gln Val Lys Gly Asn Gly Tyr Val
 1           5                   10                  15

Gln Ser Pro Arg Phe Pro Asn Ser Tyr Pro Arg Asn Leu Leu Leu Thr
            20                  25                  30

Trp Arg Leu His Ser Gln Glu Asn Thr Arg Ile Gln Leu Val Phe Asp
        35                  40                  45

Asn Gln Phe Gly Leu Glu Glu Ala Glu Asn Asp Ile Cys Arg Tyr Asp
    50                  55                  60

Phe Val Glu Val Glu Asp Ile Ser Glu Thr Ser Thr Ile Ile Arg Gly
65                  70                  75                  80

Arg Trp Cys Gly His Lys Glu Val Pro Pro Arg Ile Lys Ser Arg Thr
            85                  90                  95

```
Asn Gln Ile Lys Ile Thr Phe Lys Ser Asp Asp Tyr Phe Val Ala Lys
            100             105                 110
Pro Gly Phe Lys Ile Tyr Tyr Ser Leu Leu Glu Asp Phe Gln Pro Ala
            115             120                 125
Ala Ala Ser Glu Thr Asn Trp Glu Ser Val Thr Ser Ser Ile Ser Gly
        130             135                 140
Val Ser Tyr Asn Ser Pro Ser Val Thr Asp Pro Thr Leu Ile Ala Asp
145                 150                 155                 160
Ala Leu Asp Lys Lys Ile Ala Glu Phe Asp Thr Val Glu Asp Leu Leu
            165             170                 175
Lys Tyr Phe Asn Pro Glu Ser Trp Gln Glu Asp Leu Glu Asn Met Tyr
            180             185                 190
Leu Asp Thr Pro Arg Tyr Arg Gly Arg Ser Tyr His Asp Arg Lys Ser
            195             200                 205
Lys Val Asp Leu Asp Arg Leu Asn Asp Asp Ala Lys Arg Tyr Ser Cys
    210             215                 220
Thr Pro Arg Asn Tyr Ser Val Asn Ile Arg Glu Glu Leu Lys Leu Ala
225             230                 235                 240
Asn Val Val Phe Phe Pro Arg Cys Leu Leu Val Gln Arg Cys Gly Gly
            245                 250                 255
Asn Cys Gly Cys Gly Thr Val Asn Trp Arg Ser Cys Thr Cys Asn Ser
            260             265                 270
Gly Lys Thr Val Lys Lys Tyr His Glu Val Leu Gln Phe Glu Pro Gly
        275             280                 285
His Ile Lys Arg Arg Gly Arg Ala Lys Thr Met Ala Leu Val Asp Ile
    290             295                 300
Gln Leu Asp His His Glu Arg Cys Asp Cys Ile Cys Ser Ser Arg Pro
305             310                 315                 320
Pro Arg
```

```
cgctcggaaa gttcagcatg caggaagttt ggggagagct cggcgattag cacagcgacc  60
cgggccagcg cagggcgagc gcaggcggcg agagcgcagg gcggcgcggc gtcggtcccg 120
ggagcagaac ccggcttttt cttggagcga cgctgtctct agtcgctgat cccaa      175
```

```
atg cac cgg ctc atc ttt gtc tac act cta atc tgc gca aac ttt tgc   223
Met His Arg Leu Ile Phe Val Tyr Thr Leu Ile Cys Ala Asn Phe Cys
 1               5                  10                  15 agc tgt cgg gac act tct gca acc ccg cag agc gca tcc atc aaa gct   271
Ser Cys Arg Asp Thr Ser Ala Thr Pro Gln Ser Ala Ser Ile Lys Ala
             20                  25                  30 ttg cgc aac gcc aac ctc agg cga gat gag agc aat cac ctc aca gac   319
Leu Arg Asn Ala Asn Leu Arg Arg Asp Glu Ser Asn His Leu Thr Asp
         35                  40                  45 ttg tac cga aga gat gag acc atc cag gtg aaa gga aac ggc tac gtg   367
Leu Tyr Arg Arg Asp Glu Thr Ile Gln Val Lys Gly Asn Gly Tyr Val
     50                  55                  60 cag agt cct aga ttc ccg aac agc tac ccc agg aac ctg ctc ctg aca   415
Gln Ser Pro Arg Phe Pro Asn Ser Tyr Pro Arg Asn Leu Leu Leu Thr
 65                  70                  75                  80 tgg cgg ctt cac tct cag gag aat aca cgg ata cag cta gtg ttt gac   463
Trp Arg Leu His Ser Gln Glu Asn Thr Arg Ile Gln Leu Val Phe Asp
                 85                  90                  95 aat cag ttt gga tta gag gaa gca gaa aat gat atc tgt agg tat gat   511
Asn Gln Phe Gly Leu Glu Glu Ala Glu Asn Asp Ile Cys Arg Tyr Asp
            100                 105                 110 ttt gtg gaa gtt gaa gat ata tcc gaa acc agt acc att att aga gga   559
Phe Val Glu Val Glu Asp Ile Ser Glu Thr Ser Thr Ile Ile Arg Gly
        115                 120                 125 cga tgg tgt gga cac aag gaa gtt cct cca agg ata aaa tca aga acg   607
Arg Trp Cys Gly His Lys Glu Val Pro Pro Arg Ile Lys Ser Arg Thr
    130                 135                 140 aac caa att aaa atc aca ttc aag tcc gat gac tac ttt gtg gct aaa   655
Asn Gln Ile Lys Ile Thr Phe Lys Ser Asp Asp Tyr Phe Val Ala Lys
145                 150                 155                 160
```

```
cct gga ttc aag att tat tat tct ttg ctg gaa gat ttc caa ccc gca    703
Pro Gly Phe Lys Ile Tyr Tyr Ser Leu Leu Glu Asp Phe Gln Pro Ala
            165             170             175 gca gct tca gag acc aac tgg gaa tct gtc aca agc tct att tca ggg    751
Ala Ala Ser Glu Thr Asn Trp Glu Ser Val Thr Ser Ser Ile Ser Gly
        180             185             190 gta tcc tat aac tct cca tca gta acg gat ccc act ctg att gcg gat    799
Val Ser Tyr Asn Ser Pro Ser Val Thr Asp Pro Thr Leu Ile Ala Asp
        195             200             205 gct ctg gac aaa aaa att gca gaa ttt gat aca gtg gaa gat ctg ctc    847
Ala Leu Asp Lys Lys Ile Ala Glu Phe Asp Thr Val Glu Asp Leu Leu
    210             215             220 aag tac ttc aat cca gag tca tgg caa gaa gat ctt gag aat atg tat    895
Lys Tyr Phe Asn Pro Glu Ser Trp Gln Glu Asp Leu Glu Asn Met Tyr
225             230             235             240 ctg gac acc cct cgg tat cga ggc agg tca tac cat gac cgg aag tca    943
Leu Asp Thr Pro Arg Tyr Arg Gly Arg Ser Tyr His Asp Arg Lys Ser
                245             250             255 aaa gtt gac ctg gat agg ctc aat gat gat gcc aag cgt tac agt tgc    991
Lys Val Asp Leu Asp Arg Leu Asn Asp Asp Ala Lys Arg Tyr Ser Cys
            260             265             270 act ccc agg aat tac tcg gtc aat ata aga gaa gag ctg aag ttg gcc   1039
Thr Pro Arg Asn Tyr Ser Val Asn Ile Arg Glu Glu Leu Lys Leu Ala
        275             280             285 aat gtg gtc ttc ttt cca cgt tgc ctc ctc gtg cag cgc tgt gga gga   1087
Asn Val Val Phe Phe Pro Arg Cys Leu Leu Val Gln Arg Cys Gly Gly
        290             295             300 aat tgt ggc tgt gga act gtc aac tgg agg tcc tgc aca tgc aat tca   1135
Asn Cys Gly Cys Gly Thr Val Asn Trp Arg Ser Cys Thr Cys Asn Ser
305             310             315             320 ggg aaa acc gtg aaa aag tat cat gag gta tta cag ttt gag cct ggc   1183
Gly Lys Thr Val Lys Lys Tyr His Glu Val Leu Gln Phe Glu Pro Gly
            325             330             335
```

Fig. 7 cont.

```
cac atc aag agg agg ggt aga gct aag acc atg gct cta gtt gac atc    1231
His Ile Lys Arg Arg Gly Arg Ala Lys Thr Met Ala Leu Val Asp Ile
            340             345             350 cag ttg gat cac cat gaa cga tgc gat tgt atc tgc agc tca aga cca    1279
Gln Leu Asp His His Glu Arg Cys Asp Cys Ile Cys Ser Ser Arg Pro
            355             360             365 cct cga taagagaatg tgcacatcct tacattaagc ctgaaagaac ctttagttta    1335
Pro Arg
    370 aggagggtga gataagagac cctttccta ccagcaacca aacttactac tagcctgcaa 1395
tgcaatgaac acaagtggtt gctgagtctc agccttgctt tgttaatgcc atggcaagta 1455
gaaaggtata tcatcaactt ctatacctaa gaatatagga ttgcatttaa taatagtgtt 1515
tgaggttata tatgcacaaa cacacacaga aatatattca tgtctatgtg tatatagatc 1575
aaatgttttt tttggtatat ataaccaggt acaccagagc ttacatatgt ttgagttaga 1635
ctcttaaaat ccttttgccaa ataagggat ggtcaaatat atgaaacatg tctttagaaa 1695
atttaggaga taaatttatt tttaaatttt gaaacacaaa acaattttga atcttgctct 1755
cttaaagaaa gcatcttgta tattaaaat caaaagatga ggctttctta catatacatc 1815
ttagttgatt attaaaaaag gaaaaaggtt tccagagaaa aggccaatac ctaagcattt 1875
tttccatgag aagcactgca tacttaccta tgtggactgt aataacctgt ctccaaaacc 1935
atgccataat aatataagtg ctttagaaat taaatcattg tgttttttat gcattttgct 1995
gaggcatcct tattcattta acacctatct caaaaactta cttagaaggt tttttattat 2055
agtcctacaa aagacaatgt ataagctgta acagaatttt gaattgtttt tctttgcaaa 2115
accctccac aaaagcaaat cctttcaaga atggcatggg cattctgtat gaacctttcc 2175
agatggtgtt cagtgaaaga tgtgggtagt tgagaactta aaaagtgaac attgaaacat 2235
cgacgtaact ggaaaccg                                                 2253
```

Met His Arg Leu Ile Phe Val Tyr Thr Leu Ile Cys Ala Asn Phe
1               5                   10                  15

Cys Ser Cys Arg Asp Thr Ser Ala Thr Pro Gln Ser Ala Ser Ile Lys
                20                  25                  30

Ala Leu Arg Asn Ala Asn Leu Arg Arg Asp Glu Ser Asn His Leu Thr
                35                  40                  45

Asp Leu Tyr Arg Arg Asp Glu Thr Ile Gln Val Lys Gly Asn Gly Tyr
            50                  55                  60

Val Gln Ser Pro Arg Phe Pro Asn Ser Tyr Pro Arg Asn Leu Leu Leu
        65                  70                  75

Thr Trp Arg Leu His Ser Gln Glu Asn Thr Arg Ile Gln Leu Val Phe
80                  85                  90                  95

Asp Asn Gln Phe Gly Leu Glu Glu Ala Glu Asn Asp Ile Cys Arg Tyr
                100                 105                 110

Asp Phe Val Glu Val Glu Asp Ile Ser Glu Thr Ser Thr Ile Ile Arg
            115                 120                 125

Gly Arg Trp Cys Gly His Lys Glu Val Pro Pro Arg Ile Lys Ser Arg
        130                 135                 140

Thr Asn Gln Ile Lys Ile Thr Phe Lys Ser Asp Asp Tyr Phe Val Ala
    145                 150                 155

Lys Pro Gly Phe Lys Ile Tyr Tyr Ser Leu Leu Glu Asp Phe Gln Pro
160                 165                 170                 175

Ala Ala Ala Ser Glu Thr Asn Trp Glu Ser Val Thr Ser Ser Ile Ser
                180                 185                 190

Gly Val Ser Tyr Asn Ser Pro Ser Val Thr Asp Pro Thr Leu Ile Ala
            195                 200                 205

Asp Ala Leu Asp Lys Lys Ile Ala Glu Phe Asp Thr Val Glu Asp Leu
        210                 215                 220

Leu Lys Tyr Phe Asn Pro Glu Ser Trp Gln Glu Asp Leu Glu Asn Met
    225                 230                 235

```
Tyr Leu Asp Thr Pro Arg Tyr Arg Gly Arg Ser Tyr His Asp Arg Lys
240             245             250             255

Ser Lys Val Asp Leu Asp Arg Leu Asn Asp Asp Ala Lys Arg Tyr Ser
            260             265             270

Cys Thr Pro Arg Asn Tyr Ser Val Asn Ile Arg Glu Glu Leu Lys Leu
            275             280             285

Ala Asn Val Val Phe Phe Pro Arg Cys Leu Leu Val Gln Arg Cys Gly
        290             295             300

Gly Asn Cys Gly Cys Gly Thr Val Asn Trp Arg Ser Cys Thr Cys Asn
        305             310             315

Ser Gly Lys Thr Val Lys Lys Tyr His Glu Val Leu Gln Phe Glu Pro
320             325             330             335

Gly His Ile Lys Arg Arg Gly Arg Ala Lys Thr Met Ala Leu Val Asp
            340             345             350

Ile Gln Leu Asp His His Glu Arg Cys Asp Cys Ile Cys Ser Ser Arg
            355             360             365

Pro Pro Arg
        370
```

▨ Signal Sequence
▧ CUB
▦ PDGF kDa

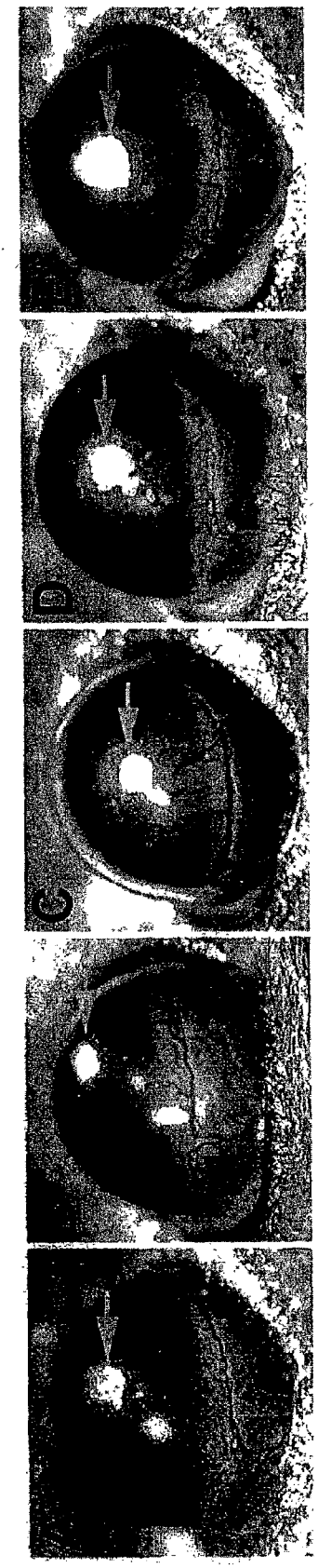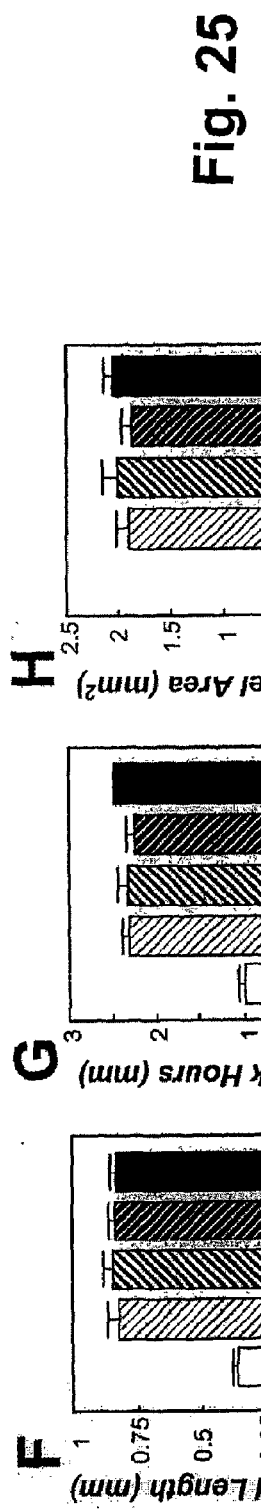
Fig. 25

SEQUENCE LISTING

<160> NUMBER OF SEQ ID NOS: 42

<210> SEQ ID NO 1
<211> LENGTH: 360
<212> TYPE: DNA
<213> ORGANISM: Homo sapiens

<400> SEQUENCE: 1

```
aattgtggct gtggaactgt caactggagg tcctgcacat gcaattcagg gaaaaccgtg      60
aaaaagtatc atgaggtatt acagtttgag cctggccaca tcaagaggag gggtagagct     120
aagaccatgg ctctagttga catccagttg gatcaccatg aacgatgtga ttgtatctgc     180
agctcaagac cacctcgata agagaatgtg cacatcctta cattaagcct gaaagaacca     240
ttagtttaag gagggtgaga taagagaccc ttttcctacc agcaaccaga cttactacta     300
gcctgcaatg caatgaacac aagtggttgc tgagtctcag ccttgctttg ttaatgccat     360
```

<210> SEQ ID NO 2
<211> LENGTH: 66
<212> TYPE: PRT
<213> ORGANISM: Homo sapiens

<400> SEQUENCE: 2

```
Asn Cys Gly Cys Gly Thr Val Asn Trp Arg Ser Cys Thr Cys Asn Ser
1               5                   10                  15

Gly Lys Thr Val Lys Lys Tyr His Glu Val Leu Gln Phe Glu Pro Gly
            20                  25                  30

His Ile Lys Arg Arg Gly Arg Ala Lys Thr Met Ala Leu Val Asp Ile
        35                  40                  45

Gln Leu Asp His His Glu Arg Cys Asp Cys Ile Cys Ser Ser Arg Pro
    50                  55                  60

Pro Arg
65
```

<210> SEQ ID NO 3
<211> LENGTH: 690

-continued

```
<212> TYPE: DNA
<213> ORGANISM: Homo sapiens

<400> SEQUENCE: 3
ggaagatttc caacccgcag cagcttcaga gaccaactgg aatctgtcac aagctctgtt      60
tcagggtatc cctataactc tccatcagta acggatccca ctctgattgc ggatgctctg     120
gacaaaaaaa ttgcagaatt tgatacagtg aagatctgc tcaagtactt caatccagag      180
tcatggcaag aagatcttga aatatgtat ctggacaccc ctcggtatcg aggcaggtca      240
taccatgacc ggaagtcaaa agttgacctg gataggctca atgatgatgc caagcgttac     300
agttgcactc ccaggaatta ctcggtcaat ataagagaag agctgaagtt ggccaatgtg     360
gtcttctttc cacgttgcct cctcgtgcag cgctgtggag gaaattgtgg ctgtggaact     420
gtcaaactgg agtcctgcac atgcaattca gggaaaaccg tgaaaaagta tcatgaggta     480
ttacagtttg agcctggcca catcaagagg aggggtagca ctaagaccat ggctctagtt     540
gacatccagt tggatcacca tgaacgatgc gattgtatct gcagctcaag accacctcga     600
taagagaatg tgcacatcct tacattaagc ctgaaagaac ctttagttta aggagggtga     660
gataagagac ccttttccta ccagcaaccc                                      690

<210> SEQ ID NO 4
<211> LENGTH: 200
<212> TYPE: PRT
<213> ORGANISM: Homo sapiens

<400> SEQUENCE: 4

Gly Arg Phe Pro Thr Arg Ser Ser Phe Arg Asp Gln Leu Glu Ser Val
1               5                   10                  15

Thr Ser Ser Val Ser Gly Tyr Pro Tyr Asn Ser Pro Ser Val Thr Asp
                20                  25                  30

Pro Thr Leu Ile Ala Asp Ala Leu Asp Lys Lys Ile Ala Glu Phe Asp
                35                  40                  45

Thr Val Glu Asp Leu Leu Lys Tyr Phe Asn Pro Glu Ser Trp Gln Glu
            50                  55                  60

Asp Leu Glu Asn Met Tyr Leu Asp Thr Pro Arg Tyr Arg Gly Arg Ser
65                  70                  75                  80

Tyr His Asp Arg Lys Ser Lys Val Asp Leu Asp Arg Leu Asn Asp Asp
                85                  90                  95

Ala Lys Arg Tyr Ser Cys Thr Pro Arg Asn Tyr Ser Val Asn Ile Arg
            100                 105                 110

Glu Glu Leu Lys Leu Ala Asn Val Val Phe Phe Pro Arg Cys Leu Leu
        115                 120                 125

Val Gln Arg Cys Gly Gly Asn Cys Gly Cys Gly Thr Val Lys Leu Glu
    130                 135                 140

Ser Cys Thr Cys Asn Ser Gly Lys Thr Val Lys Lys Tyr His Glu Val
145                 150                 155                 160

Leu Gln Phe Glu Pro Gly His Ile Lys Arg Arg Gly Arg Ala Lys Thr
                165                 170                 175

Met Ala Leu Val Asp Ile Gln Leu Asp His His Glu Arg Cys Asp Cys
            180                 185                 190

Ile Cys Ser Ser Arg Pro Pro Arg
        195                 200

<210> SEQ ID NO 5
<211> LENGTH: 1934
```

<210> TYPE: DNA
<213> ORGANISM: Homo sapiens
<220> FEATURE:
<221> NAME/KEY: CDS
<222> LOCATION: (1)..(966)
<223> OTHER INFORMATION:

<400> SEQUENCE: 5

```
ttg tac cga aga gat gag acc atc cag gtg aaa gga aac ggc tac gtg      48
Leu Tyr Arg Arg Asp Glu Thr Ile Gln Val Lys Gly Asn Gly Tyr Val
1               5                   10                  15 cag agt cct aga ttc ccg aac agc tac ccc agg aac ctg ctc ctg aca      96
Gln Ser Pro Arg Phe Pro Asn Ser Tyr Pro Arg Asn Leu Leu Leu Thr
            20                  25                  30 tgg cgg ctt cac tct cag gag aat aca cgg ata cag cta gtg ttt gac     144
Trp Arg Leu His Ser Gln Glu Asn Thr Arg Ile Gln Leu Val Phe Asp
        35                  40                  45 aat cag ttt gga tta gag gaa gca gaa aat gat atc tgt agg tat gat     192
Asn Gln Phe Gly Leu Glu Glu Ala Glu Asn Asp Ile Cys Arg Tyr Asp
    50                  55                  60 ttt gtg gaa gtt gaa gat ata tcc gaa acc agt acc att att aga gga     240
Phe Val Glu Val Glu Asp Ile Ser Glu Thr Ser Thr Ile Ile Arg Gly
65                  70                  75                  80 cga tgg tgt gga cac aag gaa gtt cct cca agg ata aaa tca aga acg     288
Arg Trp Cys Gly His Lys Glu Val Pro Pro Arg Ile Lys Ser Arg Thr
                85                  90                  95 aac caa att aaa atc aca ttc aag tcc gat gac tac ttt gtg gct aaa     336
Asn Gln Ile Lys Ile Thr Phe Lys Ser Asp Asp Tyr Phe Val Ala Lys
            100                 105                 110 cct gga ttc aag att tat tat tct ttg ctg gaa gat ttc caa ccc gca     384
Pro Gly Phe Lys Ile Tyr Tyr Ser Leu Leu Glu Asp Phe Gln Pro Ala
        115                 120                 125 gca gct tca gag acc aac tgg gaa tct gtc aca agc tct att tca ggg     432
Ala Ala Ser Glu Thr Asn Trp Glu Ser Val Thr Ser Ser Ile Ser Gly
    130                 135                 140 gta tcc tat aac tct cca tca gta acg gat ccc act ctg att gcg gat     480
Val Ser Tyr Asn Ser Pro Ser Val Thr Asp Pro Thr Leu Ile Ala Asp
145                 150                 155                 160 gct ctg gac aaa aaa att gca gaa ttt gat aca gtg gaa gat ctg ctc     528
Ala Leu Asp Lys Lys Ile Ala Glu Phe Asp Thr Val Glu Asp Leu Leu
                165                 170                 175 aag tac ttc aat cca gag tca tgg caa gaa gat ctt gag aat atg tat     576
Lys Tyr Phe Asn Pro Glu Ser Trp Gln Glu Asp Leu Glu Asn Met Tyr
            180                 185                 190 ctg gac acc cct cgg tat cga ggc agg tca tac cat gac cgg aag tca     624
Leu Asp Thr Pro Arg Tyr Arg Gly Arg Ser Tyr His Asp Arg Lys Ser
        195                 200                 205 aaa gtt gac ctg gat agg ctc aat gat gat gcc aag cgt tac agt tgc     672
Lys Val Asp Leu Asp Arg Leu Asn Asp Asp Ala Lys Arg Tyr Ser Cys
    210                 215                 220 act ccc agg aat tac tcg gtc aat ata aga gaa gag ctg aag ttg gcc     720
Thr Pro Arg Asn Tyr Ser Val Asn Ile Arg Glu Glu Leu Lys Leu Ala
225                 230                 235                 240 aat gtg gtc ttc ttt cca cgt tgc ctc ctc gtg cag cgc tgt gga gga     768
Asn Val Val Phe Phe Pro Arg Cys Leu Leu Val Gln Arg Cys Gly Gly
                245                 250                 255 aat tgt ggc tgt gga act gtc aac tgg agg tcc tgc aca tgc aat tca     816
Asn Cys Gly Cys Gly Thr Val Asn Trp Arg Ser Cys Thr Cys Asn Ser
            260                 265                 270 ggg aaa acc gtg aaa aag tat cat gag gta tta cag ttt gag cct ggc     864
Gly Lys Thr Val Lys Lys Tyr His Glu Val Leu Gln Phe Glu Pro Gly
```

-continued

```
                    275                 280                 285
cac atc aag agg agg ggt aga gct aag acc atg gct cta gtt gac atc      912
His Ile Lys Arg Arg Gly Arg Ala Lys Thr Met Ala Leu Val Asp Ile
    290                 295                 300 cag ttg gat cac cat gaa cga tgc gat tgt atc tgc agc tca aga cca      960
Gln Leu Asp His His Glu Arg Cys Asp Cys Ile Cys Ser Ser Arg Pro
305                 310                 315                 320 cct cga taagagaatg tgcacatcct tacattaagc ctgaaagaac ctttagttta      1016
Pro Arg aggagggtga gataagagac ccttttccta ccagcaacca aacttactac tagcctgcaa   1076
tgcaatgaac acaagtggtt gctgagtctc agccttgctt tgttaatgcc atggcaagta   1136
gaaaggtata tcatcaactt ctatacctaa gaatatagga ttgcatttaa taatagtgtt   1196
tgaggttata tatgcacaaa cacacacaga aatatattca tgtctatgtg tatatagatc   1256
aaatgttttt tttggtatat ataaccaggt acaccagagc ttacatatgt ttgagttaga   1316
ctcttaaaat cctttgccaa ataagggat ggtcaaatat atgaaacatg tctttagaaa   1376
atttaggaga taaatttatt tttaaatttt gaaacacaaa acaattttga atcttgctct   1436
cttaaagaaa gcatcttgta tattaaaaat caaaagatga ggctttctta catatacatc   1496
ttagttgatt attaaaaaag gaaaaaggtt tccagagaaa aggccaatac ctaagcattt   1556
tttccatgag aagcactgca tacttaccta tgtggactgt aataacctgt ctccaaaacc   1616
atgccataat aatataagtg ctttagaaat taaatcattg tgtttttat gcattttgct    1676 gaggcatcct tattcattta acacctatct caaaaactta cttagaaggt ttttattat    1736 agtcctacaa aagacaatgt ataagctgta acagaatttt gaattgtttt tctttgcaaa   1796
acccctccac aaaagcaaat cctttcaaga atggcatggg cattctgtat gaacctttcc   1856
agatggtgtt cagtgaaaga tgtgggtagt tgagaactta aaaagtgaac attgaaacat   1916
cgacgtaact ggaaaccg                                                 1934
```

<210> SEQ ID NO 6
<211> LENGTH: 322
<212> TYPE: PRT
<213> ORGANISM: Homo sapiens

<400> SEQUENCE: 6

```
Leu Tyr Arg Arg Asp Glu Thr Ile Gln Val Lys Gly Asn Gly Tyr Val
1               5                   10                  15

Gln Ser Pro Arg Phe Pro Asn Ser Tyr Pro Arg Asn Leu Leu Leu Thr
            20                  25                  30

Trp Arg Leu His Ser Gln Glu Asn Thr Arg Ile Gln Leu Val Phe Asp
        35                  40                  45

Asn Gln Phe Gly Leu Glu Glu Ala Glu Asn Asp Ile Cys Arg Tyr Asp
    50                  55                  60

Phe Val Glu Val Glu Asp Ile Ser Glu Thr Ser Thr Ile Ile Arg Gly
65                  70                  75                  80

Arg Trp Cys Gly His Lys Glu Val Pro Pro Arg Ile Lys Ser Arg Thr
                85                  90                  95

Asn Gln Ile Lys Ile Thr Phe Lys Ser Asp Asp Tyr Phe Val Ala Lys
            100                 105                 110

Pro Gly Phe Lys Ile Tyr Tyr Ser Leu Leu Glu Asp Phe Gln Pro Ala
        115                 120                 125

Ala Ala Ser Glu Thr Asn Trp Glu Ser Val Thr Ser Ser Ile Ser Gly
    130                 135                 140
```

-continued

```
Val Ser Tyr Asn Ser Pro Ser Val Thr Asp Pro Thr Leu Ile Ala Asp
145                 150                 155                 160

Ala Leu Asp Lys Lys Ile Ala Glu Phe Asp Thr Val Glu Asp Leu Leu
            165                 170                 175

Lys Tyr Phe Asn Pro Glu Ser Trp Gln Glu Asp Leu Glu Asn Met Tyr
        180                 185                 190

Leu Asp Thr Pro Arg Tyr Arg Gly Arg Ser Tyr His Asp Arg Lys Ser
    195                 200                 205

Lys Val Asp Leu Asp Arg Leu Asn Asp Asp Ala Lys Arg Tyr Ser Cys
210                 215                 220

Thr Pro Arg Asn Tyr Ser Val Asn Ile Arg Glu Glu Leu Lys Leu Ala
225                 230                 235                 240

Asn Val Val Phe Phe Pro Arg Cys Leu Leu Val Gln Arg Cys Gly Gly
                245                 250                 255

Asn Cys Gly Cys Gly Thr Val Asn Trp Arg Ser Cys Thr Cys Asn Ser
            260                 265                 270

Gly Lys Thr Val Lys Lys Tyr His Glu Val Leu Gln Phe Glu Pro Gly
        275                 280                 285

His Ile Lys Arg Arg Gly Arg Ala Lys Thr Met Ala Leu Val Asp Ile
    290                 295                 300

Gln Leu Asp His His Glu Arg Cys Asp Cys Ile Cys Ser Ser Arg Pro
305                 310                 315                 320

Pro Arg
```

<210> SEQ ID NO 7
<211> LENGTH: 2253
<212> TYPE: DNA
<213> ORGANISM: Homo sapiens
<220> FEATURE:
<221> NAME/KEY: CDS
<222> LOCATION: (176)..(1288)
<223> OTHER INFORMATION:

<400> SEQUENCE: 7

```
cgctcggaaa gttcagcatg caggaagttt ggggagagct cggcgattag cacagcgacc    60
cgggccagcg cagggcgagc gcaggcggcg agagcgcagg gcggcgcggc gtcggtcccg   120
ggagcagaac ccggcttttt cttggagcga cgctgtctct agtcgctgat ccaa atg     178
                                                                Met
                                                                1 cac cgg ctc atc ttt gtc tac act cta atc tgc gca aac ttt tgc agc     226
His Arg Leu Ile Phe Val Tyr Thr Leu Ile Cys Ala Asn Phe Cys Ser
        5                   10                  15 tgt cgg gac act tct gca acc ccg cag agc gca tcc atc aaa gct ttg     274
Cys Arg Asp Thr Ser Ala Thr Pro Gln Ser Ala Ser Ile Lys Ala Leu
        20                  25                  30 cgc aac gcc aac ctc agg cga gat gag agc aat cac ctc aca gac ttg     322
Arg Asn Ala Asn Leu Arg Arg Asp Glu Ser Asn His Leu Thr Asp Leu
    35                  40                  45 tac cga aga gat gag acc atc cag gtg aaa gga aac ggc tac gtg cag     370
Tyr Arg Arg Asp Glu Thr Ile Gln Val Lys Gly Asn Gly Tyr Val Gln
50                  55                  60                  65 agt cct aga ttc ccg aac agc tac ccc agg aac ctg ctc ctg aca tgg     418
Ser Pro Arg Phe Pro Asn Ser Tyr Pro Arg Asn Leu Leu Leu Thr Trp
                70                  75                  80 cgg ctt cac tct cag gag aat aca cgg ata cag cta gtg ttt gac aat     466
Arg Leu His Ser Gln Glu Asn Thr Arg Ile Gln Leu Val Phe Asp Asn
            85                  90                  95
```

-continued

| | |
|---|---|
| cag ttt gga tta gag gaa gca gaa aat gat atc tgt agg tat gat ttt<br>Gln Phe Gly Leu Glu Glu Ala Glu Asn Asp Ile Cys Arg Tyr Asp Phe<br>                100                   105                 110 | 514 |
| gtg gaa gtt gaa gat ata tcc gaa acc agt acc att att aga gga cga<br>Val Glu Val Glu Asp Ile Ser Glu Thr Ser Thr Ile Ile Arg Gly Arg<br>115                   120                   125 | 562 |
| tgg tgt gga cac aag gaa gtt cct cca agg ata aaa tca aga acg aac<br>Trp Cys Gly His Lys Glu Val Pro Pro Arg Ile Lys Ser Arg Thr Asn<br>130                   135                   140                 145 | 610 |
| caa att aaa atc aca ttc aag tcc gat gac tac ttt gtg gct aaa cct<br>Gln Ile Lys Ile Thr Phe Lys Ser Asp Asp Tyr Phe Val Ala Lys Pro<br>                150                   155                 160 | 658 |
| gga ttc aag att tat tat tct ttg ctg gaa gat ttc caa ccc gca gca<br>Gly Phe Lys Ile Tyr Tyr Ser Leu Leu Glu Asp Phe Gln Pro Ala Ala<br>                 165                  170                 175 | 706 |
| gct tca gag acc aac tgg gaa tct gtc aca agc tct att tca ggg gta<br>Ala Ser Glu Thr Asn Trp Glu Ser Val Thr Ser Ser Ile Ser Gly Val<br>              180                   185                   190 | 754 |
| tcc tat aac tct cca tca gta acg gat ccc act ctg att gcg gat gct<br>Ser Tyr Asn Ser Pro Ser Val Thr Asp Pro Thr Leu Ile Ala Asp Ala<br>195                   200                   205 | 802 |
| ctg gac aaa aaa att gca gaa ttt gat aca gtg gaa gat ctg ctc aag<br>Leu Asp Lys Lys Ile Ala Glu Phe Asp Thr Val Glu Asp Leu Leu Lys<br>210                   215                   220                 225 | 850 |
| tac ttc aat cca gag tca tgg caa gaa gat ctt gag aat atg tat ctg<br>Tyr Phe Asn Pro Glu Ser Trp Gln Glu Asp Leu Glu Asn Met Tyr Leu<br>                     230                   235                 240 | 898 |
| gac acc cct cgg tat cga ggc agg tca tac cat gac cgg aag tca aaa<br>Asp Thr Pro Arg Tyr Arg Gly Arg Ser Tyr His Asp Arg Lys Ser Lys<br>                245                   250                 255 | 946 |
| gtt gac ctg gat agg ctc aat gat gat gcc aag cgt tac agt tgc act<br>Val Asp Leu Asp Arg Leu Asn Asp Asp Ala Lys Arg Tyr Ser Cys Thr<br>260                   265                   270 | 994 |
| ccc agg aat tac tcg gtc aat ata aga gaa gag ctg aag ttg gcc aat<br>Pro Arg Asn Tyr Ser Val Asn Ile Arg Glu Glu Leu Lys Leu Ala Asn<br>                275                   280                 285 | 1042 |
| gtg gtc ttc ttt cca cgt tgc ctc ctc gtg cag cgc tgt gga gga aat<br>Val Val Phe Phe Pro Arg Cys Leu Leu Val Gln Arg Cys Gly Gly Asn<br>290                   295                   300                 305 | 1090 |
| tgt ggc tgt gga act gtc aac tgg agg tcc tgc aca tgc aat tca ggg<br>Cys Gly Cys Gly Thr Val Asn Trp Arg Ser Cys Thr Cys Asn Ser Gly<br>                     310                   315                 320 | 1138 |
| aaa acc gtg aaa aag tat cat gag gta tta cag ttt gag cct ggc cac<br>Lys Thr Val Lys Lys Tyr His Glu Val Leu Gln Phe Glu Pro Gly His<br>                         325                   330                 335 | 1186 |
| atc aag agg agg ggt aga gct aag acc atg gct cta gtt gac atc cag<br>Ile Lys Arg Arg Gly Arg Ala Lys Thr Met Ala Leu Val Asp Ile Gln<br>                     340                   345                 350 | 1234 |
| ttg gat cac cat gaa cga tgc gat tgt atc tgc agc tca aga cca cct<br>Leu Asp His His Glu Arg Cys Asp Cys Ile Cys Ser Ser Arg Pro Pro<br>355                   360                   365 | 1282 |
| cga taa gagaatgtgc acatccttac attaagcctg aaagaacctt tagtttaagg<br>Arg<br>370 | 1338 |
| agggtgagat aagagaccct tttcctacca gcaaccaaac ttactactag cctgcaatgc | 1398 |
| aatgaacaca gtggttgct gagtctcagc cttgctttgt taatgccatg gcaagtagaa | 1458 |
| aggtatatca tcaacttcta tacctaagaa tataggattg catttaataa tagtgtttga | 1518 |

```
ggttatatat gcacaaacac acacagaaat atattcatgt ctatgtgtat atagatcaaa   1578
tgtttttttt ggtatatata accaggtaca ccagagctta catatgtttg agttagactc   1638
ttaaaatcct ttgccaaaat aagggatggt caaatatatg aaacatgtct ttagaaaatt   1698
taggagataa atttattttt aaatttgaa acacaaaaca attttgaatc ttgctctctt    1758
aaagaaagca tcttgtatat taaaaatcaa aagatgaggc tttcttacat atacatctta   1818
gttgattatt aaaaaaggaa aaaggtttcc agagaaaagg ccaataccta agcatttttt   1878
ccatgagaag cactgcatac ttacctatgt ggactgtaat aacctgtctc caaaaccatg   1938
ccataataat ataagtgctt tagaaattaa atcattgtgt tttttatgca ttttgctgag   1998
gcatccttat tcatttaaca cctatctcaa aaacttactt agaaggtttt ttattatagt   2058
cctacaaaag acaatgtata agctgtaaca gaattttgaa ttgttttcct ttgcaaaacc   2118
cctccacaaa agcaaatcct ttcaagaatg gcatgggcat tctgtatgaa cctttccaga   2178
tggtgttcag tgaaagatgt gggtagttga gaacttaaaa agtgaacatt gaaacatcga   2238
cgtaactgga aaccg                                                   2253

<210> SEQ ID NO 8
<211> LENGTH: 370
<212> TYPE: PRT
<213> ORGANISM: Homo sapiens

<400> SEQUENCE: 8

Met His Arg Leu Ile Phe Val Tyr Thr Leu Ile Cys Ala Asn Phe Cys
1               5                  10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240
```

```
Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 9
<211> LENGTH: 4
<212> TYPE: PRT
<213> ORGANISM: Homo sapiens
<220> FEATURE:
<221> NAME/KEY: misc_feature
<223> OTHER INFORMATION: A putative proteolytic site found at residues
      255-258 of SEQ ID NO:8 (PDGF-D)

<400> SEQUENCE: 9

Arg Lys Ser Lys
1

<210> SEQ ID NO 10
<211> LENGTH: 91
<212> TYPE: PRT
<213> ORGANISM: Homo sapiens
<220> FEATURE:
<221> NAME/KEY: misc_feature
<223> OTHER INFORMATION: PDGF/VEGF-homology domain of PDGF-D

<400> SEQUENCE: 10

Cys Thr Pro Arg Asn Tyr Ser Val Asn Ile Arg Glu Glu Leu Lys Leu
1               5                   10                  15

Ala Asn Val Val Phe Phe Pro Arg Cys Leu Leu Val Gln Arg Cys Gly
            20                  25                  30

Gly Asn Cys Gly Cys Gly Thr Val Lys Leu Glu Ser Cys Thr Cys Asn
        35                  40                  45

Ser Gly Lys Thr Val Lys Lys Tyr His Glu Val Leu Gln Phe Glu Pro
    50                  55                  60

Gly His Ile Lys Arg Arg Gly Arg Ala Lys Thr Met Ala Leu Val Asp
65                  70                  75                  80

Ile Gln Leu Asp His His Glu Arg Cys Asp Cys
                85                  90

<210> SEQ ID NO 11
<211> LENGTH: 88
<212> TYPE: PRT
<213> ORGANISM: Homo sapiens
<220> FEATURE:
<221> NAME/KEY: misc_feature
<223> OTHER INFORMATION: PDGF/VEGF-homology domain of PDGF-C
```

```
<400> SEQUENCE: 11

Cys Thr Pro Arg Asn Phe Ser Val Ser Ile Arg Glu Glu Leu Lys Arg
1               5                   10                  15

Thr Asp Thr Ile Phe Trp Pro Gly Cys Leu Leu Val Lys Arg Cys Gly
            20                  25                  30

Gly Asn Cys Ala Cys Cys Leu His Asn Cys Asn Glu Cys Gln Cys Val
        35                  40                  45

Pro Ser Lys Val Thr Lys Lys Tyr His Glu Val Leu Gln Leu Arg Pro
    50                  55                  60

Lys Thr Gly Val Arg Gly Leu His Lys Ser Leu Thr Asp Val Ala Leu
65                  70                  75                  80

Glu His His Glu Glu Cys Asp Cys
                85

<210> SEQ ID NO 12
<211> LENGTH: 84
<212> TYPE: PRT
<213> ORGANISM: Homo sapiens
<220> FEATURE:
<221> NAME/KEY: misc_feature
<223> OTHER INFORMATION: PDGF/VEGF-homology domain of PDGF-A

<400> SEQUENCE: 12

Cys Lys Thr Arg Thr Val Ile Tyr Glu Ile Pro Arg Ser Gln Val Asp
1               5                   10                  15

Pro Thr Ser Ala Asn Phe Leu Ile Trp Pro Pro Cys Val Glu Val Lys
            20                  25                  30

Arg Cys Thr Gly Cys Cys Asn Thr Ser Ser Val Lys Cys Gln Pro Ser
        35                  40                  45

Arg Val His His Arg Ser Val Lys Val Ala Lys Val Glu Tyr Val Arg
    50                  55                  60

Lys Lys Pro Lys Leu Lys Glu Val Gln Val Arg Leu Glu Glu His Leu
65                  70                  75                  80

Glu Cys Ala Cys

<210> SEQ ID NO 13
<211> LENGTH: 84
<212> TYPE: PRT
<213> ORGANISM: Homo sapiens
<220> FEATURE:
<221> NAME/KEY: misc_feature
<223> OTHER INFORMATION: PDGF/VEGF-homology domain of PDGF-B

<400> SEQUENCE: 13

Cys Lys Thr Arg Thr Glu Val Phe Glu Ile Ser Arg Arg Leu Ile Asp
1               5                   10                  15

Arg Thr Asn Ala Asn Phe Leu Val Trp Pro Pro Cys Val Glu Val Gln
            20                  25                  30

Arg Cys Ser Gly Cys Cys Asn Asn Arg Asn Val Gln Cys Arg Pro Thr
        35                  40                  45

Gln Val Gln Leu Arg Pro Val Gln Val Arg Lys Ile Glu Ile Val Arg
    50                  55                  60

Lys Lys Pro Ile Phe Lys Lys Ala Thr Val Thr Leu Glu Asp His Leu
65                  70                  75                  80

Ala Cys Lys Cys

<210> SEQ ID NO 14
```

```
<211> LENGTH: 79
<212> TYPE: PRT
<213> ORGANISM: Homo sapiens
<220> FEATURE:
<221> NAME/KEY: misc_feature
<223> OTHER INFORMATION: PDGF/VEGF-homology domain of VEGF-165

<400> SEQUENCE: 14

Cys His Pro Ile Glu Thr Leu Val Asp Ile Phe Gln Glu Tyr Pro Asp
1               5                   10                  15

Glu Ile Glu Tyr Ile Phe Lys Pro Ser Cys Val Pro Leu Met Arg Cys
            20                  25                  30

Gly Gly Cys Cys Asn Asp Glu Gly Leu Glu Cys Val Pro Thr Glu Glu
        35                  40                  45

Ser Asn Ile Thr Met Gln Ile Met Arg Ile Lys Pro His Gln Gly Gln
50                  55                  60

His Ile Gly Glu Met Ser Phe Leu Gln His Asn Lys Cys Glu Cys
65                  70                  75

<210> SEQ ID NO 15
<211> LENGTH: 79
<212> TYPE: PRT
<213> ORGANISM: Homo sapiens
<220> FEATURE:
<221> NAME/KEY: misc_feature
<223> OTHER INFORMATION: PDGF/VEGF-homology domain of PlGF-2

<400> SEQUENCE: 15

Cys Arg Ala Leu Glu Arg Leu Val Asp Val Val Ser Glu Tyr Pro Ser
1               5                   10                  15

Glu Val Glu His Met Phe Ser Pro Ser Cys Val Ser Leu Leu Arg Cys
            20                  25                  30

Thr Gly Cys Cys Gly Asp Glu Asp Leu His Cys Val Pro Val Glu Thr
        35                  40                  45

Ala Asn Val Thr Met Gln Leu Leu Lys Ile Arg Ser Gly Asp Arg Pro
50                  55                  60

Ser Tyr Val Glu Leu Thr Phe Ser Gln His Val Arg Cys Glu Cys
65                  70                  75

<210> SEQ ID NO 16
<211> LENGTH: 78
<212> TYPE: PRT
<213> ORGANISM: Homo sapiens
<220> FEATURE:
<221> NAME/KEY: misc_feature
<223> OTHER INFORMATION: PDGF/VEGF-homology domain of VEGF-B167

<400> SEQUENCE: 16

Cys Gln Pro Arg Glu Val Val Val Pro Leu Thr Val Glu Leu Met Gly
1               5                   10                  15

Thr Val Ala Lys Gln Leu Val Pro Ser Cys Val Thr Val Gln Arg Cys
            20                  25                  30

Gly Gly Cys Cys Pro Asp Asp Gly Leu Glu Cys Val Pro Thr Gly Gln
        35                  40                  45

His Gln Val Arg Met Gln Ile Leu Met Ile Arg Tyr Pro Ser Ser Gln
50                  55                  60

Leu Gly Glu Met Ser Leu Glu Glu His Ser Gln Cys Glu Cys
65                  70                  75

<210> SEQ ID NO 17
<211> LENGTH: 81
```

```
<212> TYPE: PRT
<213> ORGANISM: Homo sapiens
<220> FEATURE:
<221> NAME/KEY: misc_feature
<223> OTHER INFORMATION: PDGF/VEGF-homology domain of VEGF-C

<400> SEQUENCE: 17

Cys Met Pro Arg Glu Val Cys Ile Asp Val Gly Lys Glu Phe Gly Val
1               5                   10                  15

Ala Thr Asn Thr Phe Phe Lys Pro Pro Cys Val Ser Val Tyr Arg Cys
                20                  25                  30

Gly Gly Cys Cys Asn Ser Glu Gly Leu Gln Cys Met Asn Thr Ser Thr
            35                  40                  45

Ser Tyr Leu Ser Lys Thr Leu Phe Glu Ile Thr Val Pro Leu Ser Gln
        50                  55                  60

Gly Pro Lys Pro Val Thr Ile Ser Phe Ala Asn His Thr Ser Cys Arg
65                  70                  75                  80

Cys

<210> SEQ ID NO 18
<211> LENGTH: 81
<212> TYPE: PRT
<213> ORGANISM: Homo sapiens
<220> FEATURE:
<221> NAME/KEY: misc_feature
<223> OTHER INFORMATION: PDGF/VEGF-homology domain of VEGF-D

<400> SEQUENCE: 18

Cys Ser Pro Arg Glu Thr Cys Val Glu Val Ala Ser Glu Leu Gly Lys
1               5                   10                  15

Thr Thr Asn Thr Phe Phe Lys Pro Pro Cys Val Asn Val Phe Arg Cys
                20                  25                  30

Gly Gly Cys Cys Asn Glu Glu Gly Val Met Cys Met Asn Thr Ser Thr
            35                  40                  45

Ser Tyr Ile Ser Lys Gln Leu Phe Glu Ile Ser Val Pro Leu Thr Ser
        50                  55                  60

Val Pro Glu Leu Val Pro Val Lys Ile Ala Asn His Thr Gly Cys Lys
65                  70                  75                  80

Cys

<210> SEQ ID NO 19
<211> LENGTH: 118
<212> TYPE: PRT
<213> ORGANISM: Homo sapiens
<220> FEATURE:
<221> NAME/KEY: misc_feature
<223> OTHER INFORMATION: CUB domain of PDGF-D

<400> SEQUENCE: 19

Asp Glu Thr Ile Gln Val Lys Gly Asn Gly Tyr Val Gln Ser Pro Arg
1               5                   10                  15

Phe Pro Asn Ser Tyr Pro Arg Asn Leu Leu Leu Thr Trp Arg Leu His
                20                  25                  30

Ser Gln Glu Asn Thr Arg Ile Gln Leu Val Phe Asp Asn Gln Phe Gly
            35                  40                  45

Leu Glu Glu Ala Glu Asn Asp Ile Cys Arg Tyr Asp Phe Val Glu Val
        50                  55                  60

Glu Asp Ile Ser Glu Thr Ser Thr Ile Ile Arg Gly Arg Trp Cys Gly
65                  70                  75                  80
```

```
His Lys Glu Val Pro Pro Arg Ile Lys Ser Arg Thr Asn Gln Ile Lys
                85                  90                  95

Ile Thr Phe Lys Ser Asp Asp Tyr Phe Val Ala Lys Pro Gly Phe Lys
            100                 105                 110

Ile Tyr Tyr Ser Leu Leu
        115

<210> SEQ ID NO 20
<211> LENGTH: 113
<212> TYPE: PRT
<213> ORGANISM: Homo sapiens
<220> FEATURE:
<221> NAME/KEY: misc_feature
<223> OTHER INFORMATION: CUB domain 1 of BMP-1

<400> SEQUENCE: 20

Cys Gly Glu Thr Leu Gln Asp Ser Thr Gly Asn Phe Ser Ser Pro Glu
1               5                   10                  15

Tyr Pro Asn Gly Tyr Ser Ala His Met His Cys Val Trp Arg Ile Ser
            20                  25                  30

Val Thr Pro Gly Glu Lys Ile Ile Leu Asn Phe Thr Ser Leu Asp Leu
        35                  40                  45

Tyr Arg Ser Arg Leu Cys Trp Tyr Asp Tyr Val Glu Val Arg Asp Gly
    50                  55                  60

Phe Trp Arg Lys Ala Pro Leu Arg Gly Arg Phe Cys Gly Ser Lys Leu
65                  70                  75                  80

Pro Glu Pro Ile Val Ser Thr Asp Ser Arg Leu Trp Val Glu Phe Arg
            85                  90                  95

Ser Ser Ser Asn Trp Val Gly Lys Gly Phe Phe Ala Val Tyr Glu Ala
            100                 105                 110

Ile

<210> SEQ ID NO 21
<211> LENGTH: 112
<212> TYPE: PRT
<213> ORGANISM: Homo sapiens
<220> FEATURE:
<221> NAME/KEY: misc_feature
<223> OTHER INFORMATION: CUB domain 2 of BMP-1

<400> SEQUENCE: 21

Cys Gly Gly Asp Val Lys Lys Asp Tyr Gly His Ile Gln Ser Pro Asn
1               5                   10                  15

Tyr Pro Asp Asp Tyr Arg Pro Ser Lys Val Cys Ile Trp Arg Ile Gln
            20                  25                  30

Val Ser Glu Gly Phe His Val Gly Leu Thr Phe Gln Ser Phe Glu Ile
        35                  40                  45

Glu Arg His Asp Ser Cys Ala Tyr Asp Tyr Leu Glu Val Arg Asp Gly
    50                  55                  60

His Ser Glu Ser Ser Thr Leu Ile Gly Arg Tyr Cys Gly Tyr Glu Lys
65                  70                  75                  80

Pro Asp Asp Ile Lys Ser Thr Ser Ser Arg Leu Trp Leu Lys Phe Val
            85                  90                  95

Ser Asp Gly Ser Ile Asn Lys Ala Gly Phe Ala Val Asn Phe Phe Lys
            100                 105                 110

<210> SEQ ID NO 22
<211> LENGTH: 113
<212> TYPE: PRT
```

<210> SEQ ID NO 22
<211> LENGTH: 113
<212> TYPE: PRT
<213> ORGANISM: Homo sapiens
<220> FEATURE:
<221> NAME/KEY: misc_feature
<223> OTHER INFORMATION: CUB domain 3 of BMP-1

<400> SEQUENCE: 22

```
Cys Gly Gly Phe Leu Thr Lys Leu Asn Gly Ser Ile Thr Ser Pro Gly
1               5                   10                  15

Trp Pro Lys Glu Tyr Pro Pro Asn Lys Asn Cys Ile Trp Gln Leu Val
                20                  25                  30

Ala Pro Thr Gln Tyr Arg Ile Ser Leu Gln Phe Asp Phe Phe Glu Thr
            35                  40                  45

Glu Gly Asn Asp Val Cys Lys Tyr Asp Phe Val Glu Val Arg Ser Gly
    50                  55                  60

Leu Thr Ala Asp Ser Lys Leu His Gly Lys Phe Cys Gly Ser Glu Lys
65                  70                  75                  80

Pro Glu Val Ile Thr Ser Gln Tyr Asn Met Arg Val Glu Pro Lys
                85                  90                  95

Ser Asp Asn Thr Val Ser Lys Lys Gly Phe Lys Ala His Phe Phe Ser
                100                 105                 110

Glu
```

<210> SEQ ID NO 23
<211> LENGTH: 113
<212> TYPE: PRT
<213> ORGANISM: Homo sapiens
<220> FEATURE:
<221> NAME/KEY: misc_feature
<223> OTHER INFORMATION: CUB domain 1 of Neuropilin

<400> SEQUENCE: 23

```
Gly Asp Thr Ile Lys Ile Glu Ser Pro Gly Tyr Leu Thr Ser Pro Gly
1               5                   10                  15

Tyr Pro His Ser Tyr His Pro Ser Glu Lys Cys Glu Trp Leu Ile Gln
                20                  25                  30

Ala Pro Asp Pro Tyr Gln Arg Ile Met Ile Asn Phe Asn Pro His Phe
            35                  40                  45

Asp Leu Glu Asp Arg Asp Cys Lys Tyr Asp Tyr Val Glu Val Phe Asp
    50                  55                  60

Gly Glu Asn Glu Asn Gly His Phe Arg Gly Lys Phe Cys Gly Lys Ile
65                  70                  75                  80

Ala Pro Pro Pro Val Val Ser Ser Gly Pro Phe Leu Phe Ile Lys Phe
                85                  90                  95

Val Ser Asp Tyr Glu Thr His Gly Ala Gly Phe Ser Ile Arg Tyr Glu
                100                 105                 110

Ile
```

<210> SEQ ID NO 24
<211> LENGTH: 119
<212> TYPE: PRT
<213> ORGANISM: Homo sapiens
<220> FEATURE:
<221> NAME/KEY: misc_feature
<223> OTHER INFORMATION: CUB domain 2 of Neuropilin

<400> SEQUENCE: 24

```
Cys Ser Gln Asn Tyr Thr Thr Pro Ser Gly Val Ile Lys Ser Pro Gly
1               5                   10                  15

Phe Pro Glu Lys Tyr Pro Asn Ser Leu Glu Cys Thr Tyr Ile Val Phe
```

-continued

```
                    20                  25                  30
Ala Pro Lys Met Ser Glu Ile Ile Leu Glu Phe Glu Ser Phe Asp Leu
        35                  40                  45

Glu Pro Asp Ser Asn Pro Pro Gly Gly Met Phe Cys Arg Tyr Asp Arg
 50                  55                  60

Leu Glu Ile Trp Asp Gly Phe Pro Asp Val Gly Pro His Ile Gly Arg
 65                  70                  75                  80

Tyr Cys Gly Gln Lys Thr Pro Gly Arg Ile Arg Ser Ser Ser Gly Ile
                85                  90                  95

Leu Ser Met Val Phe Tyr Thr Asp Ser Ala Ile Ala Lys Glu Gly Phe
            100                 105                 110

Ser Ala Asn Tyr Ser Val Leu
        115

<210> SEQ ID NO 25
<211> LENGTH: 15
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: can be any amino acid residue
<220> FEATURE:
<221> NAME/KEY: MISC_FEATURE
<222> LOCATION: (7)..(7)
<223> OTHER INFORMATION: can be any amino acid residue

<400> SEQUENCE: 25

Pro Xaa Cys Leu Leu Val Xaa Arg Cys Gly Gly Asn Cys Gly Cys
 1               5                  10                  15

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Forward PCR
      primer used to amplify a 327 bp DNA fragment from a human fetal
      lung cDNA library

<400> SEQUENCE: 26
gtcgtggaac tgtcaactgg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Reverse PCR
      primer used to amplify a 327 bp DNA fragment from a human fetal
      lung cDNA library

<400> SEQUENCE: 27
ctcagcaacc acttgtgttc                                              20

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:  Adaptor
      primer 1 (Clontech) used to amplify the sequence found at the 5'
      end of PDGF-D

<400> SEQUENCE: 28
```

```
ccatcctaat acgactcact atagggc                                              27
```

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:  Adaptor
      primer 2 (Clontech) used to amplify the sequence found at the 5'
      end of PDGF-D

<400> SEQUENCE: 29

```
agtgggatcc gttactgatg gagagttat                                            29
```

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Forward PCR
      primer used to amplify a 429 bp DNA fragment (nucleotides 556 to
      966 of SEQ ID NO:5) of PDGF-D

<400> SEQUENCE: 30

```
cccaagcttg aagatcttga gaatat                                               26
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Reverse PCR
      primer used to amplify a 429 bp DNA fragment (nucleotides 556 to
      966 of SEQ ID NO:5) of PDGF-D

<400> SEQUENCE: 31

```
tgctctagat cgaggtggtc tt                                                   22
```

<210> SEQ ID NO 32
<211> LENGTH: 345
<212> TYPE: PRT
<213> ORGANISM: Homo sapiens
<220> FEATURE:
<221> NAME/KEY: misc_feature
<223> OTHER INFORMATION: Amino acid sequence for PDGF-C

<400> SEQUENCE: 32

Met Ser Leu Phe Gly Leu Leu Leu Val Thr Ser Ala Leu Ala Gly Gln
1               5                   10                  15

Arg Arg Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

```
Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
                180                 185                 190

Phe Ser Thr Leu Glu Asp Leu Ile Arg Tyr Leu Glu Pro Glu Arg Trp
            195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
                260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
                340                 345

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Forward PCR
      primer for the cDNA encoding amino acid residues 24-370 of SEQ ID
      NO:8 (PDGF-D)
<220> FEATURE:
<221> NAME/KEY: misc_feature
<223> OTHER INFORMATION: Primer includes a XbaI site for in frame
      cloning

<400> SEQUENCE: 33
gatatctaga agcaaccccg cagagc                                          26

<210> SEQ ID NO 34
<211> LENGTH: 46
<212> TYPE: DNA
<213> ORGANISM: Artificial Sequence
<220> FEATURE:
<223> OTHER INFORMATION: Description of Artificial Sequence: Reverse PCR
      primer for amplication of the cDNA encoding amino acid residues
      24-370 of SEQ ID NO:8 (PDGF-D)
<220> FEATURE:
<221> NAME/KEY: misc_feature
<223> OTHER INFORMATION: Primer includes an EcoRI site and sequences
      encoding for a C-terminal 6X His tag preceded by an enterokinase
      site

<400> SEQUENCE: 34
gctcgaattc taaatggtga tggtgatgat gtcgaggtgg tcttga                    46
```

<210> SEQ ID NO 35
<211> LENGTH: 1252
<212> TYPE: DNA
<213> ORGANISM: Murinae gen. sp.

<400> SEQUENCE: 35

| | | | | | |
|---|---|---|---|---|---|
| atgcaacggc | tcgttttagt | ctccattctc | ctgtgcgcga | actttagctg | ctatccggac | 60 |
| acttttgcga | ctccgcagag | agcatccatc | aaagctttgc | gcaatgccaa | cctcaggaga | 120 |
| gatgagagca | atcacctcac | agacttgtac | cagagagagg | agaacattca | ggtgacaagc | 180 |
| aatggccatg | tgcagagtcc | tcgcttcccg | aacagctacc | caaggaacct | gcttctgaca | 240 |
| tggtggctcc | gttcccagga | gaaaacacgg | atacaactgt | cctttgacca | tcaattcgga | 300 |
| ctagaggaag | cagaaaatga | catttgtagg | tatgactttg | tggaagttga | agaagtctca | 360 |
| gagagcagca | ctgttgtcag | aggaagatgg | tgtggccaca | aggagatccc | tccaaggata | 420 |
| acgtcaagaa | caaaccagat | taaaatcaca | tttaagtctg | atgactactt | tgtggcaaaa | 480 |
| cctggattca | agatttatta | ttcatttgtg | aagatttcc | aaccggaagc | agcctcagag | 540 |
| accaactggg | aatcagtcac | aagctctttc | tctggggtgt | cctatcactc | tccatcaata | 600 |
| acggaccca | ctctcactgc | tgatgccctg | acaaaactg | tcgcagaatt | cgataccgtg | 660 |
| gaagatctac | ttaagcactt | caatccagtg | tcttggcaag | atgatctgga | gaatttgtat | 720 |
| ctggacaccc | ctcattatag | aggcaggtca | taccatgatc | ggaagtccaa | agtggacctg | 780 |
| gacaggctca | atgatgatgt | caagcgttac | agttgcactc | ccaggaatca | ctctgtgaac | 840 |
| ctcagggagg | agctgaagct | gaccaatgca | gtcttcttcc | cacgatgcct | cctcgtgcag | 900 |
| cgctgtggtg | gcaactgtgg | ttgcggaact | gtcaactgga | agtcctgcac | atgcagctca | 960 |
| gggaagacag | tgaagaagta | tcatgaggta | ttgaagtttg | agcctggaca | tttcaagaga | 1020 |
| aggggcaaag | ctaagaatat | ggctcttgtt | gatatccagc | tggatcatca | tgagcgatgt | 1080 |
| gactgtatct | gcagctcaag | accacctcga | taaaacacta | tgcacatctg | tactttgatt | 1140 |
| atgaaaggac | ctttaggtta | caaaaaccct | aagaagcttc | taatctcagt | gcaatgaatg | 1200 |
| catatggaaa | tgttgctttg | ttagtgccat | ggcaagaaga | agcaaatatc | at | 1252 |

<210> SEQ ID NO 36
<211> LENGTH: 370
<212> TYPE: PRT
<213> ORGANISM: Murinae gen. sp.

<400> SEQUENCE: 36

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
                20                  25                  30

Leu Arg Asn Ala Asn Leu Arg Arg Asp Glu Ser Asn His Leu Thr Asp
            35                  40                  45

Leu Tyr Gln Arg Glu Glu Asn Ile Gln Val Thr Ser Asn Gly His Val
        50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95

His Gln Phe Gly Leu Glu Glu Ala Glu Asn Asp Ile Cys Arg Tyr Asp
                100                 105                 110

```
Phe Val Glu Val Glu Val Ser Glu Ser Ser Thr Val Val Arg Gly
        115                 120                 125
Arg Trp Cys Gly His Lys Glu Ile Pro Pro Arg Ile Thr Ser Arg Thr
130                 135                 140
Asn Gln Ile Lys Ile Thr Phe Lys Ser Asp Asp Tyr Phe Val Ala Lys
145                 150                 155                 160
Pro Gly Phe Lys Ile Tyr Tyr Ser Phe Val Glu Asp Phe Gln Pro Glu
                165                 170                 175
Ala Ala Ser Glu Thr Asn Trp Glu Ser Val Thr Ser Ser Phe Ser Gly
            180                 185                 190
Val Ser Tyr His Ser Pro Ser Ile Thr Asp Pro Thr Leu Thr Ala Asp
        195                 200                 205
Ala Leu Asp Lys Thr Val Ala Glu Phe Asp Thr Val Glu Asp Leu Leu
210                 215                 220
Lys His Phe Asn Pro Val Ser Trp Gln Asp Asp Leu Glu Asn Leu Tyr
225                 230                 235                 240
Leu Asp Thr Pro His Tyr Arg Gly Arg Ser Tyr His Asp Arg Lys Ser
                245                 250                 255
Lys Val Asp Leu Asp Arg Leu Asn Asp Asp Val Lys Arg Tyr Ser Cys
            260                 265                 270
Thr Pro Arg Asn His Ser Val Asn Leu Arg Glu Glu Leu Lys Leu Thr
        275                 280                 285
Asn Ala Val Phe Phe Pro Arg Cys Leu Leu Val Gln Arg Cys Gly Gly
290                 295                 300
Asn Cys Gly Cys Gly Thr Val Asn Trp Lys Ser Cys Thr Cys Ser Ser
305                 310                 315                 320
Gly Lys Thr Val Lys Lys Tyr His Glu Val Leu Lys Phe Glu Pro Gly
                325                 330                 335
His Phe Lys Arg Arg Gly Lys Ala Lys Asn Met Ala Leu Val Asp Ile
            340                 345                 350
Gln Leu Asp His His Glu Arg Cys Asp Cys Ile Cys Ser Ser Arg Pro
        355                 360                 365
Pro Arg
   370

<210> SEQ ID NO 37
<211> LENGTH: 1234
<212> TYPE: DNA
<213> ORGANISM: Murinae gen. sp.

<400> SEQUENCE: 37
atgcaacggc tcgttttagt ctccattctc ctgtgcgcga actttagctg ctatccggac      60
acttttgcga ctccgcagag agcatccatc aaagctttgc gcaatgccaa cctcaggaga     120
gatgacttgt accagagaga ggagaacatt caggtgacaa gcaatggcca tgtgcagagt     180
cctcgcttcc cgaacagcta cccaaggaac ctgcttctga catggtggct ccgttcccag     240
gagaaaacac ggatacaact gtcctttgac catcaattcg gactagagga agcagaaaat     300
gacatttgta ggtatgactt tgtggaagtt gaagaagtct cagagagcag cactgttgtc     360
agaggaagat ggtgtggcca caaggagatc cctccaagga taacgtcaag aacaaaccag     420
attaaaatca catttaagtc tgatgactac tttgtggcaa acctggattc aagatttat      480 tattcatttg tggaagattt ccaaccggaa gcagcctcag agaccaactg ggaatcagtc     540
acaagctctt tctctggggt gtcctatcac tctccatcaa taacggaccc cactctcact     600
```

```
gctgatgccc tggacaaaac tgtcgcagaa ttcgataccg tggaagatct acttaagcac   660
ttcaatccag tgtcttggca agatgatctg gagaatttgt atctggacac ccctcattat   720
agaggcaggt cataccatga tcggaagtcc aaagtggacc tggacaggct caatgatgat   780
gtcaagcgtt acagttgcac tcccaggaat cactctgtga acctcaggga ggagctgaag   840
ctgaccaatg cagtcttctt cccacgatgc ctcctcgtgc agcgctgtgg tggcaactgt   900
ggttgcggaa ctgtcaactg gaagtcctgc acatgcagct cagggaagac agtgaagaag   960
tatcatgagg tattgaagtt tgagcctgga catttcaaga aaggggcaa agctaagaat  1020 atggctcttg ttgatatcca gctggatcat catgagcgat gtgactgtat ctgcagctca  1080
agaccacctc gataaaacac tatgcacatc tgtactttga ttatgaaagg acctttaggt  1140
tacaaaaacc ctaagaagct tctaatctca gtgcaatgaa tgcatatgga aatgttgctt  1200
tgttagtgcc atggcaagaa gaagcaaata tcat                              1234
```

<210> SEQ ID NO 38
<211> LENGTH: 364
<212> TYPE: PRT
<213> ORGANISM: Murinae gen. sp.

<400> SEQUENCE: 38

```
Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Asp Leu Tyr Gln Arg Glu Glu
        35                  40                  45

Asn Ile Gln Val Thr Ser Asn Gly His Val Gln Ser Pro Arg Phe Pro
    50                  55                  60

Asn Ser Tyr Pro Arg Asn Leu Leu Leu Thr Trp Trp Leu Arg Ser Gln
65                  70                  75                  80

Glu Lys Thr Arg Ile Gln Leu Ser Phe Asp His Gln Phe Gly Leu Glu
                85                  90                  95

Glu Ala Glu Asn Asp Ile Cys Arg Tyr Asp Phe Val Glu Val Glu Glu
            100                 105                 110

Val Ser Glu Ser Ser Thr Val Val Arg Gly Arg Trp Cys Gly His Lys
        115                 120                 125

Glu Ile Pro Pro Arg Ile Thr Ser Arg Thr Asn Gln Ile Lys Ile Thr
    130                 135                 140

Phe Lys Ser Asp Asp Tyr Phe Val Ala Lys Pro Gly Phe Lys Ile Tyr
145                 150                 155                 160

Tyr Ser Phe Val Glu Asp Phe Gln Pro Glu Ala Ala Ser Glu Thr Asn
                165                 170                 175

Trp Glu Ser Val Thr Ser Ser Phe Ser Gly Val Ser Tyr His Ser Pro
            180                 185                 190

Ser Ile Thr Asp Pro Thr Leu Thr Ala Asp Ala Leu Asp Lys Thr Val
        195                 200                 205

Ala Glu Phe Asp Thr Val Glu Asp Leu Leu Lys His Phe Asn Pro Val
    210                 215                 220

Ser Trp Gln Asp Leu Glu Asn Leu Tyr Leu Asp Thr Pro His Tyr
225                 230                 235                 240

Arg Gly Arg Ser Tyr His Asp Arg Lys Ser Lys Val Asp Leu Asp Arg
                245                 250                 255

Leu Asn Asp Asp Val Lys Arg Tyr Ser Cys Thr Pro Arg Asn His Ser
```

```
             260                 265                 270
Val Asn Leu Arg Glu Glu Leu Lys Leu Thr Asn Ala Val Phe Phe Pro
            275                 280                 285

Arg Cys Leu Leu Val Gln Arg Cys Gly Gly Asn Cys Gly Cys Gly Thr
            290                 295                 300

Val Asn Trp Lys Ser Cys Thr Cys Ser Ser Gly Lys Thr Val Lys Lys
305                 310                 315                 320

Tyr His Glu Val Leu Lys Phe Glu Pro Gly His Phe Lys Arg Arg Gly
                325                 330                 335

Lys Ala Lys Asn Met Ala Leu Val Asp Ile Gln Leu Asp His His Glu
            340                 345                 350

Arg Cys Asp Cys Ile Cys Ser Ser Arg Pro Pro Arg
            355                 360

<210> SEQ ID NO 39
<211> LENGTH: 768
<212> TYPE: DNA
<213> ORGANISM: Murinae gen. sp.

<400> SEQUENCE: 39
atgcaacggc tcgttttagt ctccattctc ctgtgcgcga actttagctg ctatccggac        60
acttttgcga ctccgcagag agcatccatc aaagctttgc gcaatgccaa cctcaggaga       120
gatgacttgt accagagaga ggagaacatt caggtgacaa gcaatggcca tgtgcagagt       180
cctcgcttcc cgaacagcta cccaaggaac ctgcttctga catggtggct ccgttcccag       240
gagaaaacac ggatacaact gtcctttgac atcaattcg gactagagga agcagaaaat       300
gacatttgta ggtatgactt tgtggaagtt gaagaagtct cagagagcag cactgttgtc       360
agaggaagat ggtgtggcca aaggagatc cctccaagga taacgtcaag aacaaaccag       420
attaaaatca catttaagtc tgatgactac tttgtggcaa aacctggatt caagatttat       480
tattcatttg tggaagattt ccaaccggaa gcagcctcag agaccaactg ggaatcagtc       540
acaagctctt tctctggggt gtcctatcac tctccatcaa taacgaccc cactctcact       600 gctgatgccc tggacaaaac tgtcgcagaa ttcgataccg tggaagatct acttaagcac       660
ttcaatccag tgtcttggca agatgatctg gagaatttgt atctggacac ccctcattat       720
agaggcaggt cataccatga tcggaagtcc aaaggtattg aagtttga                   768

<210> SEQ ID NO 40
<211> LENGTH: 255
<212> TYPE: PRT
<213> ORGANISM: Murinae gen. sp.

<400> SEQUENCE: 40

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
                20                  25                  30

Leu Arg Asn Ala Asn Leu Arg Arg Asp Asp Leu Tyr Gln Arg Glu Glu
            35                  40                  45

Asn Ile Gln Val Thr Ser Asn Gly His Val Gln Ser Pro Arg Phe Pro
        50                  55                  60

Asn Ser Tyr Pro Arg Asn Leu Leu Leu Thr Trp Trp Leu Arg Ser Gln
65                  70                  75                  80

Glu Lys Thr Arg Ile Gln Leu Ser Phe Asp His Gln Phe Gly Leu Glu
                85                  90                  95
```

-continued

```
Glu Ala Glu Asn Asp Ile Cys Arg Tyr Asp Phe Val Glu Val Glu Glu
                100                 105                 110

Val Ser Glu Ser Ser Thr Val Val Arg Gly Arg Trp Cys Gly His Lys
            115                 120                 125

Glu Ile Pro Pro Arg Ile Thr Ser Arg Thr Asn Gln Ile Lys Ile Thr
            130                 135                 140

Phe Lys Ser Asp Asp Tyr Phe Val Ala Lys Pro Gly Phe Lys Ile Tyr
145                 150                 155                 160

Tyr Ser Phe Val Glu Asp Phe Gln Pro Glu Ala Ala Ser Glu Thr Asn
                165                 170                 175

Trp Glu Ser Val Thr Ser Ser Phe Ser Gly Val Ser Tyr His Ser Pro
                180                 185                 190

Ser Ile Thr Asp Pro Thr Leu Thr Ala Asp Ala Leu Asp Lys Thr Val
                195                 200                 205

Ala Glu Phe Asp Thr Val Glu Asp Leu Leu Lys His Phe Asn Pro Val
            210                 215                 220

Ser Trp Gln Asp Asp Leu Glu Asn Leu Tyr Leu Asp Thr Pro His Tyr
225                 230                 235                 240

Arg Gly Arg Ser Tyr His Asp Arg Lys Ser Lys Gly Ile Glu Val
                245                 250                 255

<210> SEQ ID NO 41
<211> LENGTH: 19
<212> TYPE: DNA
<213> ORGANISM: Murinae gen. sp.

<400> SEQUENCE: 41
caaatgcaac ggctcgttt                                                19

<210> SEQ ID NO 42
<211> LENGTH: 24
<212> TYPE: DNA
<213> ORGANISM: Murinae gen. sp.

<400> SEQUENCE: 42
gatatttgct tcttcttgcc atgg                                          24
```

METHOD FOR STIMULATING CONNECTIVE TISSUE GROWTH OR WOUND HEALING

CROSS REFERENCE TO RELATED APPLICATIONS

This application is a continuation-in-part of U.S. application Ser. No. 10/086,623, filed Mar. 4, 2002, which is a continuation-in-part of U.S. application Ser. No. 09/691,200, filed Oct. 19, 2000, now abandoned, which is a continuation-in-part of U.S. application Ser. No. 09/438,046, filed Nov. 10, 1999 now U.S. Pat. No. 6,706,687 and claims the benefit of U.S. Provisional Application No. 60/107,852, filed Nov. 10, 1998; U.S. Provisional Application No. 60/113,997, filed Dec. 28, 1998; U.S. Provisional Application No. 60/150,604, filed Aug. 26, 1999; U.S. Provisional Application No. 60/157,108, filed Oct. 4, 1999; and U.S. Provisional Application No. 60/157,756, filed Oct. 5, 1999.

FIELD OF THE INVENTION

This invention relates to growth factors for cells expressing receptors to a novel growth factor that include endothelial cells, connective tissue cells (such as fibroblasts) myofibroblasts and glial cells, and in particular to a novel platelet-derived growth factor/vascular endothelial growth factor-like growth factor, polynucleotide sequences encoding the factor, and to pharmaceutical and diagnostic compositions and methods utilizing the factor for stimulating connective tissue growth or promoting wound healing.

BACKGROUND OF THE INVENTION

In the developing embryo, the primary vascular network is established by in situ differentiation of mesodermal cells in a process called vasculogenesis. It is believed that all subsequent processes involving the generation of new vessels in the embryo and neovascularization in adults, are governed by the sprouting or splitting of new capillaries from the pre-existing vasculature in a process called angiogenesis (Pepper et al., 1996, *Enzyme & Protein*, 49:38–162; Breier et al., 1995, *Dev. Dyn.*, 204:228–239; Risau, 1997, *Nature*, 386:671–674). Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

The angiogenic process is highly complex and involves the maintenance of the endothelial cells in the cell cycle, degradation of the extracellular matrix, migration and invasion of the surrounding tissue and finally, tube formation.

The molecular mechanisms underlying the complex angiogenic processes are far from being understood.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., 1992, *J. Biol. Chem.*, 267:10931–10934 for a review.

It has been suggested that a particular family of endothelial cell-specific growth factors, the vascular endothelial growth factors (VEGFs), and their corresponding receptors are primarily responsible for stimulation of endothelial cell growth and differentiation, and for certain functions of the differentiated cells. These factors are members of the PDGF family, and appear to act primarily via endothelial receptor tyrosine kinases (RTKs).

Eight different proteins have been identified in the PDGF family, namely two PDGFs (A and B), VEGF and five members that are closely related to VEGF. The five members closely related to VEGF are: VEGF-B, described in International Patent Application PCT/US96/02957 (WO 96/26736) which corresponds to U.S. Pat. No. 5,928,939, and in U.S. Pat. Nos. 5,840,693 and 5,607,918 to Ludwig Institute for Cancer Research and The University of Helsinki; VEGF-C or VEGF-2, described in Joukov et al., 1996, *EMBO J.*, 15:290–298 and Lee et al., 1996, *Proc. Natl. Acad. Sci. USA*, 93:1988–1992, and U.S. Pat. Nos. 5,932,540, 5,935,820 and 6,040,157; VEGF-D, described in International Patent Application No. PCT/US97/14696 (WO 98/07832), and Achen et al., 1998, *Proc. Natl. Acad. Sci. USA*, 95:548–553; the placenta growth factor (PlGF), described in Maglione et al., 1991, *Proc. Natl. Acad. Sci. USA*, 88:9267–9271; and VEGF3, described in International Patent Application Nos. PCT/US95/07283 (WO 96/39421) and PCT/US99/18054 (WO 00/09148) by Human Genome Sciences, Inc. Each VEGF family member has between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet et al., 1996, *Nature*, 380:435–439; Ferrara et al., 1996, *Nature*, 380:439–442; reviewed in Ferrara and Davis-Smyth, 1997, *Endocrine Rev.*, 18:4–25). The significance of the role played by VEGF has been demonstrated in studies showing that inactivation of a single VEGF allele results in embryonic lethality due to failed development of the vasculature (Carmeliet et al., 1996, *Nature*, 380:435–439; Ferrara et al., 1996, *Nature*, 380:439–442). In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara et al., 1991, *J. Cellular Biochem.,* 47:211–218 and Connolly, J., 1991, *Cellular Biochem.,* 47:219–223. Alterative mRNA splicing of a single VEGF gene gives rise to five isoforms of VEGF.

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for cellular proteins which might interact with cellular retinoid acid-binding protein type I (CRABP-I). Its isolation and characteristics are described in detail in PCT/US96/02957 and in Olofsson et al., 1996, *Proc. Natl. Acad. Sci. USA,* 93:2576–2581.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., 1996, *EMBO J.,* 15:290–298.

VEGF-D was isolated from a human breast cDNA library, commercially available from Clontech, by screening with an expressed sequence tag obtained from a human cDNA library designated "Soares Breast 3NbHBst" as a hybridization probe (Achen et al., 1998, *Proc. Natl. Acad. Sci. USA,* 95:548–553). Its isolation and characteristics are described in detail in International Patent Application No. PCT/US97/14696 (WO98/07832).

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., 1991, *Proc. Natl. Acad. Sci. USA,* 88:9267–9271. Presently its biological function is not well understood.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

PDGF/VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., 1996, *The EMBO Journal,* 15:290–298). VEGF-D binds to both VEGFR-2 and VEGFR-3. A ligand for Tek/Tie-2 has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al., 1998, *Cell,* 92:735–745). The VEGF receptor was found to specifically bind the $VEGF_{165}$ isoform via the exon 7 encoded sequence, which shows weak affinity for heparin (Soker et al., 1998, *Cell,* 92:735–745). Surprisingly, the receptor was shown to be identical to human neuropilin-1 (NP-1), a receptor involved in early stage neuromorphogenesis. PlGF-2 also appears to interact with NP-1 (Migdal et al., 1998, *J. Biol. Chem.,* 273:22272–22278).

VEGFR-1, VEGFR-2 and VEGFR-3 are expressed differently by endothelial cells. Both VEGFR-1 and VEGFR-2 are expressed in blood vessel endothelia (Oelrichs et al., 1992, *Oncogene,* 8:11–18; Kaipainen et al., 1993, *J. Exp. Med.,* 178:2077–2088; Dumont et al., 1995, *Dev. Dyn.,* 203:80–92; Fong et al., 1996, *Dev. Dyn.,* 207:1–10) and VEGFR-3 is mostly expressed in the lymphatic endothelium of adult tissues (Kaipainen et al., 1995, *Proc. Natl. Acad. Sci. USA,* 9:3566–3570). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., 1995, *Nature,* 376:66–70). However, deletion of the intracellular tyrosine kinase domain of VEGFR-1 generates viable mice with a normal vasculature (Hiratsuka et al., 1998, *Proc. Natl. Acad. Sci. USA,* 95:9349–9354). The reasons underlying these differences remain to be explained but suggest that receptor signalling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., 1995, *Nature,* 376:62–66; Shalaby et al., 1997, *Cell,* 89:981–990). Inactivation of VEGFR-3 results in cardiovascular failure due to abnormal organization of the large vessels (Dumont et al., 1998, *Science,* 282:946–949).

Although VEGFR-1 is mainly expressed in endothelial cells during development, it can also be found in hematopoetic precursor cells during early stages of embryogenesis (Fong et al., 1995, *Nature,* 376:66–70). It is also is expressed by most, if not all, vessels in embryos (Breier et al., 1995, *Dev. Dyn.,* 204:228–239; Fong et al., 1996, *Dev. Dyn.,* 207:1–10). In adults, monocytes and macrophages also express this receptor (Barleon et al., 1996, *Blood,* 87:3336–3343).

The receptor VEGFR-3 is widely expressed on endothelial cells during early embryonic development, but as embryogenesis proceeds, it becomes restricted to venous endothelium and then to the lymphatic endothelium (Kaipainen et al., 1994, *Cancer Res.,* 54:6571–6577; Kaipainen et al., 1995, *Proc. Natl. Acad. Sci. USA,* 92:3566–3570). VEGFR-3 continues to be expressed on lymphatic endothelial cells in adults. This receptor is essential for vascular development during embryogenesis. Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5. On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., 1996, *EMBO J.*, 15:290–298).

Some inhibitors of the VEGF/VEGF-receptor system have been shown to prevent tumor growth via an anti-angiogenic mechanism; see Kim et al., 1993, *Nature*, 362: 841–844 and Saleh et al., 1996, *Cancer Res.*, 56:393–401.

As mentioned above, the VEGF family of growth factors are members of the PDGF family. PDGF plays an important role in the growth and/or motility of connective tissue cells, fibroblasts, myofibroblasts and glial cells (Heldin et al., "Structure of platelet-derived growth factor: Implications for functional properties", 1993, *Growth Factor*, 8:245–252). In adults, PDGF stimulates wound healing (Robson et al., 1992, *Lancet*, 339:23–25). Structurally, PDGF isoforms are disulfide-bonded dimers of homologous A- and B-polypeptide chains, arranged as homodimers (PDGF-AA and PDGF-BB) or a heterodimer (PDGF-AB).

PDGF isoforms exert their effects on target cells by binding to two structurally related receptor tyrosine kinases (RTKs). The alpha-receptor binds both the A- and B-chains of PDGF, whereas the beta-receptor binds only the B-chain. These two receptors are expressed by many cell lines grown in vitro, and are mainly expressed by mesenchymal cells in vivo. The PDGFs regulate cell proliferation, cell survival and chemotaxis of many cell types in vitro (reviewed in Heldin et al., 1998, *Biochim Biophys Acta.*, 1378:F79–113). In vivo, they exert their effects in a paracrine mode since they often are expressed in epithelial (PDGF-A) or endothelial cells (PDGF-B) in close apposition to the PDGFR expressing mesenchyme. In tumor cells and in cell lines grown in vitro, coexpression of the PDGFs and the receptors generate autocrine loops which are important for cellular transformation (Betsholtz et al., 1984, *Cell*, 39:447–57; Keating et al., 1990, *J. R. Coll Surg Edinb.*, 35:172–4). Overexpression of the PDGFs have been observed in several pathological conditions, including malignancies, arteriosclerosis, and fibroproliferative diseases (reviewed in Heldin et al., 1996, *The Molecular and Cellular Biology of Wound Repair*, New York: Plenum Press, 249–273).

The importance of the PDGFs as regulators of cell proliferation and survival are well illustrated by recent gene targeting studies in mice that have shown distinct physiological roles for the PDGFs and their receptors despite the overlapping ligand specificities of the PDGFRs. Homozygous null mutations for either of the two PDGF ligands or the receptors are lethal. Approximately 50% of the homozygous PDGF-A deficient mice have an early lethal phenotype, while the surviving animals have a complex postnatal phenotype with lung emphysema due to improper alveolar septum formation because of a lack of alveolar myofibroblasts (Boström et al., 1996, *Cell*, 85:863–873). The PDGF-A deficient mice also have a dermal phenotype characterized by thin dermis, misshapen hair follicles and thin hair (Karlsson et al., 1999, *Development*, 126:2611–2). PDGF-A is also required for normal development of oligodendrocytes and subsequent myelination of the central nervous system (Fruttiger et al., 1999, *Development*, 126: 457–67). The phenotype of PDGFR-alpha deficient mice is more severe with early embryonic death at E10, incomplete cephalic closure, impaired neural crest development, cardiovascular defects, skeletal defects, and edemas (Soriano et al., 1997, *Development*, 124:2691–70). The PDGF-B and PDGFR-beta deficient mice develop similar phenotypes that are characterized by renal, hematological and cardiovascular abnormalities (Levéen et al., 1994, *Genes Dev.*, 8:1875–1887; Soriano et al., 1994, *Genes Dev.*, 8:1888–96; Lindahl et al., 1997, *Science*, 277:242–5; Lindahl, 1998, *Development*, 125:3313–2), where the renal and cardiovascular defects, at least in part, are due to the lack of proper recruitment of mural cells (vascular smooth muscle cells, pericytes or mesangial cells) to blood vessels (Levéen et al., 1994, *Genes Dev.*, 8:1875–1887; Lindahl et al., 1997, *Science*, 277:242–5; Lindahl et al., 1998, *Development*, 125: 3313–2).

Most recently, an additional member of the PDGF/VEGF family of growth factors was identified, PDGF-C. PDGF-C is described in International Patent Application PCT/US99/22668 (WO 00/18212), filed Sep. 30, 1999. PDGF-C has a two-domain structure not previously recognized within this family of growth factors, a N-terminal C1r/C1s/embryonic sea urchin protein Uegf/bone morphogenetic protein 1 (CUB) domain, and a C-terminal PDGF/VEGF homology domain (P/VHD). The structure of the P/VHD in PDGF-C shows a low overall sequence identity with other PDGF/VEGF homology domains, although the eight invariant cysteine residues involved in inter- and intra-molecular disulfide bond formation are present. The cysteine spacing in the central, most conserved region of this domain is different from other PDGF/VEGF domains, with an insertion of three amino acid residues. Despite the fact that the insertion occurs close to the loop 2 region which has been proposed to be involved in receptor binding, it was shown that this domain of PDGF-CC binds PDGFR-alpha with almost identical affinities as homodimers of PDGF-A or -B chains. In addition, four extra cysteine residues are present in this domain. Full length and truncated PDGF-CC were found not to bind to VEGFR-1, -2 or -3, or to PDGFR-beta.

PDGF-C requires proteolytic removal of the N-terminal CUB domain for receptor binding and activation of the receptor. This indicates that the CUB domains are likely to sterically block the receptor binding epitopes of the unprocessed dimer. The in vitro and in vivo proteolytically processed proteins are devoid of N-terminal portions corresponding to more than 14–16 kDa as determined from SDS-PAGE analysis which is consistent with a loss of the 110 amino acid long CUB domain and a part of the hinge region between the CUB and core domains that vary in length.

PDGF-C is not proteolytically processed during secretion in transfected COS cells indicating that proteolytic removal of the CUB domain occurs extracellularly, and not during secretion. This is in contrast to PDGF-A and -B (Östman et al., 1992, *J. Cell. Biol.*, 118:509–519) which appear to be processed intracellularly by furin-like endoproteases (Nakayama et al., 1997, *Biochem J.*, 327:625–635).

Northern blots show PDGF-C mRNA in a variety of human tissues, including heart, liver, kidney, pancreas and ovary.

In situ localization studies demonstrate expression of PDGF-C in certain epithelial structures, and PDGFR-alpha in adjacent mesenchyme, indicating the potential of paracrine signaling in the developing embryo. PDGF-C expression seems particularly abundant at sites of ongoing ductal morphogenesis, indicating a role of the factor in connective tissue remodeling at these sites. The expression pattern is distinct from that of PDGF-A or PDGF-B indicating that the three growth factors have different roles despite their similar PDGFR-alpha binding and signaling activities. This is illustrated by the mouse embryonic kidney, in which PDGF-C is expressed in early aggregates of metanephric mesenchyme undergoing epithelial conversion, whereas PDGF-A is expressed in more mature tubular structures, and PDGF-B by vascular endothelial cells. PDGFR-alpha is expressed in the mesenchyme of the kidney cortex, adjacent to the sites of PDGF-C expression, indicating that this mesenchyme may be targeted specifically by PDGF-C. Indeed, PDGFR-alpha −/− mouse embryos show an extensive loss of the cortical mesenchyme adjacent to sites of PDGF-C expression, not seen in PDGF-A −/− mice or in PDGF-A/B −/− mice, indicating that PDGF-C has an essential role in the development of kidney mesenchyme.

SUMMARY OF THE INVENTION

The invention generally provides an isolated novel growth factor, PDGF-D, a polypeptide that has the ability to stimulate, or enhance, or both, one or more of proliferation, differentiation, growth, and motility of cells expressing a PDGF-D receptor. The cells affected by the inventive growth factor include, but are not limited to, endothelial cells, connective tissue cells, myofibroblasts and glial cells. The invention also provides isolated polynucleotide molecules encoding the novel growth factor, and compositions useful for diagnostic and/or therapeutic applications.

According to one aspect, the invention provides an isolated nucleic acid molecule which comprises a polynucleotide sequence having at least 85% identity, more preferably at least 90%, and still more preferably at least 95% identity, and most preferably at 100% identity to at least nucleotides 1 to 600 of the sequence set out SEQ ID NO:3, at least nucleotides 1 to 966 of the sequence set out in SEQ ID NO:5, at least nucleotides 176 to 1285 of the sequence set out in SEQ ID NO:7, at least nucleotides 935 to 1285 set out in SEQ ID NO:7, at least nucleotides 1 to 1110 of SEQ ID NO:35, at least nucleotides 1–1092 of SEQ ID NO:37, or SEQ ID NO:39. The sequence of at least nucleotides 1 to 600 of the sequence set out in FIG. 3 (SEQ ID NO:3) or at least nucleotides 1 to 966 of the sequence set out in FIG. 5 (SEQ ID NO:5) encodes a 5'-truncated polypeptide, designated PDGF-D (formerly designated "VEGF-G"), while at least nucleotides 176 to 1285 of the sequence set out in FIG. 7 (SEQ ID NO:7) encodes a full-length PDGF-D. The sequence of at least nucleotides 1 to 1110 of SEQ ID NO:35 encodes a murine PDGF-D, while the sequence of at least nucleotides 1–1092 of SEQ ID NO:37 encodes an identical protein as SEQ ID NO:35 except for a six amino acid residue gap (a.a. #42–47) from the region between the signal sequence and the CUB domain (see below for details), and SEQ ID NO:39 a C-terminal truncated protein of the polypeptide encoded by SEQ ID NO:35. The PDGF-D polynucleotide of the invention can be a naked polynucleotide and/or in a vector or liposome.

PDGF-D is structurally homologous to PDGF-A, PDGF-B, VEGF, VEGF-B, VEGF-C and VEGF-D. The sequence of at least nucleotides 935 to 1285 set out in FIG. 7 (SEQ ID NO:7) encodes a portion of the PDGF/VEGF homology domain, which is the bioactive fragment of PDGF-D. This bioactive fragment would also be encoded by the sequence of at least nucleotides 1 to 600 of the sequence set out in FIG. 3 (SEQ ID NO:3) or at least nucleotides 1 to 966 of the sequence set out in FIG. 5 (SEQ ID NO:5).

According to a second aspect, the PDGF-D polypeptide of the invention has the ability to stimulate and/or enhance proliferation and/or differentiation and/or growth and/or motility of cells expressing a PDGF-D receptor including, but not limited to, endothelial cells, connective tissue cells, myofibroblasts and glial cells and comprises a sequence of amino acids having at least 85% identity, more preferably at least 90%, and still more preferably at least 95% identity, and most preferably at 100% identity to the amino acid sequence set out in SEQ ID NOs:4, 6, 8, 36, 38 or 40, or a fragment or analog thereof which has PDGF-D activity.

A preferred fragment is a truncated form of PDGF-D comprising a portion of the PDGF/VEGF homology domain (PVHD) of PDGF-D. The portion of the PVHD is from residues 254–370 of FIG. 8 (SEQ ID NO:8) where the putative proteolytic processing site RKSK starts at amino acid residue 254 (SEQ ID NO:8). However, the PVHD extends toward the N terminus up to residue 234 of FIG. 8 (SEQ ID NO:8). Herein the PVHD is defined as truncated PDGF-D. The truncated PDGF-D is the putative activated form of PDGF-D.

Another preferred fragment is a truncated form of PDGF-D comprising only the CUB domain, as exemplified by the sequence set forth in SEQ ID NO:40. There may exist PDGF-D receptors, other than PDGFR-beta, that bind to the unprocessed or un-cleaved factor (CUB+PDGF-homology domain). The CUB domain alone may bind to these receptors and would prevent activation of said receptors by blocking the receptors from binding to un-cleaved factors.

As used in this application, percent sequence identity is determined by using the alignment tool of "MEGALIGN" from the Lasergene package (DNASTAR, Ltd. Abacus House, Manor Road, West Ealing, London W130AS United Kingdom). The MEGALIGN is based on the J. Hein method (Methods in Enzymology, 1990 183 626–645). The PAM 250 residue weight table is used with a gap penalty of eleven and a gap length penalty of three and a K-tuple value of two in the pairwise alignments. The alignment is then refined manually, and the number of identities are estimated in the regions available for a comparison.

Preferably the polypeptide has the ability to stimulate one or more of proliferation, differentiation, motility, survival or vascular permeability of cells expressing a PDGF-D receptor including, but not limited to, vascular endothelial cells, lymphatic endothelial cells, connective tissue cells (such as fibroblasts), myofibroblasts and glial cells. Preferably the polypeptide has the ability to stimulate wound healing. PDGF-D also has antagonistic effects on cells. For example, an antagonistic PDGF-D variant would be a partial PDGF-D molecule containing one intact full-length chain and one processed chain as a disulphide-linked dimer. In principle such a molecule would be monovalent and bind to single PDGFR-beta receptors, but prevent their dimerization thereby blocking signal transduction. These antagonistic activities are also included in the biological activities of PDGF-D. Collectively, both the stimulating and antagonistic abilities are referred to hereinafter as "biological activities of PDGF-D" and can be readily tested by methods known in the art.

In another preferred aspect, the invention provides a polypeptide comprising an amino acid sequence:

PXCLLVXRCGGNCGC (SEQ ID NO:25)

which is unique to PDGF-D and differs from the other members of the PDGF/VEGF family of growth factors because of the insertion of the three amino acid residues (NCG) between the third and fourth cysteines (see FIG. 9).

Polypeptides comprising conservative substitutions, insertions, or deletions, but which still retain a biological activity of PDGF-D are within the scope of the invention. Persons skilled in the art will be well aware of methods which can readily be used to generate such polypeptides, for example the use of site-directed mutagenesis, or specific enzymatic cleavage and ligation. The skilled person will also be aware that peptidomimetic compounds or compounds in which one or more amino acid residues are replaced by a non-naturally occurring amino acid or an amino acid analog may retain the required aspects of the biological activity of PDGF-D. Such compounds can readily be made and tested for their ability to show the biological activity of PDGF-D by routine activity assay procedures such as the fibroblast proliferation assay and are also within the scope of the invention.

In addition, possible variant forms of the PDGF-D polypeptide which may result from alternative splicing, as are known to occur with VEGF and VEGF-B, and naturally-occurring allelic variants of the nucleic acid sequence encoding PDGF-D are within the scope of the invention. Examples of such a variant include the polypeptides set forth in SEQ ID NOs: 38 and 40. Allelic variants are well known in the art, and represent alternative forms or a nucleic acid sequence which comprise substitution, deletion or addition of one or more nucleotides, but which do not result in any substantial functional alteration of the encoded polypeptide.

Such variant forms of PDGF-D can be prepared by targeting non-essential regions of the PDGF-D polypeptide for modification. These non-essential regions are expected to fall outside the strongly-conserved regions indicated in FIG. 9 (SEQ ID NOs:8 and 32). In particular, the growth factors of the PDGF family, including PDGF-D, are dimeric. PDGF-D differs slightly from VEGF, VEGF-B, VEGF-C, VEGF-D, PlGF, PDGF-A and PDGF-B because it shows complete conservation of only seven of the eight cysteine residues in the PVHD (Olofsson et al., 1996, *Proc. Natl. Acad. Sci. USA*, 93:2576–2581; Joukov et al., 1996, *EMBO J.*, 15:290–298). These cysteines are thought to be involved in intra- and inter-molecular disulfide bonding. Loops 1, 2 and 3 of each subunit, which are formed by intra-molecular disulfide bonding, are involved in binding to the receptors for the PDGF/VEGF family of growth factors (Andersson et al., 1995, *Growth Factors*, 12:159–164).

Persons ordinarily skilled in the art thus are well aware that these cysteine residues generally should be preserved and that the active sites present in loops 1, 2 and 3 also should be preserved. However, other regions of the molecule can be expected to be of lesser importance for biological function, and therefore offer suitable targets for modification. Modified polypeptides can readily be tested for their ability to show the biological activity of PDGF-D by routine activity assay procedures such as the fibroblast proliferation assay.

It is contemplated that some modified PDGF-D polypeptides will have the ability to bind to PDGF-D receptors on cells including, but not limited to, endothelial cells, connective tissue cells, myofibroblasts and/or glial cells, but will be unable to stimulate cell proliferation, differentiation, migration, motility or survival or to induce vascular proliferation, connective tissue development or wound healing. These modified polypeptides are expected to be able to act as competitive or non-competitive inhibitors of the PDGF-D polypeptides and growth factors of the PDGF/VEGF family, and to be useful in situations where prevention or reduction of the PDGF-D polypeptide or PDGF/VEGF family growth factor action is desirable. Thus such receptor-binding but non-mitogenic, non-differentiation inducing, non-migration inducing, non-motility inducing, non-survival promoting, non-connective tissue promoting, non-wound healing or non-vascular proliferation inducing variants of the PDGF-D polypeptide are also within the scope of the invention, and are referred to herein as "receptor-binding but otherwise inactive variants." Because PDGF-D forms a dimer in order to activate its only known receptor, it is contemplated that one monomer comprises the receptor-binding but otherwise inactive variant modified PDGF-D polypeptide and a second monomer comprises a wild-type PDGF-D or a wild-type growth factor of the PDGF/VEGF family. These dimers can bind to its corresponding receptor but cannot induce downstream signaling.

It is also contemplated that there are other modified PDGF-D polypeptides that can prevent binding of a wild-type PDGF-D or a wild-type growth factor of the PDGF/VEGF family to its corresponding receptor on cells including, but not limited to, endothelial cells, connective tissue cells (such as fibroblasts), myofibroblasts and/or glial cells. Thus these dimers will be unable to stimulate endothelial cell proliferation, differentiation, migration, survival, or induce vascular permeability, and/or stimulate proliferation and/or differentiation and/or motility of connective tissue cells, myofibroblasts or glial cells. These modified polypeptides are expected to be able to act as competitive or non-competitive inhibitors of the PDGF-D growth factor or a growth factor of the PDGF/VEGF family, and to be useful in situations where prevention or reduction of the PDGF-D growth factor or PDGF/VEGF family growth factor action is desirable. Such situations include the tissue remodeling that takes place during invasion of tumor cells into a normal cell population by primary or metastatic tumor formation. Thus such PDGF-D or PDGF/VEGF family growth factor-binding but non-mitogenic, non-differentiation inducing, non-migration inducing, non-motility inducing, non-survival promoting, non-connective tissue promoting, non-wound healing or non-vascular proliferation inducing variants of the PDGF-D growth factor are also within the scope of the invention, and are referred to herein as "the PDGF-D growth factor-dimer forming but otherwise inactive or interfering variants."

An example of a PDGF-D growth factor-dimer forming but otherwise inactive or interfering variant is where the PDGF-D has a mutation which prevents cleavage of CUB domain from the protein. It is further contemplated that a PDGF-D growth factor-dimer forming but otherwise inactive or interfering variant could be made to comprise a monomer, preferably a monomer whose own N-terminal CUB domain has been removed (hereinafter a "CUB-removed monomer") of VEGF, VEGF-B, VEGF-C, VEGF-D, PDGF-A, PDGF-B, PDGF-C, PDGF-D or PlGF linked to a CUB domain that has a mutation which prevents cleavage of CUB domain from the protein. Dimers formed with the above mentioned PDGF-D growth factor-dimer forming but otherwise inactive or interfering variants and the monomers linked to the mutant CUB domain would be unable to bind to their corresponding receptors.

A variation on this contemplation would be to insert a proteolytic site between a CUB-removed monomer of VEGF, VEGF-B, VEGF-C, VEGF-D, PDGF-A, PDGF-B, PDGF-C, PDGF-D or PlGF and the mutant CUB domain which is dimerized to a CUB-removed monomer of VEGF, VEGF-B, VEGF-C, VEGF-D, PDGF-A, PDGF-B, PDGF-C, PDGF-D or PlGF. Addition of the specific protease(s) for this proteolytic site would cleave the CUB domain and thereby release an activated dimer that can then bind to its corresponding receptor. In this way, a controlled release of an activated dimer is made possible.

According to a third aspect, the invention provides a purified and isolated nucleic acid encoding a polypeptide or polypeptide fragment of the invention as defined above. The nucleic acid may be DNA, genomic DNA, cDNA or RNA, and may be single-stranded or double stranded. The nucleic acid may be isolated from a cell or tissue source, or of recombinant or synthetic origin. Because of the degeneracy of the genetic code, the person skilled in the art will appreciate that many such coding sequences are possible, where each sequence encodes the amino acid sequence shown in FIG. 4 (SEQ ID NO:4), FIG. 6 (SEQ ID NO:6) or FIG. 8 (SEQ ID NO:8), a bioactive fragment or analog thereof, a receptor-binding but otherwise inactive or partially inactive variant thereof or a PDGF-D dimer-forming but otherwise inactive or interfering variants thereof.

A fourth aspect of the invention provides vectors comprising the cDNA of the invention or a nucleic acid molecule according to the third aspect of the invention, and host cells transformed or transfected with nucleic acids molecules or vectors of the invention. These may be eukaryotic or prokaryotic in origin. These cells are particularly suitable for expression of the polypeptide of the invention, and include insect cells such as Sf9 cells, obtainable from the American Type Culture Collection (ATCC SRL-171), transformed with a baculovirus vector, and the human embryo kidney cell line 293-EBNA transfected by a suitable expression plasmid. Preferred vectors of the invention are expression vectors in which a nucleic acid according to the invention is operatively connected to one or more appropriate promoters and/or other control sequences, such that appropriate host cells transformed or transfected with the vectors are capable of expressing the polypeptide of the invention. Other preferred vectors are those suitable for transfection of mammalian cells, or for gene therapy, such as adenoviral-, vaccinia- or retroviral-based vectors or liposomes. A variety of such vectors is known in the art.

The invention also provides a method of making a vector capable of expressing a polypeptide encoded by a nucleic acid molecule according to the invention, comprising the steps of operatively connecting the nucleic acid molecule to one or more appropriate promoters and/or other control sequences, as described above.

The invention further provides a method of making a polypeptide according to the invention, comprising the steps of expressing a nucleic acid or vector of the invention in a host cell, and isolating the polypeptide from the host cell or from the host cell's growth medium.

In yet a further aspect, the invention provides an antibody specifically reactive with a polypeptide of the invention or a fragment of the polypeptide. This aspect of the invention includes antibodies specific for the variant forms, immunoreactive fragments, analogs and recombinants of PDGF-D. Such antibodies are useful as inhibitors or antagonists of PDGF-D and as diagnostic agents for detecting and quantifying PDGF-D. Polyclonal or monoclonal antibodies may be used. Monoclonal and polyclonal antibodies can be raised against polypeptides of the invention or fragment or analog thereof using standard methods in the art. In addition the polypeptide can be linked to an epitope tag, such as the FLAG® octapeptide (Sigma, St. Louis, Mo.), to assist in affinity purification. For some purposes, for example where a monoclonal antibody is to be used to inhibit effects of PDGF-D in a clinical situation, it may be desirable to use humanized or chimeric monoclonal antibodies. Such antibodies may be further modified by addition of cytotoxic or cytostatic drug(s). Methods for producing these, including recombinant DNA methods, are also well known in the art.

This aspect of the invention also includes an antibody which recognizes PDGF-D and is suitably labeled.

Polypeptides or antibodies according to the invention may be labeled with a detectable label, and utilized for diagnostic purposes. Similarly, the thus-labeled polypeptide of the invention may be used to identify its corresponding receptor in situ. The polypeptide or antibody may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}I$ or $^{32}P$. Examples of non-radioactive labels include enzymatic labels, such as horseradish peroxidase or fluorimetric labels, such as fluorescein-5-isothiocyanate (FITC). Labeling may be direct or indirect, covalent or non-covalent.

Clinical applications of the invention include diagnostic applications, acceleration of angiogenesis in tissue or organ transplantation to promote graft growth and vascularization, or stimulation of wound healing, or connective tissue development, or to establish collateral circulation in tissue infarction or arterial stenosis, such as coronary artery disease, and inhibition of angiogenesis in the treatment of cancer or of diabetic retinopathy and inhibition of tissue remodeling that takes place during invasion of tumor cells into a normal cell population by primary or metastatic tumor formation. Quantitation of PDGF-D in cancer biopsy specimens may be useful as an indicator of future metastatic risk.

PDGF-D may also be relevant to a variety of lung conditions. PDGF-D assays could be used in the diagnosis of various lung disorders. PDGF-D could also be used in the treatment of lung disorders to improve blood circulation in the lung and/or gaseous exchange between the lungs and the blood stream. Similarly, PDGF-D could be used to improve blood circulation to the heart and $O_2$ gas permeability in cases of cardiac insufficiency. In a like manner, PDGF-D could be used to improve blood flow and gaseous exchange in chronic obstructive airway diseases.

Thus the invention provides a method for stimulating angiogenesis, lymphangiogenesis, neovascularization, connective tissue development and/or wound healing in a mammal in need of such treatment, comprising the step of administering an effective dose of PDGF-D, or a fragment or an analog thereof which has the biological activity of PDGF-D to the mammal. The PDGF-D polypeptides may be administered either in the form of its bioactive fragment (e.g. residues 254–370 of SEQ ID NO: 8), or in the form of a full-length sequence which may be activated, e.g. with a suitable protease, in situ. Alternatively, a nucleic acid molecule coding for a bioactive PDGF-D polypeptide may be administered, or a nucleic acid molecule coding for a full-length PDGF-D polypeptide together with a nucleic acid molecule coding for a suitable protease are administered together, preferably under the control of regulatory elements suitable for regulation of their respective expression. Optionally the PDGF-D, or fragment or analog thereof may be administered together with, or in conjunction with, one or more of VEGF, VEGF-B, VEGF-C, VEGF-D, PlGF, PDGF-A, PDGF-B, PDGF-C, FGF and/or heparin.

PDGF-D polypeptides may be directly delivered to the site of interest where angiogenesis etc are desired. Numerous direct polypeptide delivery methods are known and may be used. See e.g. Talmadge, 1993, The pharmaceutics and delivery of therapeutic polypeptides and proteins, *Adv. Drug Del. Rev.* 10:247–299. The polypeptides may be administered orally. Although polypeptides are generally known to have poor availability through oral administration, various methods known in the art have been developed to overcome this limitation. For example, biodegradable polymeric matrices have been used for delivering proteins over a desired period of time. For example, the use of biodegradable poly(d, l-lactic-co-glycolic acid) (PLGA) microspheres for the delivery of peptides and proteins has been widely reported (Mehta et al., 1996, Peptide containing microspheres from low molecular weight and hydrophilic poly(d, l-lactide-co-glycolide), *J. Control Release* 41:249–257; Chiba et al., 1997, Controlled protein delivery from biodegradable tyrosine-containing poly(anhydride-co-imide) microspheres. *Biomaterials* 18:893–901; Ravivarapu et al., 2000, Polymer and microsphere blending to alter the release of a peptide from PLGA microspheres, *Eur. J. Pharm. Biopharm.* 50:263–270).

Preferably, direct application of the polypeptides, especially direct injection, may be used. Because wound-healing and other conditions requiring enhanced angiogenesis typically require local application of PDGF-D polypeptides and other growth factors for only a limited time, direct injection, even frequent direct injection of the polypeptides to the desired site(s) is acceptable and is not likely to be very tedious or expensive and pose problems such as poor patient acceptance. Methods of direct application of polypeptides are well-known to those ordinarily skilled in the art, and recent successes, strategies, and potentials of topical application of PDGF-BB in improving healing were reviewed by Cupp et al., 2002, Gene therapy, electroporation, and the future of wound-healing therapies, *Facial Plast. Surg.* 18:53–57.

In another preferred embodiment, the therapeutic polypeptides of the present invention may be delivered in the form of nucleic acid molecules encoding the polypeptides. Many established and well-known methods for gene delivery or gene therapy may be used for administering genes or other nucleic acid molecules encoding PDGF-D to the patient. See e.g. Rubany, 2001, The future of human gene therapy, *Mol. Aspects. Med.* 22:113–42. A single dose of naked DNA of VEGF and PDGF was used to treat rats with cysteanmine-induced duodenal ulcers, and was shown to significantly accelerate chronic duodenal ulcer healing, and increase VEGF and PDGF levels in duodenal mucosa (Szabo et al., 2001, Gene Expression and gene therapy in experimental duodena ulceration, *J. Physiol. Paris* 95:325–335).

The polynucleotides encoding PDGF-D preferably are linked operatively under the control of suitable promoter so that they are expressed when taken up by the host cells. PDGF-D is a diffusible protein, and as such it will exert its effects on cells directly expressing the polypeptides, as well as on surrounding cells. Accordingly, suitable promoters may be constitutive promoters such as promoter and enhancer elements from cytomegalovirus (CMV), Rous sarcoma virus (RSV), and SV40, and the rat beta-actin promoter. Preferably, inducible or tissue specific promoters are used to increase expression level, improve specificity and reduce side effects. In this regard, suitable promoters include the keratin 5 (K5) promoter (Pierce et al., 1998, *Oncogene* 16: 1267–1276; Pierce et al., 1998, *Proc. Natl. Acad. Sci. USA* 95:8858–8863), the Cyr61 promoter (inducible in granulation tissue during wound healing) (Latinkic et al., 2001, Promoter function of the angiogenic inducer Cyr61 gene in transgenic mice: tissue specificity, inducibility during wound healing, and role of the serum response element, *Endocrinol.* 142:2549–2557), and the FAP promoter (Neidermeyer et al., 2001, Expression of the fibroblast activation protein during mouse embryo development, *Int. J. Dev. Biol.* 45:445–447).

Suitable polynucleotides may also be delivered as non-viral vectors, using methods well-known to those ordinarily skilled in the art. See e.g. Brown et al., 2001, Gene delivery with synthetic (non-viral) carriers, *Int. J. Pharm.* 229:1–21; and Pouton et al., 1998, Key issues in non-viral gene delivery, *Adv. Drug Deliv. Rev.* 34:3–19.). Lipofection, liposome mediated gene transfer are preferred (Romano et al., 1999, Gene transfer technology in therapy: current applications and future goals. *Stem Cells* 17:191–202; Mountain, 2000, Gene therapy: the first decade. *Trends. Biotechnol.* 18:119–28; Mhashilkar et al., 2001, Gene therapy: Therapeutic approaches and implications. *Biotechnol. Adv.* 19:279–97; and Lasic, 1998, Novel applications of liposomes, *Trends Biotechnol.* 16:307–21).

One of the simplest ideas for non-viral gene delivery is the use of purified DNA in the form of plasmids. A naked polynucleotide operatively coding for the polypeptide may be delivered, along with a pharmaceutically acceptable carrier, directly to the desired site, where the polynucleotide is taken up by the cells at the site and expressed or otherwise exerts its therapeutic effects. This is particularly preferred if transient expression of the gene is desired. The transfer of naked DNA by physical means is well known, by such means as gene guns and electroporation. See e.g. Spack et al., 2001, Developing non-viral DNA delivery systems for cancer and infectious disease, *DDT* 6:186–97. See also Cupp et al., 2002, supra.

In general, RNA molecules will have more transient effects than DNA molecules. The effects of the naked RNA molecules so delivered last typically for less than about 20 days, usually less than 10 days, and often less than 3 to 5 days. Delivery may be by injection, spray, biolistic methods, and so on, depending on the site.

In another embodiment, suitable polynucleotides may also be delivered within viral vectors, which are known to have higher transfection efficiency compared to nonviral vectors. See e.g. Robbins et al., 1998, Viral vectors for gene therapy, *Pharmacol. Ther.* 80:35–47; and Kay et al., 2001, Viral vectors for gene therapy: the art of turning infectious agents into vehicles of therapeutics, *Nat. Med.* 7:33–40. Suitable viral vectors include those derived from retroviruses (including lentivirues) (see e.g. Breithart et al., 1999, *Ann. Plast. Surg.* 43:632–9), especially the Moloney murineleukemia virus and pseudotyped retroviruses (Chen et al., 2001, Safety testing for replication-competent retrovirus associated with gibbon apeleukemia virus-pseudotyped retroviral vectors. *Hum. Gene. Ther.* 12:61–70); adenoviruses, especially the third generation "gutless" adenoviral vector (Kochanek et al., 2001, High-capacity "gutless" adenoviral vectors. *Curr. Opin. Mol. Ther.* 3:454–63.); chimeric viruses that combine the advantages of both retroviruses and adenoviruses (Reynolds et al., 1999, Chimeric viral vectors-the best of both worlds? *Mol. Med. Today* 5:25–31, 1999); adeno-associated virus (Ponnazhagan et al., 2001, Adeno-associated virus for gene therapy. *Cancer Res.*, 61:6313–21; and Monahan et al., 2000, Adeno-associated virus vectors for gene therapy: more pros than cons? *Mol. Med. Today*, 6:433–40.); vaccinia viruses (Peplinski, et al., 1998, Vaccinia virus for human gene therapy. *Surg. Oncol. Clin. N. Am.*, 7:575–588); and herpes simplex virus (Latchman. 2001, Gene delivery and gene therapy with herpes simplex virus-based vectors. *Gene* 264:1–9).

Adenoviral vectors are preferred. Chen et al. (2002) showed that recombinant adenoviruses encoding the PDGF-A gene express and secrete PDGF-A in vitro, and induce sustained down regulation of PDGFαR encoded by the growth arrest specific (gas) gene (Am. J. Physiol. Cell Physiol. 282:C538–44). Szabo et al., supra, used a single dose of adenoviral vectors expressing VEGF and PDGF to treat rats with cysteanmine-induced duodenal ulcers, and showed significant acceleration of chronic duodenal ulcer healing, and increased VEGF and PDGF levels in duodenal mucosa. Giannobile et al., 2001, *J. Periodontol.* 72:815–23 showed that adenoviral vectors expressing PDGF-A stimulated cementoblast DNA synthesis and subsequent proliferation. Zhu et al., 2001, *J. Dent. Res.* 80:892–7 demonstrated that adenoviruses encoding PDGF-A enhanced mitogenic and proliferative responses in osteoblasts, periodontal ligament fibroblasts and gingival fibroblasts. See also Liechty et al., 1999, Adenoviral mediated overexpression of PDGF-B corrects ischemic impaired wound healing, *J. Invest. Dermatol.* 113:375–83.

The effects of vectors coding for PDGF-D polypeptides may also be improved with matrix immobilization to enhance tissue repair activity. Biocompatible matrices capable of immobilizing adenoviral vectors have been successfully used in treating ischemic excisional wounds. Specifically, collagen-formulated vectors encoding PDGF-B, when delivered as subcutaneously implanted sponges, have been shown to enhance granulation tissue deposition, enhance epithelial area, and improve wound closure more effectively than aqueous formulations of the same vectors. With longer time, complete healing without excessive scar formation was achieved. In comparison, aqueous formulations allowed vector seepage and led to PDGF-induced hyperplasia in surrounding tissues but not in wound beds. In addition, repeated applications of PDGF-BB proteins were required for neotissue induction approaching equivalence to a single application of collagen-immobilized vectors. (Doukas et al., 2002, *Hum. Gene Ther.* 12:783–98). In the same study, Doukas et al. also showed that vectors encoding fibroblast growth factor 2 or vascular endothelial growth factor promoted primarily angiogenic responses. Similar improvements were observed in dermal ulcer wounds in the ears of young adult New Zealand white rabbits with collagen embedded PDGF-B or PDGF-A DNA plasmids (Tyrone et al., 2000, *J. Surg. Res.* 93:230–6); in soft tissue repair by enhancing de novo tissue formation (Chandler et al., 2000, *Mol. Ther.* 2:153–60).

Other materials may also be used as sustained release matrices for delivering vectors encoding PDGF genes. For example, matrices of poly(lactide-co-glycolide) (PLG) were loaded with plasmids and shown to release the plasmids over a period ranging from days to months in vitro, and led to the transfection of large numbers of cells. In vivo delivery enhanced matrix deposition and blood vessel formation in the developing tissue (Shea et al., 1999, *Nat. Biotechnol.* 17:551–4).

Another method of gene delivery uses fusigenic virosomes. This approach combines some of the advantages of viral delivery vectors with the safety and 'simplicity' of the liposome to produce fusigenic virosomes (Dzau et al., 1996, Fusigenic viral liposome for gene therapy in cardiovascular diseases. *Proc Natl. Acad. Sci. USA* 93:11421–25). Virosomes have been engineered by complexing the membrane fusion proteins of haemagglutinating virus of Japan (HVJ, which is also known as Sendai virus) with either liposomes that already encapsulate plasmid DNA or oligodeoxynucleotides (ODN) for antisense applications. The inherent ability of the viral proteins in virosomes to cause fusion with cell membranes means that these hybrid vectors can be very efficient at introducing their nucleic acid to the target cell, resulting in good gene expression. Each viral vector has a limit on the size of transgene that can be incorporated into its genome; no such limit exists for virosome or liposome technology. Genes of up to 100 kilobase pairs have been delivered by fusigenic virosomes to cells both ex vivo and in vivo.

A further embodiment of the invention utilizes DNA-ligand conjugates for delivery of genes encoding the PDGF-polypeptides. DNA-ligand conjugates have two main components: a DNA-binding domain and a ligand for cell-surface receptors. The transgene can therefore be guided specifically to the target cell, where it is internalized via receptor-mediated endocytosis. Once the DNA-ligand complex is in the endocytic pathway, the conjugate is likely to be destroyed when the endosome fuses with a lysosome. To avoid this, an adenovirus-derived domain may be incorporated into the cell-surface receptor part of the ligand (Curiel et al, 1992, High-efficiency gene transfer mediated by adenovirus coupled to DNA-polylysine complexes, *Hum. Gene Ther.* 3:147–154). The conjugates then have the same specificity as adenoviruses, binding to a wide host-cell range; they also possess an adenovirus characteristic that allows the conjugate to leave the endosome and enter the cytoplasm (by a process known as endosomolysis) before the endosome is destroyed by a lysosome.

According to another embodiment of the invention, suitable host cells may be transformed with polynucleotides, preferably vectors, more preferably viral vectors, encoding the PDGF-D polypeptides of the invention, and the host cells expressing the PDGF-D polypeptides may be introduced to a host animal in need of wound healing or other treatment. Many methods of in vitro cell transformation are known and well established in the art, including $CaPO_4$ transfection, which is a chemical method that has been successfully used by molecular biologists for many years to introduce transgenes into cells in vitro with a relatively good efficiency (10%). Mathisen et at. showed that autoreactive memory Th2 T cells can be genetically modified so that upon engagement of self antigen they produce regenerative growth factors such as PDGF-A capable of mediating tissue repair during autoimmune disease (Mathisen et al., 1999, *J. Autoimmun.* 13:31–8

Conversely, PDGF-D antagonists (e.g. antibodies and/or competitive or noncompetitive inhibitors of binding of PDGF-D in both dimer formation and receptor binding) could be used to treat conditions, such as congestive heart failure, involving accumulation of fluid in, for example, the lung resulting from increases in vascular permeability, by exerting an offsetting effect on vascular permeability in order to counteract the fluid accumulation. Administrations of PDGF-D could be used to treat malabsorptive syndromes in the intestinal tract, liver or kidneys as a result of its blood circulation increasing and vascular permeability increasing activities.

Thus, the invention provides a method of inhibiting angiogenesis, lymphangiogenesis, neovascularization, connective tissue development and/or wound healing in a mammal in need of such treatment, comprising the step of administering an effective amount of an antagonist of PDGF-D to the mammal. The antagonist may be any agent that prevents the action of PDGF-D, either by preventing the binding of PDGF-D to its corresponding receptor on the target cell, or by preventing activation of the receptor, such as using receptor-binding but otherwise inactive PDGF-D variants. Suitable antagonists include, but are not limited to, antibodies directed against PDGF-D; competitive or non-competitive inhibitors of binding of PDGF-D to the PDGF-D receptor(s), such as the receptor-binding or PDGF-D dimer-forming but non-mitogenic PDGF-D variants referred to above; and anti-sense nucleotide sequences as described below. For example, a truncated PDGFβ receptor was shown to inhibit thrombosis and neointima formation in an avian arterial injury model (Ding et al., 2001, *Thromb. Haemost.* 86:914–22).

In one embodiment, an antagonist of PDGF-D is a negative dominant mutant of a PDGF-D gene. This negative dominant mutant is able to inhibit the expression of the native PDGF-D gene in the appropriate tissue of the animal, thereby disrupting PDGF-D activity. See e.g. Chen et al., 2002, *Am. J. Physiol. Cell Physiol.* 282:C538–44 (showing that dominant negative mutant of PDGF-A gene disrupts PDGF activity).

A method is provided for determining agents that bind to an activated truncated form of PDGF-D. The method comprises contacting an activated truncated form of PDGF-D with a test agent and monitoring binding by any suitable means. Potential binding agents include proteins and other substances. The invention provides a screening system for discovering agents that bind an activated truncated form of PDGF-D. The screening system comprises preparing an activated truncated form of PDGF-D, exposing the activated truncated form of PDGF-D to a test agent, and quantifying the binding of said agent to the activated truncated form of PDGF-D by any suitable means. The inhibitory effects of a binding agent are further determined by assaying the PDGF-D activities of the PDGF-D polypeptides bound with the binding agent. Both in vivo and in vitro assay methods may be used. Specifically, this screening system is used to identify agents which inhibit the proteolytic cleavage of the full length PDGF-D protein and thereby prevent the release of the activated truncated form of PDGF-D. For this use, the full length PDGF-D is generally preferred.

Use of this screening system provides a means to determine compounds that may alter the biological function of PDGF-D. This screening method may be adapted to large-scale, automated procedures such as a PANDEX® (Baxter-Dade Diagnostics) system, allowing for efficient high-volume screening of potential therapeutic agents.

For this screening system, an activated truncated form of PDGF-D or full length PDGF-D is prepared as described herein, preferably using recombinant DNA technology. A test agent, e.g. a compound or protein, is introduced into a reaction vessel containing the activated truncated form of or full length PDGF-D. Binding of the test agent to the activated truncated form of or full length PDGF-D is determined by any suitable means which include, but is not limited to, radioactively- or chemically-labeling the test agent. Binding of the activated truncated form of or full length PDGF-D may also be carried out by a method disclosed in U.S. Pat. No. 5,585,277, which is incorporated by reference. In this method, binding of the test agent to the activated truncated form of or full length PDGF-D is assessed by monitoring the ratio of folded protein to unfolded protein. Examples of this monitoring can include, but are not limited to, monitoring the sensitivity of the activated truncated form of or full length PDGF-D to a protease, or amenability to binding of the protein by a specific antibody against the folded state of the protein.

Those of skill in the art will recognize that $IC_{50}$ values are dependent on the selectivity of the agent tested. For example, an agent with an $IC_{50}$ which is less than 10 nM is generally considered an excellent candidate for drug therapy. However, an agent which has a lower affinity, but is selective for a particular target, may be an even better candidate. Those skilled in the art will recognize that any information regarding the binding potential, inhibitory activity or selectivity of a particular agent is useful toward the development of pharmaceutical products.

Where PDGF-D or a PDGF-D antagonist is to be used for therapeutic purposes, the dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. Topical application of PDGF-D may be used in a manner analogous to VEGF. Where used for wound healing or other use in which enhanced angiogenesis is advantageous, an effective amount of the truncated active form of PDGF-D is administered to an organism in need thereof in a dose between about 0.1 and 1000 μg/kg body weight.

The PDGF-D or a PDGF-D antagonist may be employed in combination with a suitable pharmaceutical carrier. The resulting compositions comprise a therapeutically effective amount of PDGF-D or a PDGF-D antagonist, and a pharmaceutically acceptable non-toxic salt thereof, and a pharmaceutically acceptable solid or liquid carrier or adjuvant. Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation should be constituted to suit the mode of administration. Compositions which comprise PDGF-D may optionally further comprise one or more of PDGF-A, PDGF-B, PDGF-C, VEGF, VEGF-B, VEGF-C, VEGF-D, PlGF and/or heparin. Compositions comprising PDGF-D will contain from about 0.1% to 90% by weight of the active compound(s), and most generally from about 10% to 30%.

For intramuscular preparations, a sterile formulation, preferably a suitable soluble salt form of the truncated active form of PDGF-D, such as hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

According to yet a further aspect, the invention provides diagnostic/prognostic devices typically in the form of test kits. For example, in one embodiment of the invention there is provided a diagnostic/prognostic test kit comprising an antibody to PDGF-D and a means for detecting, and more preferably evaluating, binding between the antibody and PDGF-D. In one preferred embodiment of the diagnostic/prognostic device according to the invention, a second antibody (the secondary antibody) directed against antibodies of the same isotype and animal source of the antibody directed against PDGF-D (the primary antibody) is provided. The secondary antibody is coupled directly or indirectly to a detectable label, and then either an unlabeled primary antibody or PDGF-D is substrate-bound so that the PDGF-D/primary antibody interaction can be established by determining the amount of label bound to the substrate following binding between the primary antibody and PDGF-D and the subsequent binding of the labeled secondary antibody to the primary antibody. In a particularly preferred embodiment of the invention, the diagnostic/prognostic device may be provided as a conventional enzyme-linked immunosorbent assay (ELISA) kit.

In another alternative embodiment, a diagnostic/prognostic device may comprise polymerase chain reaction means for establishing sequence differences of a PDGF-D of a test individual and comparing this sequence structure with that disclosed in this application in order to detect any abnormalities, with a view to establishing whether any aberrations in PDGF-D expression are related to a given disease condition.

In addition, a diagnostic/prognostic device may comprise a restriction length polymorphism (RFLP) generating means utilizing restriction enzymes and genomic DNA from a test individual to generate a pattern of DNA bands on a gel and comparing this pattern with that disclosed in this application in order to detect any abnormalities, with a view to establishing whether any aberrations in PDGF-D expression are related to a given disease condition.

In accordance with a further aspect, the invention relates to a method of detecting aberrations in PDGF-D gene structure in a test subject which may be associated with a disease condition in the test subject. This method comprises providing a DNA sample from said test subject; contacting the DNA sample with a set of primers specific to PDGF-D DNA operatively coupled to a polymerase and selectively amplifying PDGF-D DNA from the sample by polymerase chain reaction, and comparing the nucleotide sequence of the amplified PDGF-D DNA from the sample with the nucleotide sequences shown in FIG. 3 (SEQ ID NO:3), FIG. 5 (SEQ ID NO:5) or FIG. 7 (SEQ ID NO:7). The invention also includes the provision of a test kit comprising a pair of primers specific to PDGF-D DNA operatively coupled to a polymerase, whereby said polymerase is enabled to selectively amplify PDGF-D DNA from a DNA sample.

The invention also provides a method of detecting PDGF-D in a biological sample, comprising the step of contacting the sample with a reagent capable of binding PDGF-D, and detecting the binding. Preferably the reagent capable of binding PDGF-D is an antibody directed against PDGF-D, particularly a monoclonal antibody. In a preferred embodiment the binding and/or extent of binding is detected by means of a detectable label; suitable labels are discussed above.

In another aspect, the invention relates to a protein dimer comprising the PDGF-D polypeptide, particularly a disulfide-linked dimer. The protein dimers of the invention include both homodimers of PDGF-D polypeptide and heterodimers of PDGF-D and VEGF, VEGF-B, VEGF-C, VEGF-D, PlGF, PDGF-A, PDGF-B or PDGF-C.

According to a yet further aspect of the invention there is provided a method for isolation of PDGF-D comprising the step of exposing a cell which expresses PDGF-D to heparin to facilitate release of PDGF-D from the cell, and purifying the thus-released PDGF-D.

Another aspect of the invention involves providing a vector comprising an anti-sense nucleotide sequence which is complementary to at least a part of a DNA sequence which encodes PDGF-D or a fragment or analog thereof that has the biological activity of PDGF-D. In addition the anti-sense nucleotide sequence can be to the promoter region of the PDGF-D gene or other non-coding region of the gene which may be used to inhibit, or at least mitigate, PDGF-D expression.

According to a yet further aspect of the invention such a vector comprising an anti-sense sequence may be used to inhibit, or at least mitigate, PDGF-D expression. The use of a vector of this type to inhibit PDGF-D expression is favored in instances where PDGF-D expression is associated with a disease, for example where tumors produce PDGF-D in order to provide for angiogenesis, or tissue remodeling that takes place during invasion of tumor cells into a normal cell population by primary or metastatic tumor formation. Transformation of such tumor cells with a vector containing an anti-sense nucleotide sequence would suppress or retard angiogenesis, and so would inhibit or retard growth of the tumor or tissue remodeling.

Another aspect of the invention relates to the discovery that the full length PDGF-D protein is likely to be a latent growth factor that needs to be activated by proteolytic processing to release an active PDGF/VEGF homology domain. A putative proteolytic site is found in residues 254–257 in the full length protein, residues -RKSK- (SEQ ID NO:9). This is a dibasic motif. The -RKSK- (SEQ ID NO:9) putative proteolytic site is also found in PDGF-A, PDGF-B, VEGF-C and VEGF-D. In these four proteins, the putative proteolytic site is also found just before the minimal domain for the PDGF/VEGF homology domain. Together these facts indicate that this is the proteolytic site.

Preferred proteases include, but are not limited, to plasmin, Factor X and enterokinase. The N-terminal CUB domain may function as an inhibitory domain which might be used to keep PDGF-D in a latent form in some extracellular compartment and which is removed by limited proteolysis when PDGF-D is needed.

According to this aspect of the invention, a method is provided for producing an activated truncated form of PDGF-D or for regulating receptor-binding specificity of PDGF-D. These methods comprise the steps of expressing an expression vector comprising a polynucleotide encoding a polypeptide having the biological activity of PDGF-D and supplying a proteolytic amount of at least one enzyme for processing the expressed polypeptide to generate the activated truncated form of PDGF-D.

This aspect also includes a method for selectively activating a polypeptide having a growth factor activity. This method comprises the step expressing an expression vector comprising a polynucleotide encoding a polypeptide having a growth factor activity, a CUB domain and a proteolytic site between the polypeptide and the CUB domain, and supplying a proteolytic amount of at least one enzyme for processing the expressed polypeptide to generate the activated polypeptide having a growth factor activity.

In addition, this aspect includes the isolation of a nucleic acid molecule which codes for a polypeptide having the biological activity of PDGF-D and a polypeptide thereof which comprises a proteolytic site having the amino acid sequence RKSK (SEQ ID NO:9) or a structurally conserved amino acid sequence thereof.

Also this aspect includes an isolated dimer comprising an activated monomer of PDGF-D and an activated monomer of VEGF, VEGF-B, VEGF-C, VEGF-D, PDGF-D, PDGF-A, PDGF-B, PDGF-C or PlGF linked to a CUB domain, or alternatively, an activated monomer of VEGF, VEGF-B, VEGF-C, VEGF-D, PDGF-D, PDGF-A, PDGF-B or PlGF and an activated monomer of PDGF-D linked to a CUB domain. The isolated dimer may or may not include a proteolytic site between the activated monomer and the CUB domain.

Polynucleotides of the invention such as those described above, fragments of those polynucleotides, and variants of those polynucleotides with sufficient similarity to the non-coding strand of those polynucleotides to hybridize thereto under stringent conditions all are useful for identifying, purifying, and isolating polynucleotides encoding other, non-human, mammalian forms of PDGF-D. Thus, such polynucleotide fragments and variants are intended as aspects of the invention. Exemplary stringent hybridization conditions are as follows: hybridization at 42° C. in 5×SSC, 20 mM NaPO$_4$, pH 6.8, 50% formamide; and washing at 42° C. in 0.2×SSC. Those skilled in the art understand that it is desirable to vary these conditions empirically based on the length and the GC nucleotide base content of the sequences to be hybridized, and that formulas for determining such variation exist. See for example Sambrook et al, "Molecular Cloning: A Laboratory Manual", Second Edition, pages 9.47–9.51, Cold Spring Harbor, N.Y.: Cold Spring Harbor Laboratory (1989).

Moreover, purified and isolated polynucleotides encoding other, non-human, mammalian PDGF-D forms also are aspects of the invention, as are the polypeptides encoded thereby and antibodies that are specifically immunoreactive with the non-human PDGF-D variants. Thus, the invention includes a purified and isolated mammalian PDGF-D polypeptide and also a purified and isolated polynucleotide encoding such a polypeptide.

It will be clearly understood that nucleic acids and polypeptides of the invention may be prepared by synthetic means or by recombinant means, or may be purified from natural sources.

It will be clearly understood that for the purposes of this specification the word "comprising" means "included but not limited to." The corresponding meaning applies to the word "comprises."

BRIEF DESCRIPTION OF THE DRAWINGS

FIG. 1 (SEQ ID NO:1) shows a nucleotide sequence that includes a cDNA sequence encoding the C-terminal part of human PDGF-D (hPDGF-D). The nucleotides which encode for the partial fragment of hPDGF-D are 1 to 198. The deduced partial amino acid sequence of hPDGF-D (66 amino acid residues-SEQ ID NO:2) derived from nucleotides 1 to 198 of FIG. 1 is shown in FIG. 2;

FIG. 3 (SEQ ID NO:3) shows an extended sequence of a partial human cDNA encoding for the hPDGF-D. The translated cDNA sequence is from nucleotide 1 to 600. The deduced partial amino acid sequence of hPDGF-D (200 residues-SEQ ID NO:4) derived from nucleotides 1 to 600 of FIG. 3 is shown in FIG. 4;

FIG. 5 shows a still further extended nucleotide sequence of a partial human cDNA. The nucleotides which encode for the 5'-truncated full-length hPDGF-D are 1 to 966 (SEQ ID NO:5). The deduced partial amino acid sequence of hPDGF-D (322 residues-SEQ ID NO:6) derived from nucleotides 1 to 966 of FIG. 5 is shown in FIG. 6;

FIG. 7 (SEQ ID NO:7) shows the complete nucleotide sequence of cDNA encoding a hPDGF-D(1116 bp) and the deduced amino acid sequence of full-length hPDGF-D encoded thereby which consists of 370 amino acid residues (FIG. 8-SEQ ID NO:8);

FIG. 9 shows an amino acid sequence alignment of the hPDGF-D with hPDGF-C (SEQ ID NOs:8 and 32, respectively);

FIG. 10 shows an amino acid sequence alignment of the PDGF/VEGF-homology domain in hPDGF-D with several growth factors belonging to the VEGF/PDGF family (SEQ ID NOs:10–18, respectively);

FIG. 24 shows SDS-PAGE analysis under reducing conditions of human PDGF-DD formed from the core domain of factor Xa-digested mutant full-length form of PDGF-D.

FIG. 25 shows the in vivo angiogenic activity of human PDGF-DD and other PDGF isoforms in the mouse cornea pocket assay. In FIG. 25A–E, arrows point to where PDGF protein-containing beads were implanted.

DETAILED DESCRIPTION OF PREFERRED EMBODIMENTS

Figure 11:
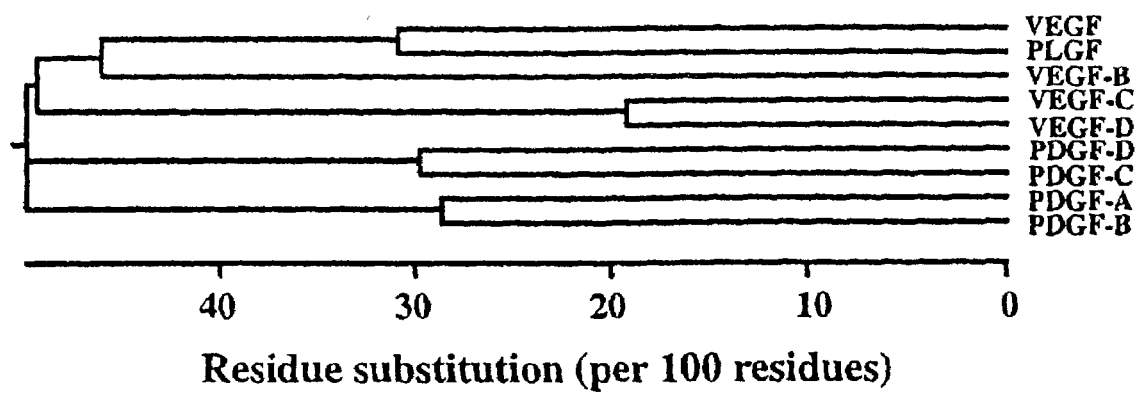
FIG. 11 shows a phylogenetic tree of several growth factors belonging to the VEGF/PDGF family.

FIG. 1 shows a nucleotide sequence of human cDNA which encodes a C-terminal portion of a novel growth factor, referred to herein as PDGF-D (formerly VEGF-G). PDGF-D is a new member of the VEGF/PDGF family. The nucleotide sequence of FIG. 1 (SEQ ID NO:1) was derived from a human EST sequence (id. AI488780) in the dbEST database at the NCBI in Washington, D.C. The nucleotides 1 to 198 of the cDNA of FIG. 1 (SEQ ID NO:1) encodes a 66 amino acid polypeptide (FIG. 2-SEQ ID NO:2) which shows some sequence similarity to the known members of the VEGF/PDGF family.

The amino acid sequence of the polypeptide encoded by the nucleotides 1 to 198 of the polynucleotide of FIG. 1 (SEQ ID NO:1) is shown in FIG. 2 (SEQ ID NO:2).

To generate more sequence information on human PDGF-D, a human fetal lung λgt10 cDNA library was screened using a 327 bp polymerase chain reaction (PCR)-generated probe, based on the originally identified EST sequence. The probe was generated from DNA from a commercially available human fetal lung cDNA library (Clontech) which was amplified by PCR using two primers derived from the identified EST (AI488780). The primers were:

5'-GTCGTGGAACTGTCAACTGG (forward) (SEQ ID NO:26) and

5'-CTCAGCAACCACTTGTGTTC (reverse) (SEQ ID NO:27).

The amplified 327 bp fragment was cloned into the pCR2.1 vector (Invitrogen). Nucleotide sequencing verified that the insert corresponded to the EST. The screen identified several positive clones. The inserts from two of these clones, clones 5 and 8 were subcloned into pBluescript and subjected to nucleotide sequencing using internal or vector-specific primers. The nucleotide sequences determined were identical in both clones and are shown in FIG. 3 (SEQ ID NO:3). The coding region of the 690 bp polynucleotide is nucleotides 1–600 (SEQ ID NO:3) that encodes for a large portion of hPDGF-D with the exception of the 5'-end. This portion of hPDGF-D includes the bioactive fragment of hPDGF-D. The deduced partial amino acid sequence of hPDGF-D (200 residues-SEQ ID NO:4) derived from nucleotides 1 to 600 of FIG. 3 (SEQ ID NO:3) is shown in FIG. 4 (SEQ ID NO:4).

Extended nucleotide sequencing of the isolated human PDGF-D cDNA clones from this human fetal lung cDNA library has provided additional sequence. FIG. 5 (SEQ ID NO:5) shows a nucleotide sequence of a partial human cDNA (1934 bp) that encodes hPDGF-D. The coding region of the 1934 bp polynucleotide is nucleotides 1 to 966 that encodes for hPDGF-D except for the most 5'-end of the polypeptide. The deduced partial amino acid sequence of hPDGF-D (322 residues-SEQ ID NO:6) derived from nucleotides 1 to 966 of FIG. 5 (SEQ ID NO:5) is shown in FIG. 6 (SEQ ID NO:6).

FIG. 7 (SEQ ID NO:7) shows a polynucleotide sequence of cDNA encoding a full-length hPDGF-D. The region encoding PDGF-D is 1116 bp. The deduced amino acid sequence of full-length hPDGF-D is 370 amino acid residues (FIG. 8-SEQ ID NO:8).

The sequence for the 5' end of full-length PDGF-D was obtained using Rapid Amplification of cDNA Ends (RACE) PCR, and clones containing cDNA from the human heart (Marathon-ReadyTM cDNA, Clontech, Cat# 7404-1). These cDNA clones have an adaptor sequence attached to the 5' end of each clone, including a site for primer called Adaptor Primer 1 (Clontech):

5' CCATCCTAATACGACTCACTATAGGGC 3'(SEQ ID NO:28).

This primer and a second primer:

'AGTGGGATCCGTTACTGATGGAGAGTTAT 3' (SEQ ID NO:29)

were used to amplify the sequence found at the 5' end of PDGF-D. In the PCR reaction a special polymerase mix was used (Advantage<<-GC cDNA PCR Kit, Clontech, Cat# K1907-1). The reaction mix included (in microliters):

| Adaptor Primer 1 | |
|---|---|
| Gene specific primers | 1 each |
| Template (Human Heart cDNA) | 5 |
| GC-Melt (from the K1907-1 Kit) | 5 |
| 5xGC cDNA PCR Reaction Buffer | 10 |
| 50x dNTP mix | 1 |
| Sterile H$_2$O | 27 |
| Total | 50 |

The 5' end of PDGF-D was amplified for 31 cycles, five cycles consisted of 45 seconds denaturation at 94° C. and four minutes extension at 72° C., five cycles consisted of 45 seconds denaturation at 94° C. and four minutes extension at 70° C., and twenty-one cycles consisted of 45 seconds denaturation at 94° C. and four minutes extension at 68° C. and an initial denaturation step at 94° C. for two minutes. From this PCR, an approximately 790 bp long product was obtained. This product was run on a 1% agarose gel, purified (QIAquick gel extraction Kit, Qiagen, Cat # 28706) from the gel, cloned into a vector (TOPO TA Cloning Kit, Invitrogen) and transformed into bacteria (*E. Coli*). Transformed bacteria were plated, and incubated at 37° C. overnight. Single colonies were picked and grown in fresh media overnight. Plasmids were prepared (QIAprep Spin Miniprep Kit, Qiagen, Cat# 27106) and sequenced with the plasmid primers, T7 and M13R. The result of this sequencing was that 312 bp of previously unknown PDGF-D sequence was obtained. The rest of the sequence (478 bp) was identical with previously obtained sequence from other PDGF-D cDNA clones.

Figure 9:
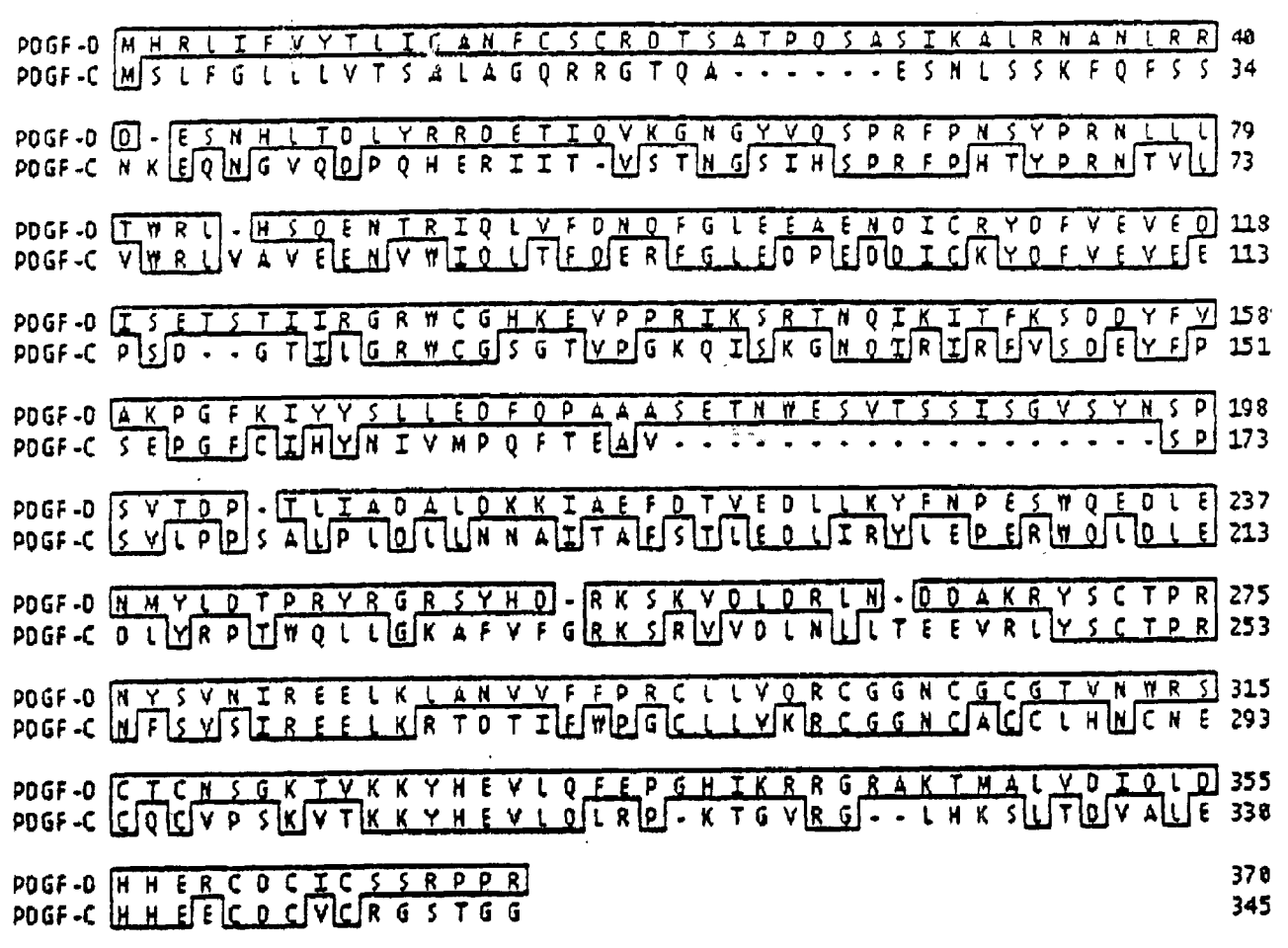

Similar to PDGF-C, PDGF-D has a two domain structure with a N-terminal CUB domain (residues 67–167, discussed below) and a C-terminal PDGF/VEGF homology domain (residues 272–362, the core domain). The overall amino acid sequence identity between PDGF-C (SEQ ID NO:32) and PDGF-D (SEQ ID NO:8) is approximately 43% (FIG. 9). The similarities are highest in the distinct protein domains while the N-terminal region, including the hydrophobic signal sequence, and the hinge region between the two domains display lower identities. A putative signal peptidase cleavage site was identified between residues 22–23. Cleavage results in a protein of 348 residue with a calculated molecular mass ($M_r$) of 44,000. A single putative site for N-linked glycosylation was identified in the core domain of PDGF-D (residues 276–278).

Figure 10:
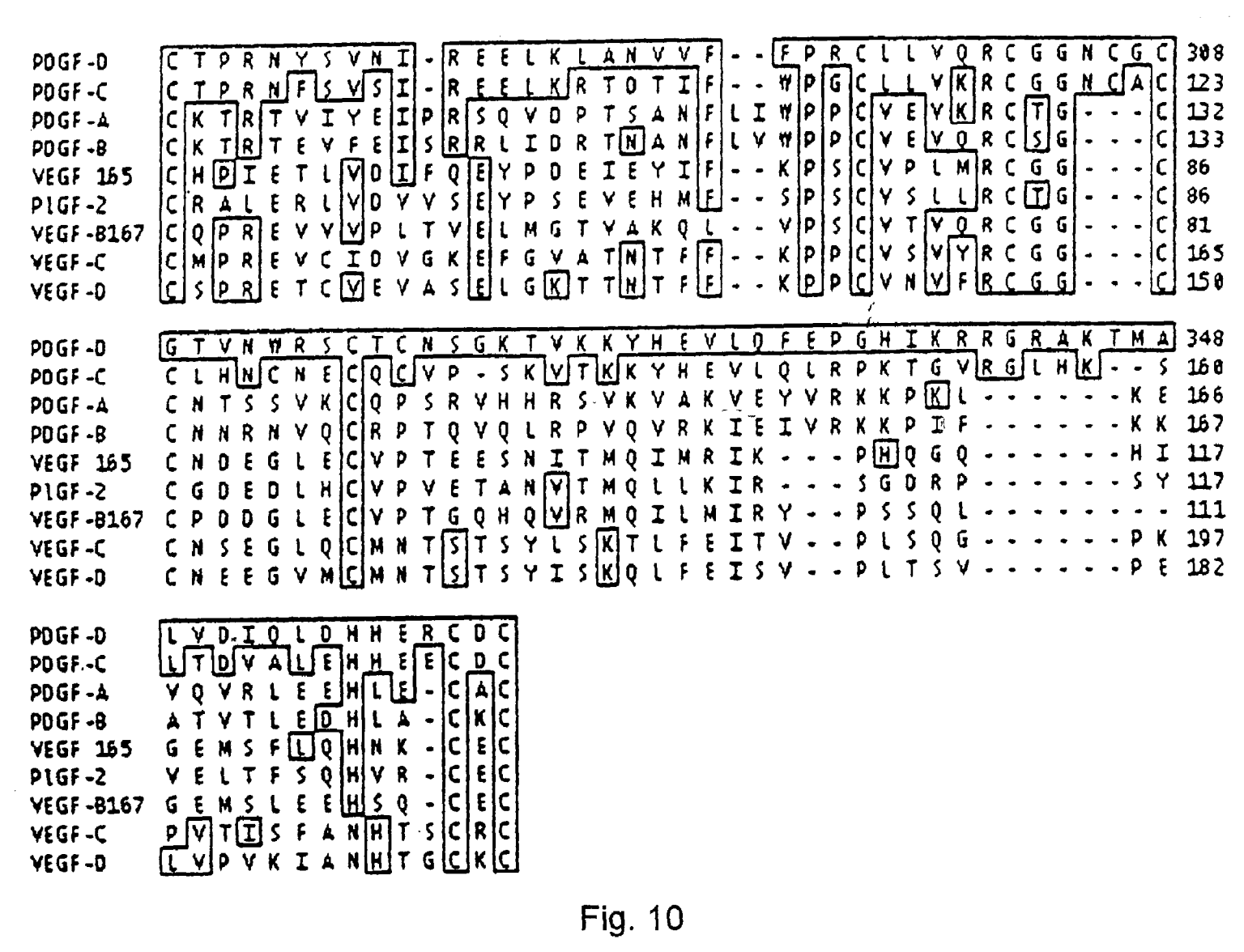

FIG. 10 shows the amino acid sequence alignment of the PDGF/VEGF-homology domain of PDGF-D (found in the C-terminal region of the polypeptide) with the PDGF/VEGF-homology domains of PDGF/VEGF family members, PDGF-C, PDGF-A, PDGF-B, $VEGF_{165}$, PlGF-2, $VEGF-B_{167}$, VEGF-C and VEGF-D (SEQ ID NOs:10–18, respectively). Gaps were introduced to optimize the alignment. This alignment was generated using the MEGALIGN alignment tool based on the method of J. Hein, (1990, *Methods Enzymol.* 183:626–45) The PAM 250 residue weight table is used with a gap penalty of eleven and a gap length penalty of three and a K-tuple value of two in the pairwise alignments. The alignment is then refined manually, and the number of identities are estimated in the regions available for a comparison.

The alignment shows that the core domain of PDGF-D displays about a 50% identity to the corresponding domain in PDGF-C, and about a 20–23% identity to the core domains in the classical PDGFs and VEGFs. It also shows that, with two exceptions, PDGF-D has the expected pattern of invariant cysteine residues, involved in inter- and intra-disulfide bonding, a hallmark of members of this family. The first exception occurs between cysteine 3 and 4. Normally these two cysteines are spaced by 2 residues. However, similar to PDGF-C, PDGF-D has an unique insertion of three additional amino acids residues, NCG. In total, ten cysteine residues reside in the core domain, including the extreme C-terminal region, suggesting a unique arrangement of the cysteines in the disulfide-bonded PDGF-D dimer. The second exception is that the invariant fifth cysteine found in the other members of the PDGF/VEGF family is not conserved in PDGF-D. This feature is unique to PDGF-D.

Based on the amino acid sequence alignments in FIG. 10, a phylogenetic tree was constructed and is shown in FIG. 11. The data show that the PDGF/VEGF homology domain of PDGF-D forms a subgroup of the PDGFs together with PDGF-C.

CUB Domain

Figure 12:
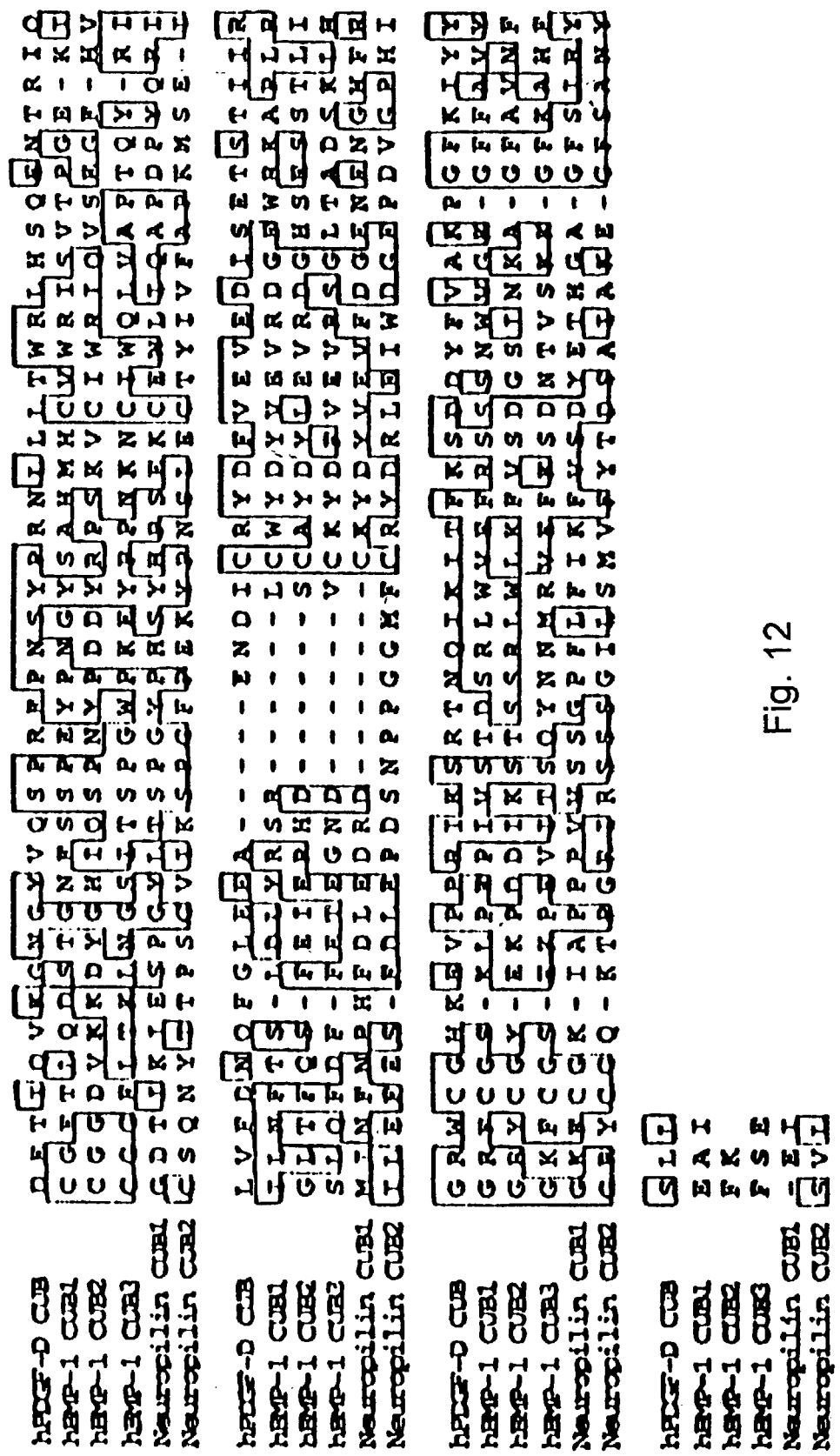
FIG. 12 provides the amino acid sequence alignment of the CUB domain present in hPDGF-D (SEQ ID NO:19) and other CUB domains present in human bone morphogenic protein-1 (hBMP-1, 3 CUB domains CUB1–3) (SEQ ID NOs:20–22, respectively) and in human neuropilin-1 (2 CUB domains) (SEQ ID NOs:23–24, respectively)

The N-terminal region of the partial PDGF-D amino acid sequence of FIG. 12 (residues 53–170 of SEQ ID NO:8) has a second distinct protein domain which is referred to as a CUB domain (Bork and Beckmann, 1993, *J. Mol. Biol.* 231:539–545). This domain of about 115 amino acids was originally identified in complement factors C1r/C1s, but has recently been identified in several other extracellular proteins including signaling molecules such as bone morphogenic protein 1 (BMP-1) (Wozney et al., 1988, *Science*, 242:1528–1534) as well as in several receptor molecules such as neuropilin-1 (NP-1) (Soker et al., 1998, *Cell* 92:735–745). The functional roles of CUB domains are not clear but they may participate in protein-protein interactions or in interactions with carbohydrates including heparin sulfate proteoglycans. These interactions may play a role in the proteolytic activation of PDGF-D.

As shown in FIG. 12, the amino acid sequences from several CUB-containing proteins were aligned. The results show that the single CUB domain in human PDGF-D (SEQ ID NO:19) displays a significant identify with the most closely related CUB domains. Sequences from human BMP-1, with 3 CUB domains (CUBs1–3) (SEQ ID NOs: 20–22, respectively) and human neuropilin-1 with 2 CUB domains (CUBs1–2) (SEQ ID NOs: 23–24, respectively) are shown. This alignment was generated as described above.

EXAMPLE 1

Expression of Human PDGF-D in Baculovirus Infected Sf9 Cells

The portion of the cDNA encoding amino acid residues 24–370 of SEQ ID NO:8 was amplified by PCR using Taq DNA polymerase (Biolabs). The forward primer used was 5'GATATCTAGAAGCAACCCCGCAGAGC 3' (SEQ ID NO:33). This primer includes a XbaI site (underlined) for in frame cloning. The reverse primer used was 5' GCTC GAATTCTAAATGGTGATGGTGATGATG TCGAGGTG-GTCTTGA 3' (SEQ ID NO:34). This primer includes an EcoRI site (underlined) and sequences coding for a C-terminal 6× His tag preceded by an enterokinase site. The PCR product was digested with XbaI and EcoRI and subsequently cloned into the baculovirus expression vector, pAcGP67A. Verification of the correct sequence of the cloned PCR product was done by nucleotide sequencing. The expression vectors were then co-transfected with BaculoGold linearized baculovirus DNA into Sf9 insect cells according to the manufacturer's protocol (Pharmingen). Recombined baculovirus were amplified several times before beginning large scale protein production and protein purification according to the manual (Pharmingen).

Sf9 cells, adapted to serum free medium, were infected with recombinant baculovirus at a multiplicity of infection of about seven. Media containing the recombinant proteins were harvested four days after infection and were incubated with Ni-NTA-Agarose beads(Qiagen). The beads were collected in a column and after extensive washing with 50 mM sodium phosphate buffer pH 8, containing 300 mM NaCl (the washing buffer), the bound proteins were eluted with increasing concentrations of imidazole (from 100 mM to 500 mM) in the washing buffer. The eluted proteins were analyzed by SDS-PAGE using 12.5% polyacrylamide gels under reducing and non-reducing conditions.

Figure 13:
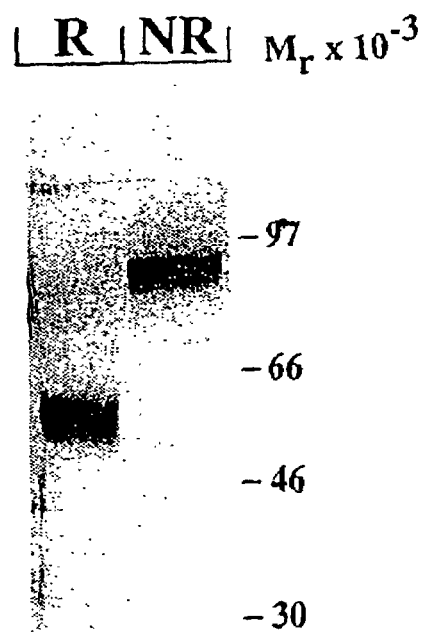
FIG. 13 shows the results of the SDS-PAGE analysis of human recombinant PDGF-D under reducing (R) and non-reducing (NR) conditions.

FIG. 13 shows the results of the SDS-PAGE analysis of human recombinant PDGF-D under reducing (R) and non-reducing (NR) conditions. PDGF-D was visualized by staining with Coomassie Brilliant Blue. FIG. 13 also shows that the recombinant PDGF-D migrates as a 90 kDa species under non-reducing conditions and as a 55 kDa species under reducing conditions. This indicates that the protein was expressed as a disulfide-linked homodimer.

EXAMPLE 2

Generation of Antibodies to Human PDGF-D

Rabbit antisera against full-length PDGF-DD and against a synthetic peptide derived from the PDGF-D sequence (residues 254–272, amino acid sequence RKSKVDLDRLNDDAKRYSC of SEQ ID NO:36 were generated. These peptides were each conjugated to the carrier protein keyhole limpet hemocyanin (KLH, Calbiochem) using N-succinimidyl 3-(2-pyridyldithio)propionate (SPDP) (Pharmacia Inc.) according to the instructions of the supplier. 200–300 micrograms of the conjugates in phosphate buffered saline (PBS) were separately emulsified in Freunds Complete Adjuvant and injected subcutaneously at multiple sites in rabbits. The rabbits were boostered subcutaneously at biweekly intervals with the same amount of the conjugates emulsified in Freunds Incomplete Adjuvant. Blood was drawn and collected from the rabbits. The sera were prepared using standard procedures known to those skilled in the art. The antibodies to full-length PDGF-DD were affinity-purified on a column of purified PDGF-DD coupled to CNBr-activated Sepharose 4B (Pharmacia).

Figure 14:
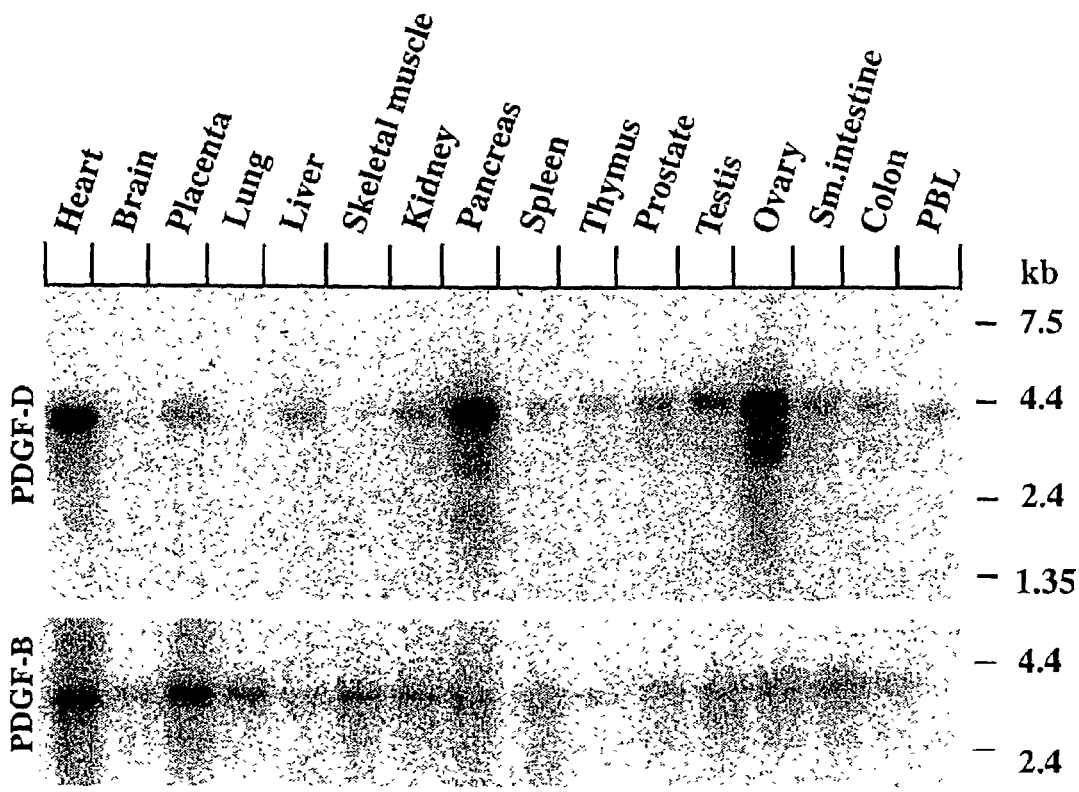
FIG. 14 shows the results of the immunoblot analysis of full-length PDGF-D and PDGF-C under reducing and non-reducing conditions employing affinity-purified rabbit antibodies to full-length PDGF-D.

As seen in FIG. 14, the antibodies did not cross-react with PDGF-C in the immunoblot analysis. For immunoblotting analyses, the proteins were electrotransferred onto Hybond filters for 45 minutes.

EXAMPLE 3

Expression of PDGF-D Transcripts

Figure 15:
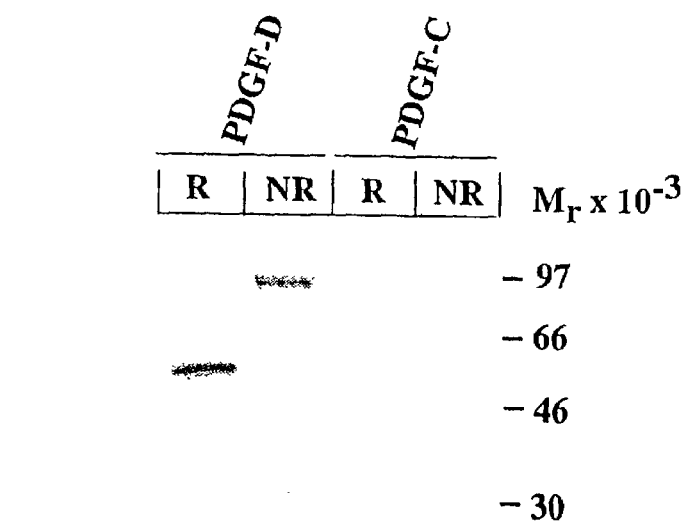
FIG. 15 provides that results of the relative expression levels of PDGF-D (upper panel) and PDGF-B (lower panel) transcripts in several human tissues as determined by Northern Blot analysis.

To investigate the tissue expression of PDGF-D in several human tissues, a Northern blot was done using a commercial Multiple Tissue Northern blot (MTN, Clontech). The blots were hybridized at according to the instructions from the supplier using ExpressHyb solution at 68° C. for one hour (high stringency conditions), and probed sequentially with a $^{32}$P-labeled 327 bp PCR-generated probe from the human fetal lung cDNA library (see description above) and full-length PDGF-B cDNA. The blots were subsequently washed at 50° C. in 2×SSC with 0.05% SDS for 30 minutes and at 50° C. in 0.1×SSC with 0.1% SDS for an additional 40 minutes. The blots were then put on film and exposed at −70° C. As shown in FIG. 15, upper panel, the highest expression of a major 4.4 kilobase (kb) transcript occurred in heart, pancreas and ovary while lower expression levels were noted in several other tissues including placenta, liver, kidney, prostate, testis, small intestine, spleen and colon. No expression was detected in brain, lung, or skeletal muscle. In comparison, the 3.5 kb PDGF-B transcript was abundantly expressed in heart and placenta, whereas lower levels were observed in all other tissues (FIG. 15, lower panel). Prominent co-expression of PDGF-D and PDGF-B occurred in heart, pancreas and ovary.

EXAMPLE 4

Immunohistochemistry Localization of VEGF-D in Mouse Embryos

The spatial and temporal patterns of expression of the PDGF-D protein in mouse embryos were determined by immunohistochemistry using standard procedures and employing affinity-purified rabbit antibodies to full-length PDGF-DD generated in Example 2 on tissue sections of embryos during midgestation (embryonic day (E) 14.5). The embryos were fixed in 4% paraformaldehyde overnight at 4° C. and processed for cryosectioning. 14 μm cryosections were used for the stainings. Paraffin-embedded sections which were prepared by routine procedures were also used. After sectioning, the slides were air dried for one to three hours followed by a ten minute post fixation with 4% paraformaldehyde. After washing 3×5 minutes with phosphate buffered saline (PBS) containing 0.3% Triton X-100 (PBS-T), the slides were incubated in 0.3% $H_2O_2$ in PBS-T for 30 minutes to quench the endogenous peroxidase activity. This was followed by washing 2×5 minutes with PBS-T and 2×5 minutes in PBS. Blocking of non-specific binding was done using 3% bovine serum albumin (BSA) in PBS for 30 minutes. The slides were incubated with the affinity purified antibody to human PDGF-DD (3–9 mg of Ig/ml) overnight at 4° C. After washing, the slides were incubated with the secondary Ig (goat anti-rabbit HRP, Vector Laboratories) at a dilution of 1:200 for one hour. After washing, the slides were incubated with the AB complex (Vector Laboratories) for one hour and washed with Tris pH 7.4. Either 3,3'-diaminobenzidine tetrahydrochloride (DAB from SIGMA) or 3-amino-9-ethyl carbazole (AEC from Vector Laboratories) was used for color development. The reaction was quenched by washing in Tris-HCl buffer. In control experiments the antibodies were preincubated with a 30× molar excess of full-length PDGF-DD. This blocked the staining, while a similar preincubation with full-length PDGF-CC did not affect the staining of the tissue sections. The photomicrographs were taken using a Zeiss microscope equipped with differential interference contrast optics.

Figure 16:
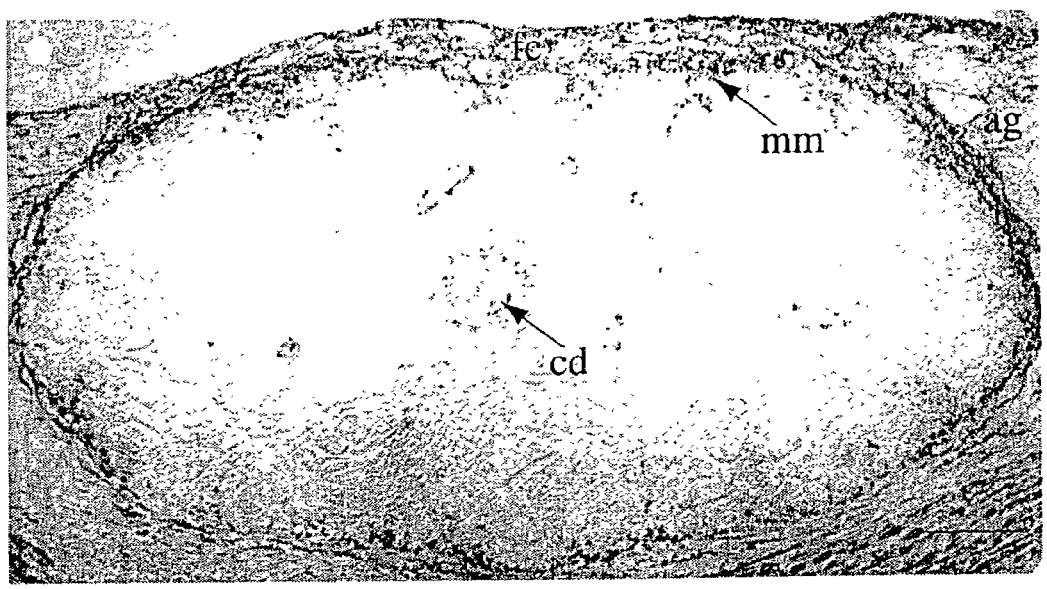
FIG. 16 shows PDGF-D expression in the developing kidney of a mouse embryo.
Figure 17:
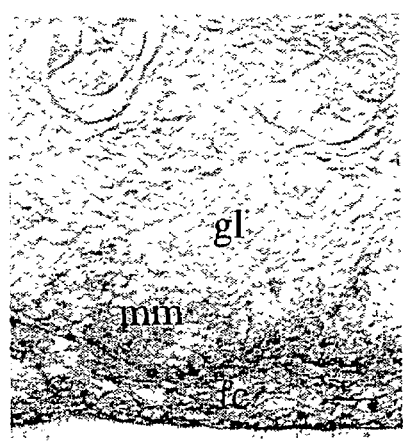
FIG. 17 shows a more detailed view of PDGF-D expression in the developing kidney of a mouse embryo.
Figure 18:
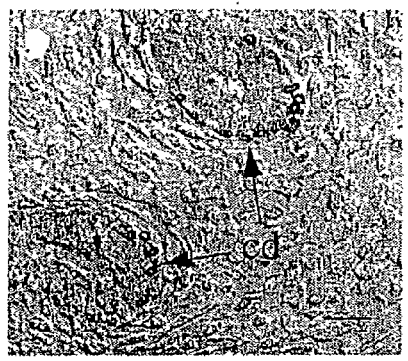
FIG. 18 shows a more detailed view of PDGF-D expression in the developing kidney of a mouse embryo.

Intense staining for PDGF-D was noted in the developing heart, lung, kidney and some muscle derivatives. FIGS. 16–18 show the staining of the embryonic kidney. Intense staining of the highly vascularized fibrous capsule (fc) surrounding the kidney, the adjacent adrenal gland (ag), and in the most peripheral aspect of the metanephric mesenchyme (mm) of the cortex was observed (FIGS. 16 and 17). Staining was also observed in cells located in the basal aspect of the branching ureter (FIG. 18), while the developing nephron, including the ureter buds, glomeruli (gl) and Henle's loops, were negative. Previous analysis have shown that PDGFR-beta is expressed by the metanephric mesenchyme and the developing vascular smooth muscle cells and mesangial cells of the developing renal cortex. In contrast, renal expression of PDGF-B is restricted to endothelial cells (Lindahl, P. et al., 1998, *Development* 125:3313–3322). The non-overlapping patterns of expression of the two PDGFR-beta ligands suggests that PDGF-B and PDGF-D provide distinct signals to PDGFR-beta expressing perivascular cells. This differential localization indicates that PDGF-D might have a paracrine role in the proliferation and/or commitment of PDGFR-beta expressing perivascular progenitor cells of the undifferentiated metanephric mesenchyme. In line with the phenotype of PDGF-B deficient mice, PDGF-B may then provide proliferative signals and spatial clues of the branching vascular tree of the kidney, thus allowing proliferation and co-recruitment of the PDGFR-beta expressing perivascular cells to form the mesangium of the glomeruli, and the smooth muscle cells of the efferent and afferent arterioles.

The expression of PDGF-D partially overlaps with the expression of PDGF-C in the cortical area of the developing kidney. The different receptor specificities of PDGF-C and PDGF-D and their apparent inability to form heterodimers indicate that the two novel PDGFs may provide distinct signals for migration and proliferation for at least two different cell populations in the undifferentiated metanephric mesenchyme; either interstitial cell progenitors expressing PDGF alpha-receptor, or the PDGFR-beta expressing perivascular progenitor cells.

The phenotypic differences in the kidneys of mice lacking PDGFR-alpha and PDGF-A argue for a unique role of PDGF-C in the formation of the renal mesenchyme. Interestingly, a comparison of the PDGFR-beta and PDGF-B deficient mice have not revealed a similar phenotypic discrepancy arguing for, at least partially, redundant roles of PDGF-D and PDGF-B during early stages of kidney development.

EXAMPLE 5

Receptor Binding Properties of PDGF-D with the VEGF Receptors

To assess the interactions between PDGF-D and the VEGF receptors, truncated PDGF-D was tested for its capacity to bind to soluble Ig-fusion proteins containing the extracellular domains of human VEGFR-1, VEGFR-2 and VEGFR-3 (Olofsson et al., 1998, *Proc. Natl. Acad. Sci. USA* 95:11709–11714). An expression vector encoding the PDGF/VEGF homology domain of PDGF-D was generated in the vector pSecTag (Invitrogen). The primers 5'-CCCAAGCTTGAAGATCTTGAGAATAT 3' (forward) (SEQ ID NO:30) and 5'-TGCTCTAGATCGAGGTG-GTCTT 3' (reverse) (SEQ ID NO:31) were used to amplify a 429 bp fragment (nucleotides 556 to 966 in FIG. 5) (SEQ ID NO:5) encoding amino acid residues 186 to 322 of FIG. 6 (SEQ ID NO:6). The fragment was subsequently cloned into a HindIII and XbaI digested expression vector. COS cells were transfected with the expression vector encoding truncated PDGF-D or a control vector using calcium phosphate precipitation. The expressed polypeptide included a C-terminal c-myc tag and a 6× His tag (both derived from the pSecTag vector).

The Ig-fusion proteins, designated VEGFR-1-Ig, VEGFR-2-Ig and VEGFR-3-Ig, were transiently expressed in human 293 EBNA cells. All Ig-fusion proteins were human VEGFRs. Cells were incubated for 24 hours after transfection, washed with Dulbecco's Modified Eagle Medium (DMEM) containing 0.2% bovine serum albumin (BSA) and starved for 24 hours. The fusion proteins were then precipitated from the clarified conditioned medium using protein A-Sepharose beads (Pharmacia). The beads were combined with 100 microliters of 10× binding buffer (5% BSA, 0.2% Tween 20 and 10 µg/ml heparin) and 900 microliter of conditioned medium prepared from the COS cells transfected with the expression vector for truncated PDGF-D or the control vector. The cells were then metabolically labeled with $^{35}$S-cysteine and methionine (Promix, Amersham) for 4 to 6 hours. After 2.5 hours at room temperature, the Sepharose beads were washed three times with binding buffer at 4° C., once with phosphate buffered saline (PBS) and boiled in SDS-PAGE buffer. Labeled proteins that were bound to the Ig-fusion proteins were analyzed by SDS-PAGE under reducing conditions. Radiolabeled proteins were detected using a phosphorimager analyzer and/or on film. In all these analyses, radiolabeled PDGF-D failed to show any interaction with any of the VEGF receptors. These results indicate that secreted truncated PDGF-D does not bind to VEGF receptors R1, R2 and R3.

EXAMPLE 6

PDGFR-beta Phosphorylation

To test if PDGF-D causes increased phosphorylation of the PDGFR-beta, full-length and plasmin-digested PDGF-D were tested for their capacity to bind to the PDGFR-beta and stimulate increased phosphorylation.

A plasmin-digested preparation of PDGF-DD was generated and analyzed since it is known that plasmin-digestion of full-length PDGF-CC releases the core domain and thus allow the ligand to interact with the receptor. Full length PDGF-DD was digested with plasmin in 20 mM Tris-HCl (pH 7.5) containing 1 mM $CaCl_2$, 1 mM $MgCl_2$ and 0.01% Tween 20 for 1.5 to 4.5 hours at 37° C. using two to three units of plasmin (Sigma) per ml.

Analysis of the plasmin-digested preparation of PDGF-DD by SDS-PAGE under reducing conditions showed two prominent bands of 28 kDa and 15 kDa. The 15 kDa band was identified as the core domain due to its immunoreactivity in immunoblotting with a peptide antiserum raised against a sequence of PDGF-D just N-terminal of the first cysteine residue in the core domain.

Figure 19:
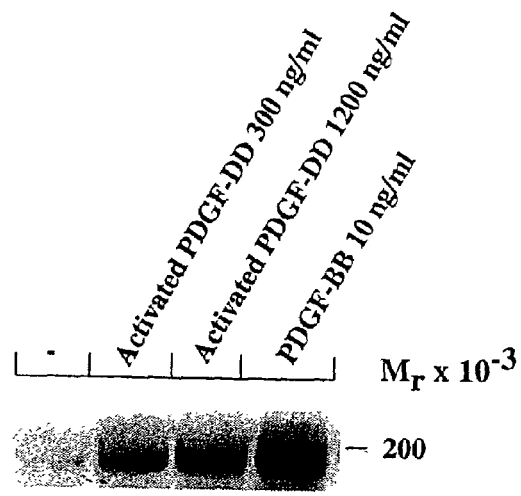
FIG. 19 shows that conditioned medium(CM)containing plasmin-digested PDGF-D stimulates tyrosine phosphorylation of PDGFR-beta in PAE-1 cells.

Serum-starved porcine aortic endothelial-1 (PAE-1) cells stably expressing the human PDGFR-beta (Eriksson et al., 1992, *EMBO J.* 11:543–550) were incubated on ice for 90 minutes with a solution of conditioned media mixed with an equal volume of PBS supplemented with 1 mg/ml BSA and 10 ng/ml of PDGF-BB, 300 ng/ml or 1200 ng/ml of full length human PDGF-DD homodimers or 300 ng/ml or 1200 ng/ml of digested PDGF-DD. The full length and digested PDGF-DD homodimers were produced as described above. Sixty minutes after the addition of the polypeptides, the cells were lysed in lysis buffer (20 mM tris-HCl, pH 7.5, 0.5% Triton X-100, 0.5% deoxycholic acid, 10 mM EDTA, 1 mM orthovanadate, 1 mM PMSF 1% Trasylol). The PDGFR-beta were immunoprecipitated from cleared lysates with rabbit antisera against the human PDGFR-beta (Eriksson et al., 1992, supra). The precipitated receptors were applied to a SDS-PAGE gel. After SDS gel electrophoresis, the precipitated receptors were transferred to nitrocellulose filters, and the filters were probed with anti-phosphotyrosine antibody PY-20, (Transduction Laboratories). The filters were then incubated with horseradish peroxidase-conjugated anti-mouse antibodies. Bound antibodies were detected using enhanced chemiluminescence (ECL, Amersham Inc). The filters were then stripped and reprobed with the PDGFR-beta rabbit antisera, and the amount of receptors was determined by incubation with horseradish peroxidase-conjugated anti-rabbit antibodies. Bound antibodies were detected using enhanced chemiluminescence (ECL, Amersham Inc). The probing of the filters with PDGFR-beta antibodies confirmed that equal amounts of the receptor were present in all lanes. Human recombinant PDGF-BB (100 ng/ml) and untreated cells were included in the experiment as a control. FIG. 19 shows plasmin-digested PDGF-DD efficiently induced PDGFR-beta tyrosine phosphorylation. Full-length PDGF-DD failed to induce PDGFR-beta tyrosine phosphorylation. PDGF-BB was included in the experiment as a positive control. This indicates that plasmin-digested PDGF-D is a PDGFR-beta ligand/agonist.

EXAMPLE 7

Competitive Binding Assay

Next, full length and plasmin-digested PDGF-D were tested for their capacity to bind to human PDGF alpha- and beta-receptors by analyzing their abilities to compete with PDGF-BB for binding to the PDGF receptors. The binding experiments were performed on porcine aortic endothelial-1 (PAE-1) cells stably expressing the human PDGF alpha- and beta-receptors, respectively (Eriksson et al., 1992, supra). Binding experiments were performed essentially as in Heldin et al. (1998, *EMBO J.* 7:1387–1393). Different concentrations of human full-length and plasmin-digested PDGF-DD, or human PDGF-BB were mixed with 5 ng/ml of $^{125}$I-PDGF-BB in binding buffer (PBS containing 1 mg/ml of bovine serum albumin). Aliquots were incubated with the receptor expressing PAE-1 cells plated in 24-well culture dishes on ice for 90 minutes. After three washes with binding buffer, cell-bound $^{125}$I-PDGF-BB or $^{125}$I-PDGF-AA was extracted by lysis of cells in 20 mM Tris-HCl, pH 7.5, 10% glycerol, 1% Triton X-100. The amount of cell bound radioactivity was determined in a gamma-counter. An increasing excess of the unlabeled protein added to the incubations competed efficiently with cell association of the radiolabeled tracer.

Figure 20:
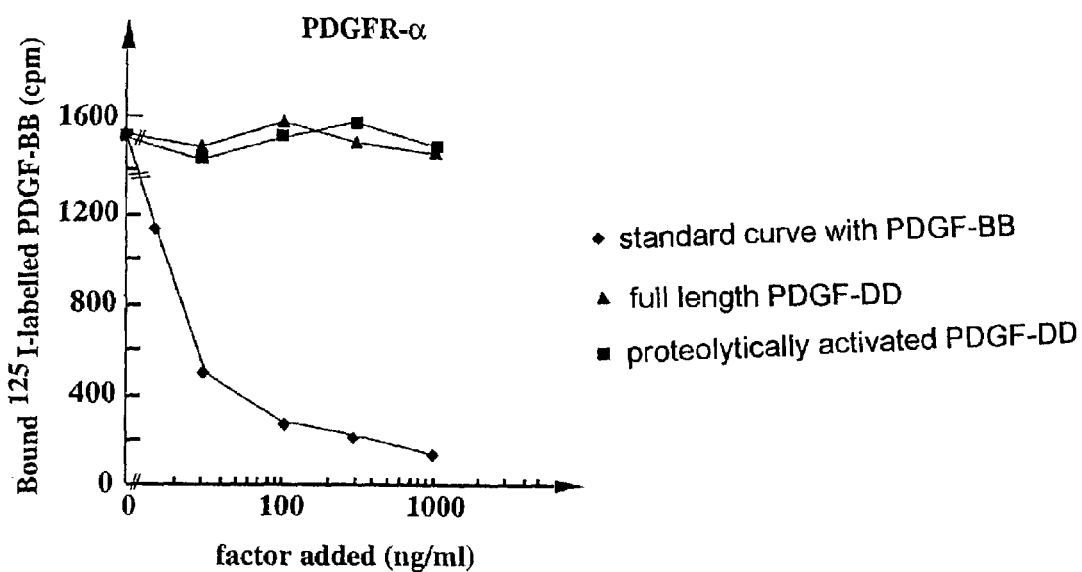
FIG. 20 provides a graphical representation of the results of the competitive binding assay between plasmin-digested PDGF-D and PDGF-BB homodimers for the PDGFRs-beta.
Figure 21:
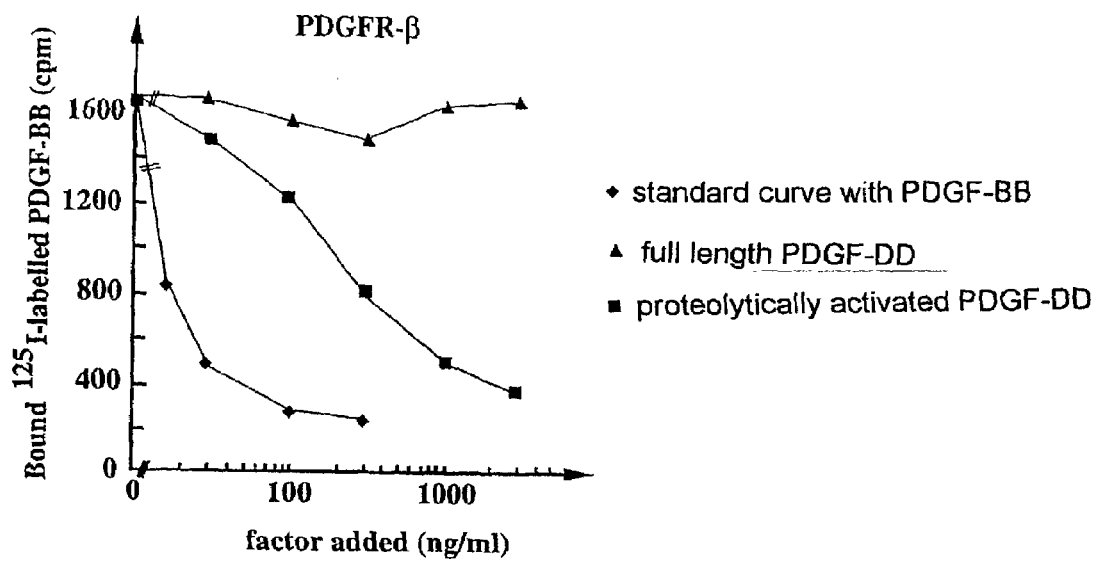
FIG. 21 provides a graphical representation of the results of the competitive binding assay between plasmin-digested PDGF-D and PDGF-AA homodimers for the PDGFRs-alpha.

FIG. 20 provides a graphical representation of results which show that conditioned medium containing plasmin-digested PDGF-DD competes for binding with PDGF-BB homodimers for the PDGFRs-beta, while the full length protein did not. Compared to PDGF-BB, plasmin-activated PDGF-DD appeared 10–12 fold less efficient as a competitor; probably a result of suboptimal activation of the recombinant protein in vitro by the protease. Control experiments showed that plasmin present in the digested PDGF-DD fraction did not affect the binding of $^{125}$I-labelled PDGF-BB to the PDGFR-β-expressing cells. Both the full length and plasmin-digested PDGF-DD proteins failed to compete for binding to the PDGFR-alpha (FIG. 21).

These studies indicate that PDGF-DD is a PDGFR-beta-specific agonist and that proteolytic processing releases the core domains of PDGF-DD from the N-terminal CUB domains which is necessary for unmasking the receptor-binding epitopes of the core domain similar to the situation for PDGF-CC.

EXAMPLE 8

Determination of Alternative Splicing of Murine PDGF-D

Primers were designed for the amplification of the whole coding area of murine PDGF-D by PCR from mouse heart cDNA (Clontech). These primers were: 5'-CAAATG-CAACGGCTCGTTT-3' (SEQ ID NO:41) and 5'-GATATTTGCTTCTTCTTGCCATGG-3' (SEQ ID NO:42). PCR reaction conditions were as follows: PCR Cycles: 94° C. for 2 minutes, followed by 30 cycles: 94° C. for 45 seconds, 62° C. for 45 seconds, 72° C. for 90 seconds, and 72° C. for 7 minutes.

The expected product from this reaction was a 1.2 kb cDNA fragment. However, the product was two bands, one approximately 1.2 kb and the other only 1.0 kb. These two products were checked in a 1% agarose gel, purified from the gel (QIAquick Gel Extraction Kit, Qiagen, Cat # 28706), cloned into a vector (TOPO TA Cloning Kit, Invitrogen), and transformed into *E. Coli* bacteria.

Transformed bacteria were plated and incubated at 37° C. overnight. The next morning some single colonies were picked and grown in fresh medium overnight. Plasmids were prepared (QIAprep Spin Miniprep Kit, Qiagen, Cat # 27106) and sequenced with plasmid primers T7 and M13R, and also with mPDGF-D specific primers. The results revealed three different types of murine PDGF-D cDNAs, one being completely identical with the earlier mouse clones, depicted in SEQ ID NO: 35.

Figure 22A:
FIG. 22A shows a schematic representation of the PDGF-D sequence of SEQ ID NO:35.
Figure 22B:
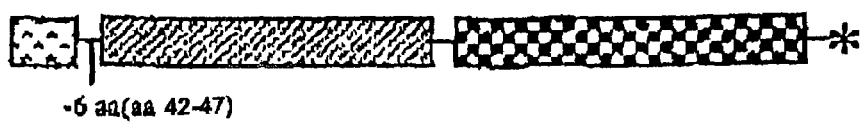
FIG. 22B shows a schematic representation of the PDGF-D sequence variant of SEQ ID NO:37, which corresponds to FIG. 22A but for 6 missing amino acid residues.
Figure 22C:
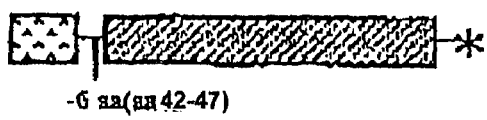
FIG. 22C shows a schematic representation of the PDGF-D sequence variant of SEQ ID NO:39, which corresponds to FIG. 22A but for 6 missing amino acid residues and the loss of a CUB domain in this sequence variant.

The second clone was almost identical to the earlier mouse sequence, however, it lacked six amino acid residues (aa 42–47) from the region between the signal sequence and the CUB domain. The second clone is depicted in SEQ ID NO:37. The third clone was comprised of part of the earlier mouse sequence, lacking amino acids 42–47 as in the second clone, and also lacking the PDGF-homology domain. The third clone is depicted in SEQ ID NO:39. The similarities and differences between regions of the three clones are depicted in FIG. 22.

The surprising results show that at least two alternatively spliced versions of the PDGF-D gene are transcribed into polyadenylated RNA. The variant transcript structures suggest an alternative splice acceptor site is used in exon two, producing a variant protein lacking six amino acid residues (ESNHLT).

Figure 23:
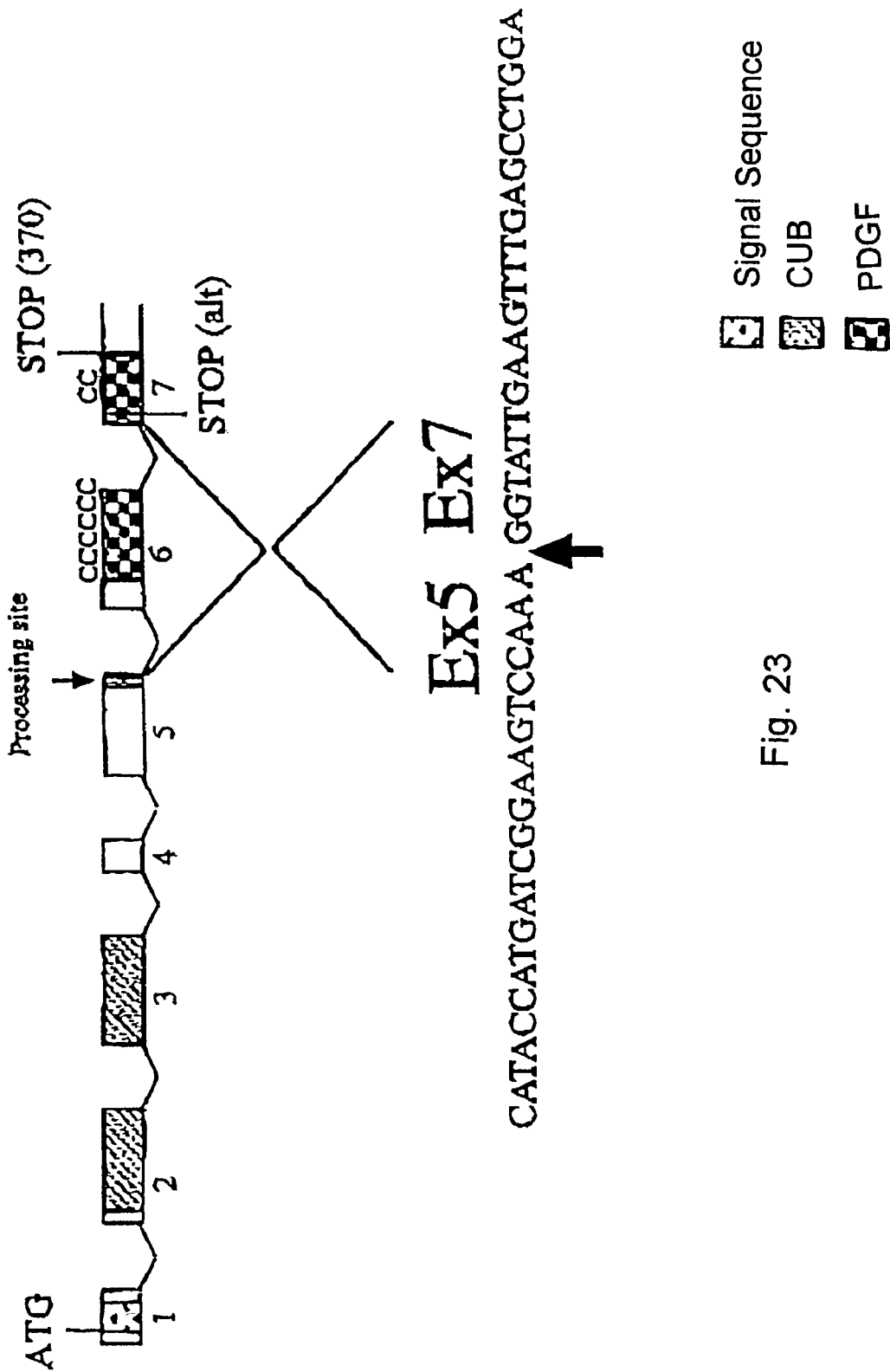
FIG. 23 shows a schematic representation of the PDGF-D sequence, noting the spliced region from exon 5 to exon 7, removal of which yields the PDGF-D sequence variant of SEQ ID NO:39.

In addition to lacking the above noted six amino acid residues, the third clone also lacks the PDGF-homology domain. This is because of the skipping of exon six and the resulting frameshift. This ends the open reading frame in a stop codon after four additional amino acid residues (GIEV). As shown in detail in FIG. 23, this splice variant only contains the amino terminal CUB domain and could potentially provide an inhibitor of PDGF-D functions. The potential inhibition function is because the activation of full-length PDGF-D binding to the PDGFR-D requires proteolytic removal of the CUB domain.

EXAMPLE 9

Generation of Recombinant Human PDGF-DD Core Domain

Figure 24:
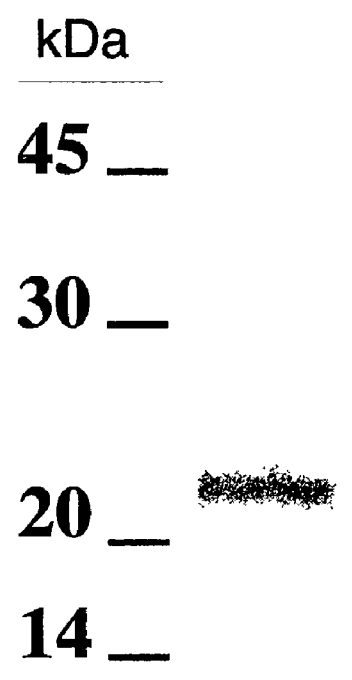

The process as described (Bergsten et al., 2001, *Nat. Cell Biol.* 3:512–516) was followed to generate recombinant human PDGF-DD core domain. Human PDGF-DD was expressed as a mutant full-length form containing a factor Xa protease cleavage site that allowed the generation of the active C-terminal fragment of the protein (PDGF-homology domain) upon cleavage with factor Xa. The recombinant protein has an extreme C-terminal His$_6$-tag to allow its purification on a nickel-containing resin. Following purification, the protein solution was dialyzed against 0.1M acetic acid and lyophilized. SDS-PAGE analysis under reducing conditions on the purified protein revealed that it migrated as a homogenous 21 kDa species (FIG. 24). The purified protein was lyophilized for storage.

EXAMPLE 10

Comparison of Angiogenic Activities of the Human PDGF-DD Core Domain with Other PDGF Isoforms.

The mouse corneal micropocket assay was performed according to procedures described in Cao et al., 1998, *Proc Natl Acad Sci USA* 95:14389–94; Cao et al., 1999, *Nature* 398:381. Specifically, lyophilized proteins were dissolved in phosphate buffer solutions (PBS) and used to make protein bound polymer beads, as described.

The beads were then implanted in mouse cornea. Male 5–6 week-old C57BI6/J mice were acclimated and caged in groups of six or less. Animals were anaesthetized by injection of a mixture of dormicum and hypnorm (1:1) before all procedures. Corneal micropockets were created with a modified von Graefe cataract knife in both eyes of each male 5–6-week-old C57BI6/J mouse. A micropellet (0.35×0.35 mm) of sucrose aluminum sulfate (Bukh Meditec, Copenhagen, Denmark) coated with slow-release hydron polymer type NCC (IFN Sciences, New Brunswick, N.J.) containing various amounts of homodimers of truncated PDGF-DD was surgically implanted into each cornal pocket.

For comparison purposes corresponding amounts of PDGF-AA, PDGF-AB, PDGF-BB, and PDGF-CC were similarly implanted into corneal pockets of test mice. In each case, the pellet was positioned 0.6–0.8 mm from the corneal limbus. After implantation, erythromycin/ophthalmic ointment was applied to each eye.

On day 5 after growth factor implantation, animals were sacrificed with a lethal dose of $CO_2$, and corneal neovascularization was measured and photographed with a slit-lamp stereomicroscope. In FIG. 25A-E, arrows point to the implanted pellets. Vessel length and clock hours of circumferential neovascularization were measured. Quantitation of corneal neovascularization is presented as maximal vessel length (FIG. 25F), clock hours of circumferential neovascnlarization (FIG. 25G), and area of neovascularization (FIG. 25H). Graphs represent mean values (Å SEM) of 11–16 eyes (6–8 mice) in each group.

The corneal angiogenesis model is one of the most rigorous mammalian angiogenesis models that requires a putative compound to be sufficiently potent in order to induce neovascularization in the corneal avascular tissue. Potent angiogenic factors including FGF-2 and VEGF have profound effects in this system.

The results are shown in FIG. 25. The assays were done using PDGF-AA (FIG. 25A), PDGF-AB (FIG. 25B), PDGF-BB (FIG. 25C), PDGF-CC (FIG. 25D), and PDGF-DD (FIG. 25C). FIGS. 25F-H show the quantitative analysis of vessel length, clock hours, and vessel areas (means±SD, n=4–6).

The overall angiogenic response induced by PDGF-DD was similar to that induced by other PDGF isoforms. The results again clearly demonstrate that the truncated PDGF-D homodimer exhibits marked angiogenic activity in vivo. In light of the foregoing test results, which demonstrate the in vivo angiogenesis inducing activity of PDGF-DD, treatments with PDGF-DD alone, or in combination with other angiogenic factors such as VEGF family members and FGFs, provide an attractive approach for therapeutic angiogenesis of ischemic heart, brain and limb disorders.

EXAMPLE 11

PDGF-D Promotes Connective Tissue Growth During Wound Healing

The healing of wounds is a complex process involving three discreet but overlapping stages: inflammation, proliferation and repair, and remodeling. Wound healing involves many growth factors, some of which exert different effects on multiple cell types. PDGF in general has been known to be active in all stages of the healing process and to promote wound healing. It is synthesized in significant quantities throughout the process by a number of different cells, including platelets, macrophages, fibroblasts and endothelial cells. Despite the critical role played by other growth factors involved in wound healing (EGF, FGF, insulin-like growth factors, and the TGFs), only PDGF has been shown to augment wound healing in vivo (Steed, 1998, Am. J. Surg. 176:205–255). In fact, as early as 1991, PDGF-B was used for would healing purposes. See e.g. Pierce et al., 1991, J. Biol. Chem. 45:319–326 "Role of PDGF in wound-healing" and Pierce et al., 1994, Tissue repair processes in healing chronic pressure ulcers treated with recombinant PDGF-BB, Am. J. Pathology 145:1399–1410. Nagai and Embil (2002) Expert Opin. Biol. Ther. 2:211–218 reviewed the use of recombinantly produced PDGF-B and concluded that it is safe, effective and easy to use in the treatment for healing diabetic foot ulcers.

Figure 26:
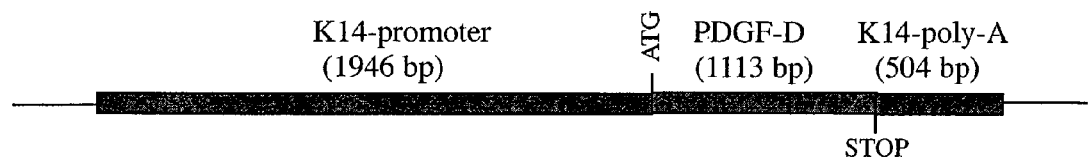
FIG. 26 is a schematic diagram showing the K14-PDGF-D construct (See Example 11).

PDGF-B and PDGF-D share the same type of receptors. The effects of PDGF-D on wound healing were investigated using transgenic mice which overexpress PDGF-D in skin keratinocytes. The human PDGF-D gene was cloned and operatively linked with the keratin 14 promoter (K-14 promoter), which directs the expression of the gene to the basal epithelial cells of the skin of transgenic animals (Jeltsch et al., 1997, Hyperplasia of lymphatic vessels in VEGF-C transgenic mice, Science 276:1423–1425; Detmar et al., 1998, Increased microvascular density and enhanced leukocyte rolling and adhesion in the skin of VEGF transgenic mice, J. Investigative Dermatol. 111:1–6). A schematic diagram of the K14-PDGF-D construct is depicted in FIG. 26.

Figure 27:
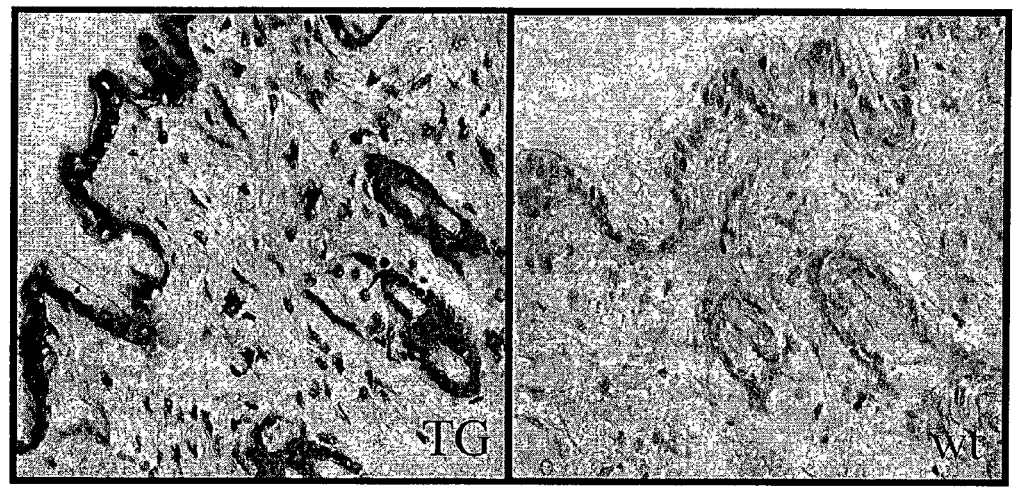
FIG. 27 shows a comparison of PDGF-D expression between K14-PDGF-D transgenic mouse (TG) and wild-type mouse (wt). Paraffin embedded mouse skin samples were stained with anti-PDGF-D. For experimental details, see Uutela et al., 2001, "Chromosomal location, exon structure and vascular expression patterns of the human PDGFC and PDGFD genes," *Circulation* 103:2242–2247.

Transgenic mice overexpressing PDGF-D in skin keratinocytes were obtained. Four mice from the same transgenic litter were tested postitive for PDGF-D and four negative. FIG. 27 shows a comparison of PDGF-D expression between K14-PDGF-D transgenic mouse (TG) and wild-type mouse (wt). Paraffin embedded mouse skin samples were stained with anti-PDGF-D. For experimental details, see Uutela et al., 2001, Chromosomal location, exon structure and vascular expression patterns of the human PDGFC and PDGFD genes, Circulation 103:2242–2247, which is incorporated herein by reference in its entirety.

Mice were then anesthesised (ksylatsine+ketaminehydrochloride) and punchbiopsy wounds were made to their flank skin (4 wounds with a diameter of 6 mm per mouse). An analgesic was used to inhibit pain (buprenorfine).

Figure 28:
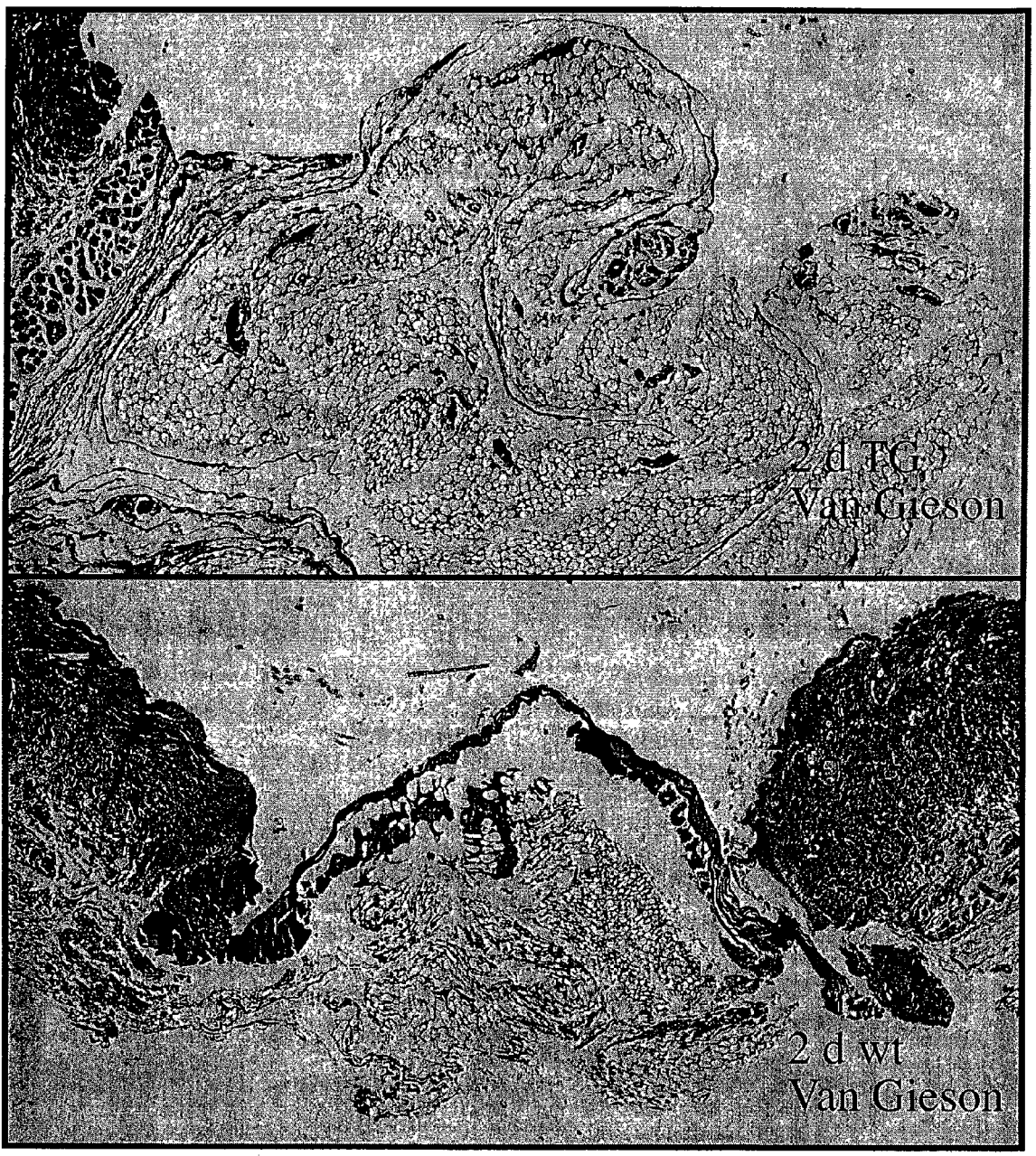
FIG. 28 shows a comparison of granulation tissue staining between K14-PDGF-D transgenic mouse (TG) and wild-type mouse (wt) in wound areas after two days. The samples were stained with the Van Gieson method which stains elastin. The amount of granulation tissue is greater in PDGF-D positive mouse (TG).

One positive and one negative mouse were sacrificed two days after the wounding, and as can be seen from FIG. 28, the amount of granulation tissue in the wound area was considerably greater in the PDGF-D positive mouse (TG) when compared with transgene negative littermate (wt).

Figure 29:
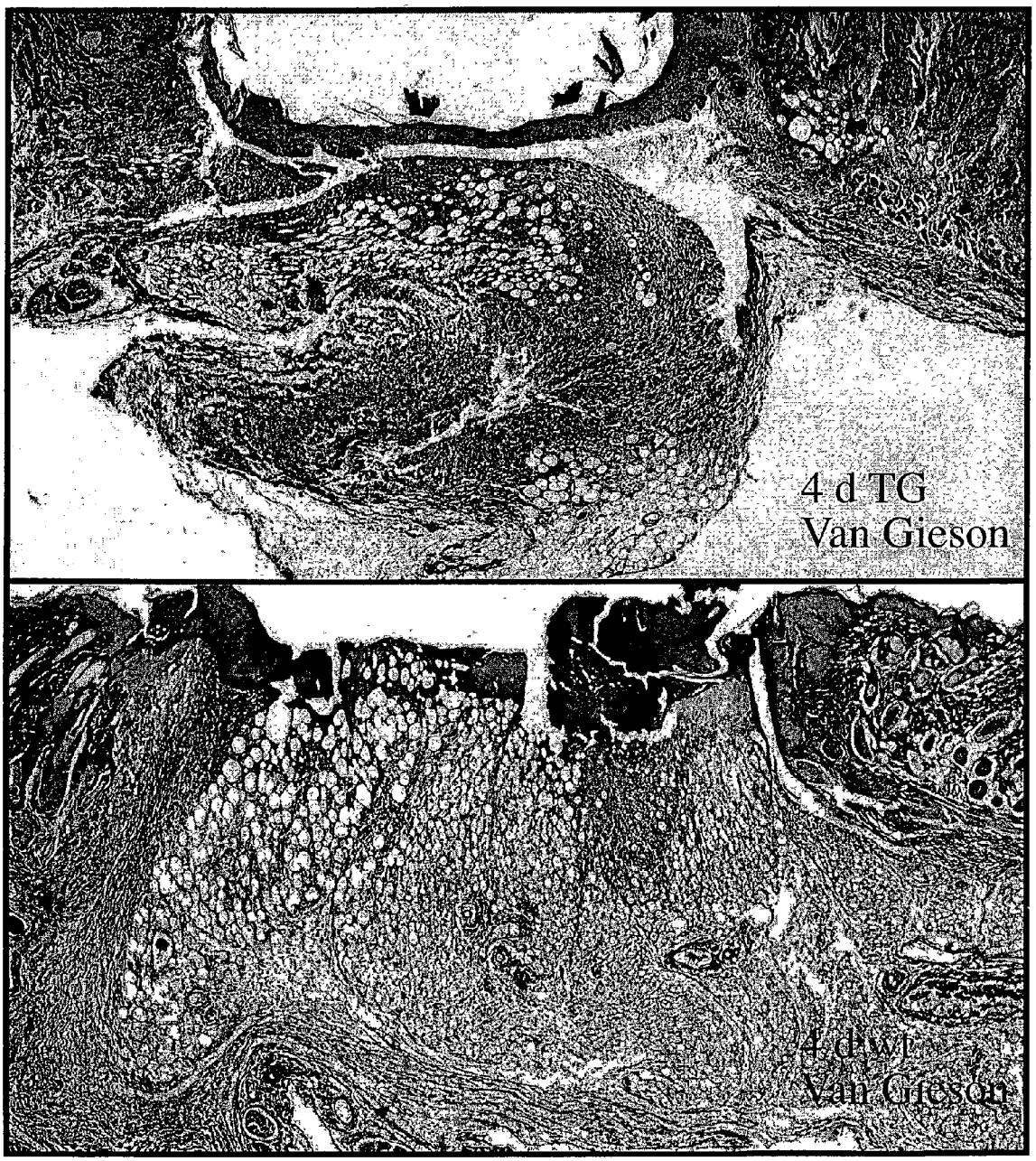
FIG. 29 shows a comparison of granulation tissue staining between K14-PDGF-D transgenic mouse (TG) and wild-type mouse (wt) in wound areas after four days. The samples were stained with the Van Gieson method which stains elastin. The amount of granulation tissue is greater in PDGF-D positive mouse (TG).
Figure 30:
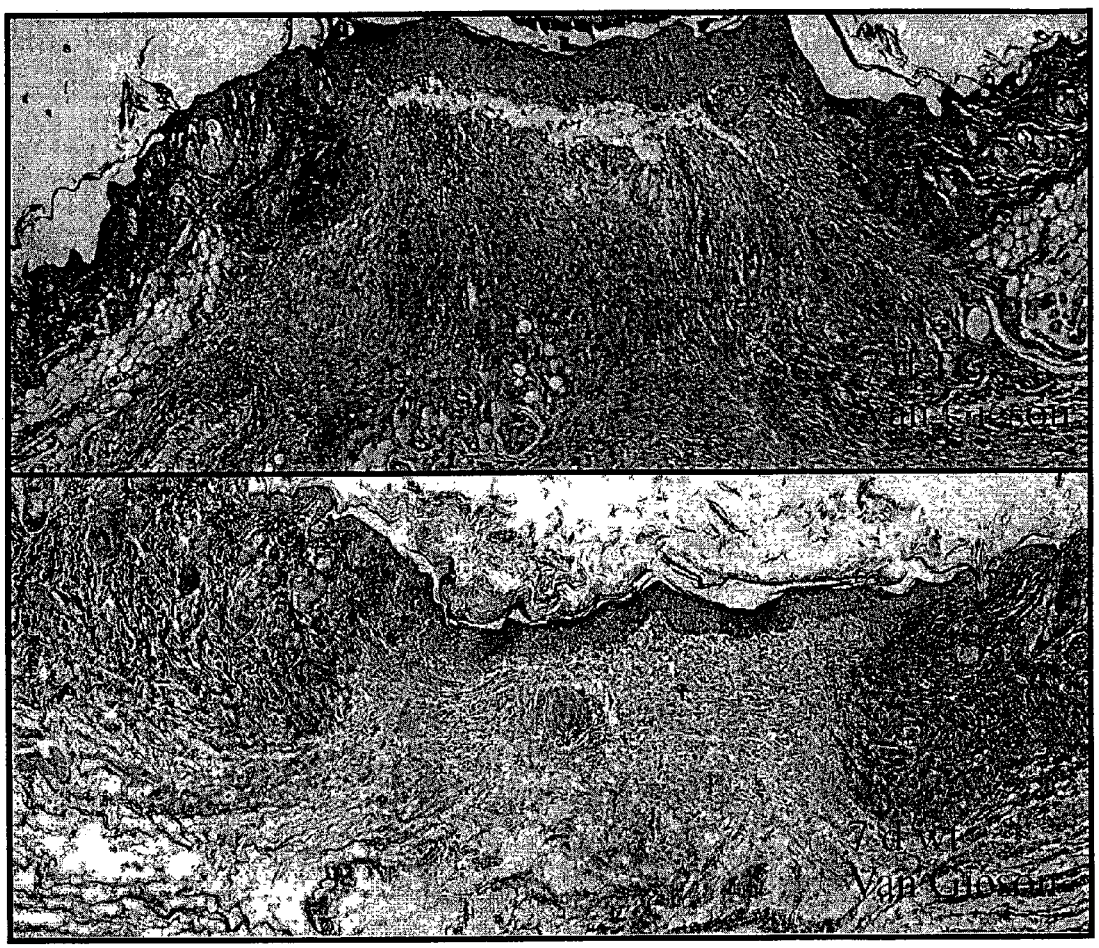
FIG. 30 shows a comparison of granulation tissue staining between K14-PDGF-D transgenic mouse (TG) and wild-type mouse (wt) in wound areas after seven days. The samples were stained with the Van Gieson method which stains elastin. The amount of granulation tissue is greater in PDGF-D positive mouse (TG).

The next mice were sacrificed after 4 days. The amount of the developing connective tissue was greater in PDGF-D expressing mouse as shown by the van Gieson elastic connnective tissue stain (FIG. 29). A similar augmentation of connective tissue development was seen in the transgenic mice sacrificed 7 and 10 days after wounding (FIG. 30).

Because increased amount of elastic connective tissue results in a greater tensile strength of the PDGF-D treated wounds, these results indicate that PDGF-D enhances the wound repair process, and that PDGF-D can be used as a valuable enhancer of wound healing.

The ability of PDGF-D to stimulate wound healing is also tested in the most clinically relevant model available, as described in Schilling et al., 1959, Surgery 46:702–710 and utilized by Hunt et al., 1967, Surgery 114:302–307.

Bioassays to Determine the Function of PDGF-D

Assays are conducted to evaluate whether PDGF-D has similar activities to PDGF-A, PDGF-B, VEGF, VEGF-B, VEGF-C and/or VEGF-D in relation to growth and/or motility of connective tissue cells, fibroblasts, myofibroblasts and glial cells; to endothelial cell function; to angiogenesis; and to wound healing. Further assays may also be performed, depending on the results of receptor binding distribution studies.

I. Mitogenicity of PDGF-D for Endothelial Cells

To test the mitogenic capacity of PDGF-D for endothelial cells, the PDGF-D polypeptide is introduced into cell culture medium containing 5% serum and applied to bovine aortic endothelial cells (BAEs) propagated in medium containing 10% serum. The BAEs are previously seeded in 24-well dishes at a density of 10,000 cells per well the day before addition of the PDGF-D. Three days after addition of this polypeptide the cells are dissociated with trypsin and counted. Purified VEGF is included in the experiment as positive control.

II. Mitogenicity of PDGF-D for Fibroblasts

To test the mitogenic capacity of PDGF-D for fibroblasts, different concentrations of truncated homodimers of PDGF-DD or PDGF-AA (as control) are added to serum starved human foreskin fibroblasts in the presence of 0.2 µmCi [3H]thymidine. The fibroblasts are then incubated for 24 hours with 1 ml of serum-free medium supplemented with 1 mg/ml BSA. After trichloroacetic acid (TCA) precipitation, the incorporation of [3H]thymidine into DNA is determined using a beta-counter. The assay is performed essentially as described in Mori et al., 1991, *J. Biol. Chem.* 266:21158–21164.

III. Assays of Endothelial Cell Function a) Endothelial Cell Proliferation

Endothelial cell growth assays are performed by methods well known in the art, e.g. those of Ferrara & Henzel, 1989, *Nature* 380:439–443, Gospodarowicz et al., 1989, *Proc. Natl. Acad. Sci. USA* 86:7311–7315, and/or Claffey et al., 1995, *Biochem. Biophys. Acta* 1246:1–9.

b) Cell Adhesion Assay

The effect of PDGF-D on adhesion of polymorphonuclear granulocytes to endothelial cells is tested.

c) Chemotaxis

The standard Boyden chamber chemotaxis assay is used to test the effect of PDGF-D on chemotaxis.

d) Plasminogen Activator Assay

Endothelial cells are tested for the effect of PDGF-D on plasminogen activator and plasminogen activator inhibitor production, using the method of Pepper et al., 1991, *Biochem. Biophys. Res. Commun.* 181:902–906.

e) Endothelial Cell Migration Assay

The ability of PDGF-D to stimulate endothelial cells to migrate and form tubes is assayed as described in Montesano et al., 1986, *Proc. Natl. Acad. Sci. USA* 83:7297–7301. Alternatively, the three-dimensional collagen gel assay described in Joukov et al., 1996, *EMBO J.* 15:290–298 or a gelatinized membrane in a modified Boyden chamber (Glaser et al., 1980, *Nature* 288:483–484) may be used.

IV. Angiogenesis Assay

The ability of PDGF-D to induce an angiogenic response in chick chorioallantoic membrane is tested as described in Leung et al., 1989, *Science*, 246:1306–1309. Alternatively the rat cornea assay of Rastinejad et al., 1989, *Cell,* 56:345–355 may be used; this is an accepted method for assay of in vivo angiogenesis, and the results are readily transferrable to other in vivo systems.

V. The Hemopoietic System

A variety of in vitro and in vivo assays using specific cell populations of the hemopoietic system are known in the art, and are outlined below. In particular a variety of in vitro murine stem cell assays using fluorescence-activated cell sorter to purified cells are particularly convenient:

a) Repopulating Stem Cells

These are cells capable of repopulating the bone marrow of lethally irradiated mice, and have the Lin$^-$, Rh$^{h1}$, Ly-6A/E$^+$, c-kit$^+$ phenotype. PDGF-D is tested on these cells either alone, or by co-incubation with other factors, followed by measurement of cellular proliferation by $^3$H-thymidine incorporation.

b) Late Stage Stem Cells

These are cells that have comparatively little bone marrow repopulating ability, but can generate D13 CFU-S. These cells have the Lin$^-$, Rh$^{h1}$, Ly-6A/E$^+$, c-kit$^+$ phenotype. PDGF-D is incubated with these cells for a period of time, injected into lethally irradiated recipients, and the number of D13 spleen colonies is enumerated.

c) Progenitor-Enriched Cells

These are cells that respond in vitro to single growth factors and have the Lin$^-$, Rh$^{h1}$, Ly-6A/E$^+$, c-kit$^+$ phenotype. This assay will show if PDGF-D can act directly on haemopoietic progenitor cells. PDGF-D is incubated with these cells in agar cultures, and the number of colonies present after 7–14 days is counted.

VI. Atherosclerosis

Smooth muscle cells play a crucial role in the development or initiation of atherosclerosis, requiring a change of their phenotype from a contractile to a synthetic state. Macrophages, endothelial cells, T lymphocytes and platelets all play a role in the development of atherosclerotic plaques by influencing the growth and phenotypic modulations of smooth muscle cell. An in vitro assay using a modified Rose chamber in which different cell types are seeded on to opposite cover slips measures the proliferative rate and phenotypic modulations of smooth muscle cells in a multicellular environment, and is used to assess the effect of PDGF-D on smooth muscle cells.

VII. Metastasis

The ability of PDGF-D to inhibit metastasis is assayed using the Lewis lung carcinoma model, for example using the method of Cao et al., 1995, *J. Exp. Med.* 182:2069–2077.

VIII. Migration of Smooth Muscle Cells

The effects of the PDGF-D on the migration of smooth muscle cells and other cells types can be assayed using the method of Koyama et al., 1992, *J. Biol. Chem.* 267:22806–22812.

IX. Chemotaxis

The effects of the PDGF-D on chemotaxis of fibroblast, monocytes, granulocytes and other cells can be assayed using the method of Siegbahn et al., 1990, *J. Clin. Invest.* 85:916–920.

X. PDGF-D in Other Cell Types

The effects of PDGF-D on proliferation, differentiation and function of other cell types, such as liver cells, cardiac muscle and other cells, endocrine cells and osteoblasts can readily be assayed by methods known in the art, such as $^3$H-thymidine uptake by in vitro cultures.

XI. Construction of PDGF-D Variants and Analogues

PDGF-D is a member of the PDGF family of growth factors which exhibits a high degree of homology to the other members of the PDGF family. PDGF-D contains seven conserved cysteine residues which are characteristic of this family of growth factors. These conserved cysteine residues form intra-chain disulfide bonds which produce the cysteine knot structure, and inter-chain disulfide bonds that form the protein dimers which are characteristic of members of the PDGF family of growth factors. PDGF-D interacts with a protein tyrosine kinase growth factor receptor.

In contrast to proteins where little or nothing is known about the protein structure and active sites needed for receptor binding and consequent activity, the design of active mutants of PDGF-D is greatly facilitated by the fact that a great deal is known about the active sites and important amino acids of the members of the PDGF family of growth factors.

Published articles elucidating the structure/activity relationships of members of the PDGF family of growth factors include for PDGF: Oestman et al., 1991, *J. Biol. Chem.,* 266:10073–10077; Andersson et al., 1992, *J. Biol. Chem.,* 267:11260–1266; Oefner et al., 1992, *EMBO J.,* 11:3921–3926; Flemming et al., 1993, *Molecular and Cell Biol.,* 13:4066–4076 and Andersson et al., 1995, *Growth Factors,* 12:159–164; and for VEGF: Kim et al., 1992, *Growth Factors,* 7:53–64; Pötgens et al., 1994, *J. Biol. Chem.,* 269:32879–32885 and Claffey et al., 1995, *Biochem. Biophys. Acta,* 1246:1–9. From these publications it is apparent that because of the eight conserved cysteine residues, the members of the PDGF family of growth factors exhibit a characteristic knotted folding structure and dimerization, which result in formation of three exposed loop regions at each end of the dimerized molecule, at which the active receptor binding sites can be expected to be located.

Based on this information, a person skilled in the biotechnology arts can design PDGF-D mutants with a very high probability of retaining PDGF-D activity by conserving the eight cysteine residues responsible for the knotted folding arrangement and for dimerization, and also by conserving, or making only conservative amino acid substitutions in the likely receptor sequences in the loop 1, loop 2 and loop 3 region of the protein structure.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

Conservative Substitutions I

| SIDE CHAIN CHARACTERISTIC | AMINO ACID |
|---|---|
| Aliphatic | |
| Non-polar | G A P<br>I L V |
| Polar - uncharged | C S T M<br>N Q |
| Polar - charged | D E<br>K R |
| Aromatic | H F W Y |
| Other | N Q D E |

Alternatively, conservative amino acids can be grouped as described in Lehninger, Biochemistry, Second Edition; Worth Publishers, Inc. NY:N.Y. (1975), pp. 71–77 as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

In particular, it is anticipated that the aforementioned peptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin).

The formation of desired mutations at specifically targeted sites in a protein structure is considered to be a standard technique in the arsenal of the protein chemist (Kunkel et al., 1987, *Methods in Enzymol.* 154:367–382). Examples of such site-directed mutagenesis with VEGF can be found in Pötgens et al., 1994, *J. Biol. Chem.* 269: 32879–32885 and Claffey et al., 1995, *Biochem. Biophys. Acta,* 1246:1–9. Indeed, site-directed mutagenesis is so common that kits are commercially available to facilitate such procedures (e.g. Promega 1994–1995 Catalog., Pages 142–145).

The connective tissue cell, fibroblast, myofibroblast and glial cell growth and/or motility activity, the endothelial cell proliferation activity, the angiogenesis activity and/or the wound healing activity of PDGF-D mutants can be readily confirmed by well-established routine screening procedures. For example, a procedure analogous to the endothelial cell mitotic assay described by Claffey et al., 1995, *Biochem. Biophys. Acta.* 1246:1–9) can be used. Similarly the effects of PDGF-D on proliferation of other cell types, on cellular differentiation and on human metastasis can be tested using methods which are well known in the art.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method for stimulating growth of a connective tissue or stimulating healing of a wound in a mammal, which method comprises administering to the mammal in need thereof an effective connective tissue growth-stimulating or wound-healing amount of a polypeptide that comprises an amino acid sequence of SEQ ID NO: 25, is at least 95% identical to SEQ ID NO: 8, and has the ability to stimulate one or more of proliferation, differentiation, motility, or survival of cells expressing a PDGF-D receptor.

2. A method according to claim 1, wherein the polypeptide comprises an amino acid sequence of SEQ ID NO:10.

3. A method according to claim 1, wherein the polypeptide comprises SEQ ID NO:8.

4. A method according to claim 1, wherein the mammal is human.

5. A method according to claim 1, wherein the polypeptide is administered in an amount ranging from about 0.1 µg/kg to about 1,000 µg/kg body weight per dose.

6. A method according to claim 1, wherein the polypeptide is administered in a composition comprising the polypeptide and a pharmaceutically acceptable carrier.

7. A pharmaceutical composition for treating a wound, or for promoting growth of a connective tissue, the composition comprising:
   (a) an effective amount of a polypeptide for stimulating connective tissue growth or stimulating wound-healing of a polypeptide said popypeptide comprising an amino acid sequence of SEQ ID NO: 25, is at least 95% identical to SEQ ID NO: 8, and has the ability to stimulate one or more of proliferation, differentiation, motility, or survival of cells expressing a PDGF-D receptor, and
   (b) a pharmaceutically acceptable carrier for delivering the polypeptide to the connective tissue or wound.

8. A pharmaceutical composition according to claim 7, wherein the carrier is a powder, an emulsion, a cream, a lotion, an ointment, a gel, a liniment, a salve, a liposomal suspension, or an immobilizing matrix.

* * * * *